(12) United States Patent
Nakashima et al.

(10) Patent No.: US 6,339,089 B2
(45) Date of Patent: *Jan. 15, 2002

(54) PYRIMIDINE NUCLEUS-CONTAINING COMPOUND AND A MEDICAMENT CONTAINING THE SAME FOR A BLOOD OXYGEN PARTIAL PRESSURE AMELIORATION, AND A METHOD FOR PREPARING THE SAME

(75) Inventors: Yoshiharu Nakashima; Takashi Fujita; Michiyo Hizuka; Hiroshi Ikawa; Toru Hiruma, all of Tokyo (JP)

(73) Assignee: Fujirebio Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,706

(22) Filed: Aug. 12, 1998

(30) Foreign Application Priority Data

Aug. 13, 1997 (JP) .............................................. 9-218767
Aug. 13, 1997 (JP) .............................................. 9-218768

(51) Int. Cl.⁷ ..................... C07D 239/95; A61K 31/517
(52) U.S. Cl. .................. 514/260; 540/600; 514/217.06; 514/228.2; 514/232.5; 514/234.8; 544/291; 544/62; 544/82; 544/116
(58) Field of Search ................................ 544/284, 291, 544/62, 82, 116; 514/260, 217.06, 228.2, 232.5, 234.8; 540/600

(56) References Cited

FOREIGN PATENT DOCUMENTS

| DE | 2 032 687 | | 1/1972 |
| EP | 0 495 982 | | 7/1992 |
| EP | 0 514 540 | | 11/1992 |
| EP | 899263 | * | 3/1999 |
| GB | 1057612 | | 2/1967 |
| WO | WO 97/19926 | | 6/1997 |

\* cited by examiner

*Primary Examiner*—John M. Ford
(74) *Attorney, Agent, or Firm*—Oblon, Spivak, McClelland, Maier & Neustadt, P.C.

(57) ABSTRACT

A pyrimidine nucleus-containing compound represented by the formula (I):

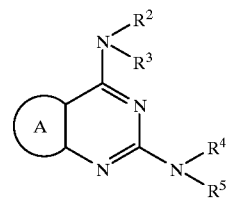

(I)

wherein ring A represents the ring of the formula (a):

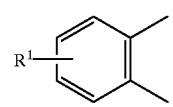

(a)

in which $R^1$ is a nitro group, an amino group, a substituted amino group or a halogen atom, or the ring of the formula (b):

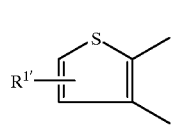

(b)

in which $R^{1'}$ is the group such as an alkyl group or an alkenyl group; $R^2$ to $R^5$ independently represent the group such as an alkyl group or an alkenyl group; with the proviso that at least one of $R^2$ to $R^5$ is an alkenyl group, or acid addition salts thereof.

7 Claims, No Drawings

PYRIMIDINE NUCLEUS-CONTAINING COMPOUND AND A MEDICAMENT CONTAINING THE SAME FOR A BLOOD OXYGEN PARTIAL PRESSURE AMELIORATION, AND A METHOD FOR PREPARING THE SAME

TECHNICAL FIELD

The present invention relates to a pyrimidine nucleus-containing compound such as a thienopyrimidine derivative or a quinazoline derivative which is useful for pharmacotherapeutically ameliorating arterial blood oxygen partial pressures ($PaO_2$) in hypoxemic patients and those patients who are under oxygen inhalation treatment due to acute respiratory insufficiency.

BACKGROUND ART

While broncodilators, antiphlogistics, cardiac insufficiency treating agents, antitussives, etc. have been used currently as neosotropic agents for treating respiratory insufficiency diseases, there is no effective medicaments for patients suffering from hypoxemia such as chronic obstructive pulmonary disease (COPD).

DISCLOSURE OF THE INVENTION

Under such circumstances, medicaments for enhancing and ameliorating $PaO_2$ values caused to be lowered by respiratory diseases have been in demand. Further, these diseases are often accompanied by increase in the arterial blood $CO_2$ partial pressure ($PaCO_2$) in addition to drop in $PaO_2$, and in such cases medicaments having $PaCO_2$ lowering actions in addition to $PaO_2$ enhancing actions have been necessitated.

The present inventors made intensive studies in search of medicaments which ameliorate blood oxygen partial pressure in hypoxemia to find that a pyrimidine nucleus-containing compound such as a thienopyrimidine derivative or a quinazoline derivative to be described later is useful for prophylaxis and therapy of hypoxemia incidental to respiratory diseases.

The compound of the present invention has actions to enhance respiratory functions in the lungs and to increase $PaO_2$ by redistribution of bloodstream based mainly on hypoxemic pulmonary vasoconstriction (HPV) enhancing actions or to increase ventilation and respiration rate whereby to increase $PaO_2$ and also to reduce $PaCO_2$.

The compound of the present invention relates to a pyrimidine nucleus-containing compound represented by the formula (I):

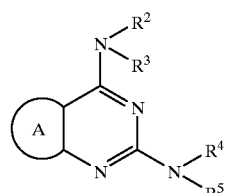

(I)

wherein ring A represents the ring of the formula (a):

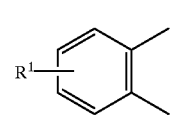

(a)

in which $R^1$ is a nitro group, an amino group, a substituted amino group or a halogen atom, or the ring of the formula (b):

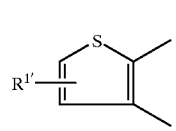

(b)

in which $R^{1'}$ is an alkyl group, an alkenyl group, a phenyl group, a nitro group, an amino group, a substituted amino group or a halogen atom;

$R^2$ and $R^4$ independently represent a hydrogen atom, an alkyl group or an alkenyl group; and $R^3$ and $R^5$ independently represent an alkyl group, an alkenyl group, an alkynyl group, an aralkyl group, a cycloalkyl group, an adamantyl group, a pyridylmethyl group, a furylmethyl group, a thienylmethyl group, a cinnamyl group, an acyl group, an alkoxycarbonyl group, a substituted alkyl group, a substituted carbamoyl group or a substituted amino group; or either $R^2$ and $R^3$ or $R^4$ and $R^5$, together with the nitrogen atom to which they are attached, may form a 4 to 7-membered saturated heteromonocyclic ring which may be substituted;

with the proviso that at least one of $R^2$ to $R^5$ is an alkenyl group, or acid addition salts thereof.

That is, the pyrimidine nucleus-containing compound of the present invention relates to a quinazoline derivative represented by the formula (II):

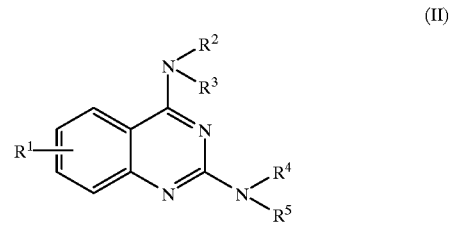

(II)

or acid addition salts thereof, or a thienopyrimidine derivative represented by the formula (III):

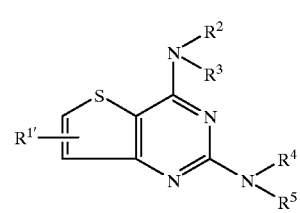

(III)

or acid addition salts thereof.

The alkyl group by which ring A (R¹) may be substituted may preferably be a $C_1$–$C_6$ alkyl group, for example, methyl, ethyl, propyl, isopropyl, n-butyl, isobutyl, sec-butyl, t-butyl, n-pentyl, neopentyl and n-hexyl. In particular, $R^{1'}$ may preferably be methyl, ethyl or propyl substituting at the 7-position of the thienopyrimidine ring.

The alkenyl group by which ring A (R¹) may be substituted may preferably be a $C_3$–$C_6$ alkenyl group, for example, allyl, cis-2-butenyl, trans-2-butenyl, 3-butenyl, 2-methyl-2-propenyl, 1-methyl-2-propenyl, 3-methyl-2-butenyl, 3-methyl-3-butenyl, 4-pentenyl, cis-2-pentenyl, trans-2-pentenyl, cis-2-hexenyl, trans-2-hexenyl and 1,4-pentadien-3-yl.

The substituted amino group by which ring A (R¹, $R^{1'}$) may be substituted may preferably be a mono- or di-$C_1$–$C_3$ alkylamino group, for example, methylamino, ethylamino, propylamino, dimethylamino, diethylamino or mono- or diallylamino.

The halogen atom by which ring A (R¹, $R^{1'}$) may be substituted includes a fluorine, chlorine, bromine or iodine atom.

The alkyl group regarding R² to R⁵ may preferably be a $C_1$–$C_{20}$ alkyl group, for example, methyl, ethyl, propyl, isopropyl, n-butyl, isobutyl, sec-butyl, t-butyl, n-pentyl, neopentyl and n-hexyl, heptyl, octyl, nonyl, decyl, undecyl, dodecyl, tridecyl, tetradecyl, pentadecyl, hexadecyl, heptadecyl, octadecyl, nonadecyl and eicosyl.

The alkenyl group regarding R² to R⁵ may preferably be $C_3$–$C_6$ alkenyl group, for example, allyl, cis-2-butenyl, trans-2-butenyl, 3-butenyl, 2-methyl-2-propenyl, 1-methyl-2-propenyl, 3-methyl-2-butenyl, 3-methyl-3-butenyl, 4-pentenyl, cis-2-pentenyl, trans-2-pentenyl, cis-2-hexenyl, trans-2-hexenyl and 1,4-pentadien-3-yl.

With respect to the substituent group regarding R³ and R⁵, the alkynyl group includes, for example, 2-propynyl, 2-butynyl, 2-pentynyl, 2-heptynyl; the aralkyl group includes, for example, benzyl, phenetyl, 1-naphthylmethyl and 2-naphthylmethyl, preferably benzyl; the cycloalkyl group, which may preferably be a $C_3$–$C_6$ cycloalkyl group, includes, for example, cyclopropyl, cyclobutyl, cyclopentyl and cyclohexyl; the adamantyl group includes, for example, 1-adamantyl, 2-adamantyl; the pyridylmethyl group includes, for example, 2-pyridylmethyl and 3-pyridylmethyl; the furylmethyl group includes, for example, furfuryl and 3-furylmethyl; the thienylmethyl group includes, for example, 2-thienyl and 3-thienylmethyl; the acyl group, which may preferably be a $C_1$–$C_6$ aliphatic acyl group, includes, for example, formyl, acetyl, propionyl, butyryl, valeryl, hexanoyl; the alkoxycarbonyl group, which may preferably be a $C_1$–$C_6$ alkoxycarbonyl group, includes, for example, methoxycarbonyl, ethoxycarbonyl, propyloxycarbonyl, 2-methylpropyloxycarbonyl, t-butyloxycarbonyl, pentyloxycarbonyl, hexyloxycarbonyl; the substituted alkyl group includes, for example, alkoxy-, amino-, carbamoyl-, hydroxy- or halo-substituted alkyl, for example, methoxymethyl, 2-methoxyethyl, 2-ethoxyethyl, 2-propoxyethyl, 3-methoxypropyl, 2-hydroxyethyl, 3-hydroxypropyl, 1,3-dihydroxypropyl, 2-aminoethyl, 3-aminopropyl, 4-aminobutyl, 2-carbamoylethyl, 3-carbamoylpropyl, 2-(N-methylcarbamoyl)ethyl, 3-(N-ethylcarbamoyl)propyl, 2-(N-allylcarbamoyl)ethyl, 2-(piperazinocarbonyl)ethyl, chloromethyl, 2-fluoroethyl, 2,2,2-trifluoroethyl, 3-chloropropyl; the substituted carbamoyl group, which may preferably be a $C_1$–$C_9$ linear alkyl- or alkenyl-carbamoyl, a $C_3$–$C_8$ cycloalkyl- or cycloalkenyl-carbamoyl, an arylcarbamoyl or a heteromonocyclic ring-containing carbamoyl group, includes, for example, methylcarbamoyl, ethylcarbamoyl, propylcarbamoyl, t-butylcarbamoyl, n-butylcarbamoyl, nonylcarbamoyl, cyclohexylcarbamoyl, allylcarbamoyl, 1-pyrrolidinocarbonyl, piperidinocarbonyl, morpholinocarbonyl, 1-thiomorpholinocarbonyl; and the substituted amino group, which may preferably be a mono- or di-$C_1$–$C_6$ alkyl-amino group or a heteromonocyclic ring containing amino group, includes, for example, methylamino, ethylamino, propylamino, t-butylamino, pentylamino, heptylamino, dimethylamino, diethylamino, dipropylamino, 1-pyrrolidino, piperidino, morpholino, 1-thiomorpholinyl. substituted amino group, which may preferably be a mono- or di-$C_1$–$C_6$ alkyl-amino group or a heteromonocyclic ring-containing amino group, includes, for example, methylamino, ethylamino, propylamino, t-butylamino, pentylamino, heptylamino, dimethylamino, diethylamino, dipropylamino, 1-pyrrolidino, piperidino, morpholino, 1-thiomorpholinyl.

The 4 to 7-membered saturated heteromonocyclic ring formed by R² and R³ or R⁴ and R⁵ together with the nitrogen atom to which they are attached includes, for example, 1-aziridinyl, 1-azetidinyl, 1-pyrrolidinyl, piperidino, 1-perhydroazepinyl, piperazino, morpholino and 1-thiomorpholinyl, which may be substituted on the rings with lower alkyl groups such as methyl, ethyl and propyl, a benzyl group, a naphthylmethyl group, a benzhydryl group and a 4,4'-difluorobenzhydryl group.

The acid addition salts include inorganic acid salts such as of hydrochloric acid and sulfuric acid and organic acid salts such as of acetic acid, propionic acid, citric acid, maleic acid, tartaric acid, methanesulfonic acid and p-toluenesulfonic acid.

The pyrimidine nucleus-containing compound represented by the formula (I) can be synthesized by the method which comprises the steps of:

a) reacting a 2,4-dione compound represented by the formula:

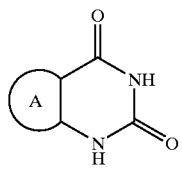

wherein ring A is the same as defined above, with a halogenating reagent in the presence of a base to prepare a 2,4-dihalo compound represented by the formula:

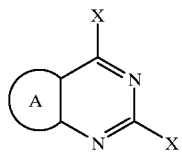

wherein X is a halogen atom, b) reacting said 2,4-dihalo compound with an amine derivative represented by the formula:

wherein $R^2$ and $R^3$ are the same as defined above,
to prepare a 2-halo-4-amino compound represented by the formula:

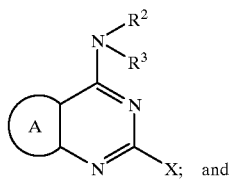

c) reacting said a 2-halo-4-amino compound with an amine compound represented by the formula:

wherein $R^4$ and $R^5$ are the same as defined above, to prepare said compound of the formula (I).

In particular, the quinazoline derivative of the formula (II) can be synthesized according to a method as shown by the following reaction scheme:

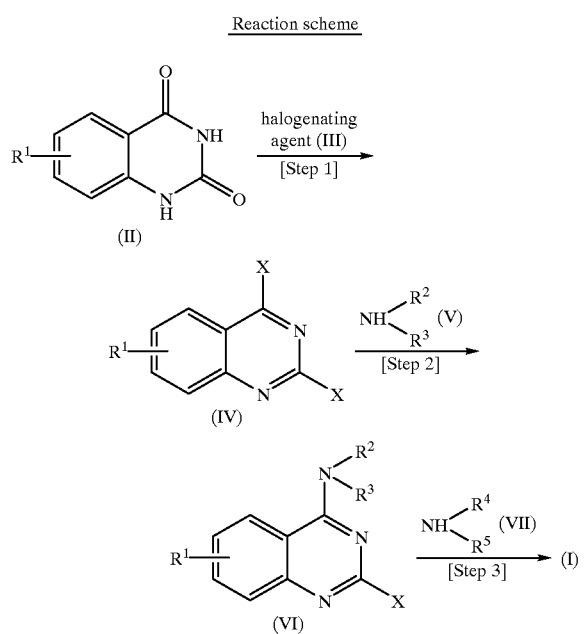

X: (halogen atom)

In Step 1, a quinazolidione derivative (II) is reacted with a halogenating reagent (III) in the presence of a base to prepare a 2,4-dihaloquinazoline derivative (IV). The starting material quinazolidione derivative (II) can be prepared easily by reacting 2-aminobenzoic acid, which may be substituted, with urea (J. Med. Chem., 1995, 38, 2763–2773). As the halogenating reagent, there may be employed phosphorus oxychloride, phosphorus pentachloride or thionyl chloride; while an organic base such as N,N-dimethylaniline, N,N-diethylaniline, triethylamine, pyridine and collidine is employed as the base. The reaction can be carried out in the absence of solvents or in the presence of an inert solvent at 50 to 200° C.

In Step 2, the 2,4-dihaloquinazoline derivative (IV) is reacted with an amine derivative (V) to prepare a 2-halo-4-aminoquinazoline derivative (VI). The reaction can be carried out in an inert solvent such as N,N-dimethylformamide (DMF), tetrahydrofuran (THF), dioxane, dimethylsulfoxide (DMSO) and chloroform at −78 to 100° C. Besides such organic bases, the reaction may be employed in the presence of an inorganic base such as sodium carbonate, potassium carbonate, sodium methoxide and potassium t-butoxide.

In Step 3, the 2-halo-4-aminoquinazoline derivative (VI) is reacted with an amine derivative (VII) to prepare a quinazoline derivative (I). The reaction can be carried out in the absence of solvents or in the presence of the above-mentioned inert solvent at 0 to 250° C. An addition of the organic base or the inorganic base as mentioned above is preferable in order to carry out the reaction efficiently.

The thienopyrimidine derivative of the formula (III) can be synthesized according to a method as shown by the following reaction scheme:

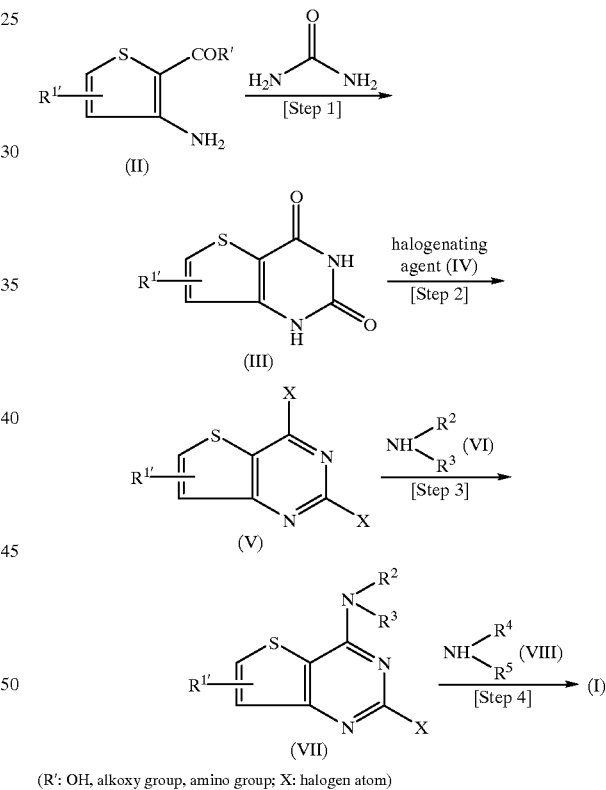

(R': OH, alkoxy group, amino group; X: halogen atom)

In Step 1, a 3-aminothiophene derivative (II) is reacted with urea to prepare a thienopyrimidine-2,4-dione derivative (III). The reaction can be carried out in the absence of solvents or in the presence of an inert organic solvent such as DMF and DMSO at 0 to 250° C.

In Step 2, the thienopyrimidine-2,4-dione derivative (III) is reacted with a halogenating reagent (IV) in the presence of a base to prepare a 2,4-dihalothienopyrimidine derivative (V). As the halogenating reagent, there may be employed phosphorus oxychloride, phosphorus pentachloride or thionyl chloride; while an organic base such as N,N-dimethylaniline, N,N-diethylaniline, triethylamine, pyridine and collidine is employed as the base. The reaction can be carried out in the absence of solvents or in the presence of an inert solvent at 0 to 200° C.

In Step 3, the 2,4-dihalothienopyrimidine derivative (V) is reacted with an amine derivative (VI) to prepare a 2-halo-4-aminothienopyrimidine derivative (VII). The reaction can be carried out in an inert solvent such as DMF, THE, dioxane, DMSO and chloroform at a reaction temperature of −78 to 100° C. Besides such organic bases, there may be employed an inorganic base such as sodium carbonate, potassium carbonate, sodium methoxide and potassium t-butoxide.

In Step 4, the 2-halo-4-aminothienopyrimidine derivative (VII) is reacted with an amine derivative (VIII) to prepare a thienopyrimidine derivative (I). The reaction can be carried out in the absence of solvents or in the presence of the above-mentioned inert at 0 to 250° C. Addition of the organic base or the inorganic base is preferable in order to carry out the reaction efficiently.

Since the pyrimidine nucleus-containing compound of the present invention indicates the excellent $PaO_2$ enhancing actions and very little toxicity, it is useful as a medicament for prophylaxis and therapy of hypoxemia.

The present invention relates also to pharmaceutical compositions containing a compound of formula (I) in combination with one or more pharmaceutically acceptable excipients.

Among the pharmaceutical compositions according to the invention there may be mentioned more especially those which are suitable for oral, parenteral, nasal, percutaneous, transcutaneous, rectal, perlingual, ocular or respiratory administration and especially tablets, dragees, sublingual tablets, sachets, paquets, gelatin capsules, glossettes, lozenges, suppositories, creams, ointments, dermal gels and drinkable or injectable ampoules, etc.

The dosage varies according to the sex, age and weight of the patient, the administration route, the nature of the therapeutic indication, or possible associated treatments, and the ranges from 0.01 mg to 1 g per 24 hours in 1 or more administration.

EXAMPLES

The present invention will be described below more specifically by way of reference examples, examples and a test example.

Reference Example 1

4-Allylamino-2,6-dichloroquinazoline

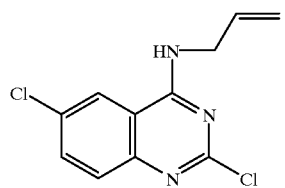

To 2.00 g (10.17 mmol) of 6-chloroquinazoline-2,4 (1H, 3H)-dione were added 8.88 g (57.93 mmol) of phosphorus oxychloride and 822 mg (6.81 mmol) of N,N-dimethylaniline, and the resulting mixture was subjected to heating under reflux for 16 hours. The reaction mixture was poured into ice water, and crystals thus precipitated were filtered to obtain 1.98 g of 2,4,6-trichloroquinazoline as crude crystals. The crude crystals were dissolved in 5 ml of DMF, and after 1.16 g (20.34 mmol) of allylamine was added to the resulting solution, the mixture was stirred under ice cooling for one hour and then at room temperature for one hour. The reaction mixture was poured into water, followed by extraction with ethyl acetate, washing with brine and drying over anhydrous sodium sulfate. After the solvent was distilled off, the residue was purified by a silica gel column to give 1.11 g (yield: 43.0%) of the title compound.

NMR (δ, $CDCl_3$): 4.29–4.35 (2H, m), 5.29 (1H, d with fine couple, J=10 Hz), 5.35 (1H, d with fine couple, J=17 Hz), 5.82 (1H, br), 5.96–6.09 (1H, m), 7.67–7.76 (3H, m)

EI-Mass (m/z, %): 257 ($M^+$+4, 4), 255 ($M^+$+2, 24), 253 ($M^+$, 38), 238 (100)

Example 1

2,4-Diallylamino-6-chloroquinazoline

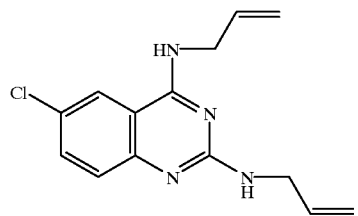

In 1 ml of 1,3-dimethyl-2-imidazolidinone was dissolved 300 mg (1.18 mmol) of 4-allylamino-2,6-dichloroquinazoline, and after 110 mg (1.87 mmol) of allylamine was added to the resulting solution, the mixture was stirred in a sealed tube at 100° C. for 10 hours. A saturated aqueous sodium hydrogen carbonate solution was added to the reaction mixture, followed by extraction with ethyl acetate, washing with brine and drying over anhydrous sodium sulfate. After the solvent was distilled off, the residue was purified by a silica gel column to give 283 mg (yield: 87.3%) of the title compound.

m.p.: 78 to 79° C.

NMR (δ, $CDCl_3$): 4.11–4.16 (2H, m), 4.20–4.25 (2H, m), 5.04 (1H, br), 5.11–5.33 (4H, m), 5.46 (1H, br), 5.93–6.07 (2H, m), 7.37–7.48 (3H, m)

EI-Mass (m/z, %): 276 ($M^+$+2, 12), 274 ($M^+$, 36), 259 (100), 233 (14)

IR (ν, $cm^{-1}$), KBr: 3476, 2920, 1572, 1482, 1408, 830

Reference Example 2

4-Allylamino-2-chloro-6-methylaminoquinazoline

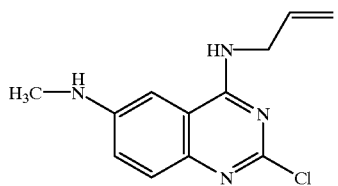

In 1 ml of DMF was dissolved 100 mg (0.438 mmol) of 2,4-dichloro-6-methylaminoqunazoline, and after 50 mg (0.88 mmol) of allylamine was added to the resulting solution, the resulting mixture was stirred under ice cooling for 30 minutes and then at room temperature for 30 minutes. The reaction mixture was poured into water, and crystals thus precipitated were filtered, followed by extraction with ethyl acetate, washing with brine and drying over anhydrous sodium sulfate. After the solvent was distilled off, the residue was purified by a silica gel column to give 100 mg (yield: 91.8%) of the title compound.

NMR (δ, CDCl$_3$): 2.94 (3H, s), 4.11 (1H, br), 4.30–4.34 (2H, m), 5.25 (1H, d with fine couple, J=10 Hz), 5.34 (1H, d with fine couple, J=17 Hz), 5.61 (1H, br), 5.99–6.12 (1H, m), 6.41 (1H, d, J=3 Hz), 7.09 (1H, dd, J=9 Hz, 3 Hz), 7.60 (1H, d, J=9 Hz)

EI-Mass (m/z, %): 250 (M$^+$+2, 27), 248 M$^+$, 82), 233 (100)

Example 2

2,4-Diallylamino-6-methylaminoquinazoline hydrochloride

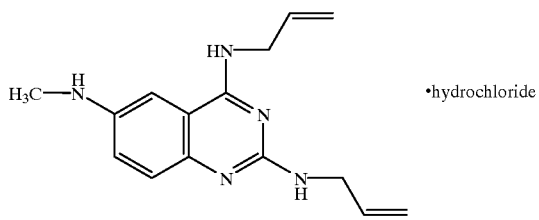

In a sealed tube were stirred 100 mg (0.40 mmol) of 4-allylamino-2-chloro-6-methylaminoquinazoline and 761 mg (13.33 mmol) of allylamine at 140° C. for 22 hours. A saturated aqueous sodium hydrogen carbonate was added to the reaction mixture, followed by extraction with ethyl acetate, washing with brine and drying over anhydrous sodium sulfate. After the solvent was distilled off, the residue was purified by a silica gel column to give 100 mg (yield: 92.4%) of a free base compound of the title compound.

NMR (δ, CDCl$_3$): 2.89 (3H, s), 3.70 (1H, br), 4.13 (2H, t, J=6 Hz), 4.25 (2H, t, J=6 Hz), 4.82 (1H, br), 5.09–5.33 (4H, m), 5.39 (1H, br), 5.95–6.11 (2H, m), 6.44 (1H, d, J=3 Hz), 6.99 (1H, dd, J=9 Hz, 3 Hz), 7.36 (1H, d, J=9 Hz)

Subsequently, a 4N hydrochloric acid-ethyl acetate solution was added dropwise to a solution of 90 mg (0.33 mmol) of the free base compound of the title compound in ethyl acetate. Crystals thus precipitated were filtered to give 85 mg (84.5%) of the title compound.

m.p.: 155 to 158° C.

NMR (δ, DMSO-d$_6$, 55° C.): 2.79 (3H, s), 4.06–4.09 (2H, m), 4.21–4.24 (2H, m), 4.76 (1H, br), 5.13–5.28 (4H, m), 5.88–6.03 (2H, m), 7.23 (1H, dd, J=9 Hz, 2 Hz), 7.29 (1H, d, J=2 Hz), 7.36 (1H, d, J=9 Hz), 8.00 (1H, br), 9.52 (1H, br), 12.47 (1H, br)

EI-Mass (m/z, %): 269 (M$^+$, 85), 254 (100), 228 (14)

IR (ν, cm$^{-1}$), KBr: 3064, 1652, 1612, 1580, 1416, 1340, 992

Reference Example 3

4-Allylamino-2-chloro-6-nitroquinazoline

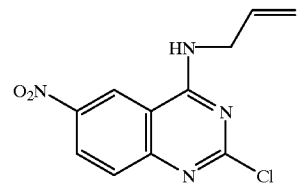

To 2.00 g (9.66 mmol) of 6-nitroquinazoline-2,4 (1H,3H)-dione was added 82.30 g (0.54 mmol) of phosphorus oxychloride, and the resulting mixture was subjected to heating under reflux for 4 days. After the phosphorus oxychloride was removed, the residue was subjected to crystallization from diethyl ether-hexane to obtain 3.10 g of 2,4-dichloro-6-nitroquinazoline as crude crystals. The compound was dissolved in 15 ml of DMF, and after 1.10 g (19.32 mmol) of allylamine was added to the resulting solution under ice cooling, the mixture was stirred under ice cooling for 2 hours. Water was added to the reaction mixture, followed by extraction with ethyl acetate, washing with brine and drying over anhydrous sodium sulfate. After the solvent was distilled off, the residue was purified by a silica gel column to give 1.77 g (yield: 69.1%) of the title compound.

NMR (δ, CDCl$_3$): 4.38 (2H, t, J=6 Hz), 5.34 (1H, d with fine couple, J=10 Hz), 5.39 (1H, d with fine couple, J=17 Hz), 5.98–6.11 (1H, m), 6.33 (1H, br), 7.88 (1H, d, J=9 Hz), 8.53 (1H, dd, J=9 Hz, 2 Hz), 8.73 (1H, d, J=2 Hz)

EI-Mass (m/z, %): 266 (M$^+$+2, 16), 264 (M$^+$, 49), 249 (100)

Example 3

2,4-Diallylamino-6-nitroquinazoline

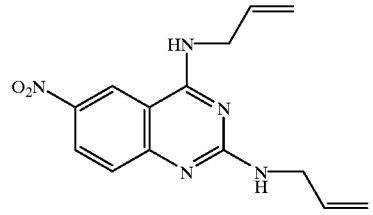

A mixture of 265 mg (1.00 mmol) of 4-allylamino-2-chloro-6-nitroquinazoline and 1.52 g (26.65 mmol) of allylamine were stirred at room temperature for 2.5 hours. Water was added to the reaction mixture, and crystals thus precipitated were filtered out to give 230 mg (yield: 80.6%) of the title compound.

m.p.: 198 to 200° C. (dec.)

NMR (δ, CDCl$_3$ 55° C.): 4.16–4.19 (2H, m), 4.25 (2H, t, J=6 Hz), 5.14–5.36 (5H, m), 5.75 (1H, br), 5.93–6.06 (2H, m), 7.41 (1H, d, J=9 Hz), 8.29 (1H, dd, J=9 Hz, 3 Hz), 8.50 (1H, d, J=3 Hz)

EI-Mass (m/z, %): 285 (M$^+$, 65), 270 (100), 224 (26), 198 (11)

IR (ν, cm$^{-1}$), KBr: 3400, 3260, 3084, 1612, 1554, 1484, 1308, 1166, 832

Example 4

4-Allylamino-6-nitro-2-propylaminoquinazoline

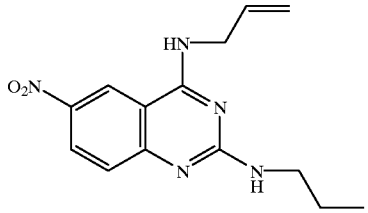

A mixture of 250 mg (0.95 mmol) of 4-allylamino-2-chloro-6-nitroquinazoline and 719 mg (12.16 mmol) of propylamine were stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 211 mg (yield: 77.7%) of the title compound.

m.p.: 197 to 198° C.

NMR ($\delta$, CDCl$_3$, 45° C.): 1.00 (3H, t, J=7 Hz), 1.61–1.73 (2H, m), 3.49 (2H, td, J=7 Hz, 7 Hz), 4.26 (2H, t, J=5 Hz), 5.25–5.36 (3H, m), 5.80 (1H, br), 5.95–6.09 (1H, m), 7.40 (1H, d, J=9 Hz), 8.28 (1H, dd, J=9 Hz, 2 Hz), 8.50 (1H, d, J=2 Hz)

EI-Mass (m/z, %): 287 (M$^+$, 86), 272 (56), 258 (83), 245 (100), 230 (73), 212 (62)

IR ($\nu$, cm$^{-1}$), KBr: 3420, 3260, 1588, 1556, 1482, 1302, 1170, 832

Example 5

4-Allylamino-2-neopentylamino-6-nitroquinazoline

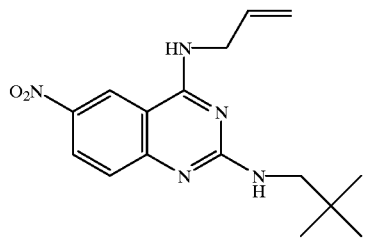

In 0.5 ml of acetonitrile were dissolved 250 mg (0.95 mmol) of 4-allylamino-2-chloro-6-nitroquinazoline and 740 mg (8.49 mmol) of neopentylamine, and the resulting solution was stirred at room temperature for 5 hours. Water was added to the reaction mixture, followed by extraction with ethyl acetate, washing with brine and drying over anhydrous sodium sulfate. After the solvent was distilled off, the residue was purified by a silica gel column to give 215 mg (yield: 72.2%) of the title compound.

m.p.: 167 to 168° C.

NMR ($\delta$, CDCl$_3$, 45° C.): 0.99 (9H, s), 3.38 (2H, d, J=7 Hz), 4.26 (2H, t, J=6 Hz), 5.26 (1H, d with fine couple, J=10 Hz), 5.34 (1H, d with fine couple, J=17 Hz), 5.82 (2H, br), 5.96–6.10 (1H, m), 7.38 (1H, d, J=9 Hz), 8.27 (1H, dd, J=9 Hz, 2 Hz), 8.50 (1H, d, J=2 Hz)

EI-Mass (m/z, %): 315 (M$^+$, 25), 258 (100), 212 (30)

IR ($\nu$, cm$^{-1}$), KBr: 3416, 3240, 2960, 1588, 1540, 1484, 1306, 922

Example 6

4-Allylamino-2-benzylamino-6-nitroquinazoline

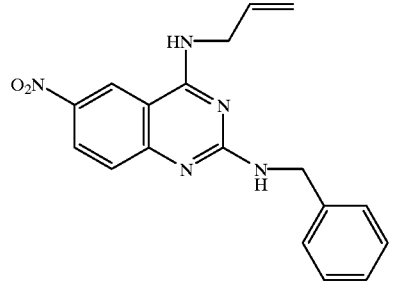

In 1 ml of DMF were dissolved 250 mg (0.95 mmol) of 4-allylamino-2-chloro-6-nitroqunazoline and 981 mg (9.15 mmol) of benzylamine, and the resulting solution was stirred at room temperature for 5 hours. Water was added to the reaction mixture, followed by extraction with ethyl acetate, washing with brine and drying over anhydrous sodium sulfate. After the solvent was distilled off, the residue was purified by a silica gel column to give 243 mg (yield: 76.7%) of the title compound.

m.p.: 216 to 217° C.

NMR ($\delta$, DMSO-d$_6$, 55° C.): 4.11–4.15 (2H, m), 4.58 (2H, d, J=6 Hz), 5.10 (1H, d, J=10 Hz), 5.21 (1H, d, J=17 Hz), 5.88–6.02 (1H, m), 7.17–7.36 (6H, m), 7.66 (1H, br), 8.20 (1H, dd, J=9 Hz, 2 Hz), 8.67 (1H, br), 9.09 (1H, d, J=2 Hz)

EI-Mass (m/z, %): 335 (M$^+$, 100), 294 (28), 248 (19), 91 (32)

IR ($\nu$, cm$^{-1}$), KBr: 3424, 3260, 1612, 1556, 1482, 1304, 832

Example 7

4-Allylamino-2-cyclohexylamino-6-nitroquinazoline

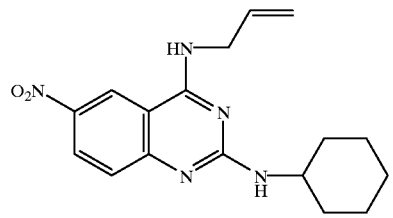

A mixture of 250 mg (0.95 mmol) of 4-allylamino-2-chloro-6-nitroquinazoline and 867 mg (8.74 mmol) of cyclohexylamine was stirred at room temperature for 5 hours. Water was added to the reaction mixture, followed by extraction with ethyl acetate, washing with brine and drying over anhydrous sodium sulfate. After the solvent was distilled off, the residue was purified by a silica gel column to give 237 mg (yield: 76.6%) of the title compound.

m.p. : 183 to 184° C.

NMR ($\delta$, CDCl$_3$, 45° C.): 1.20–1.81 (8H, m), 2.04–2.09 (2H, m), 3.94–4.04 (1H, m), 4.24 (2H, t, J=6 Hz), 5.15 (1H, br), 5.23–5.36 (2H, m), 5.72 (1H, br), 5.95–6.08 (1H, m), 7.37 (1H, d, J=9 Hz), 8.27 (1H, dd, J=9 Hz, 2 Hz), 8.48 (1H, d, J=2 Hz)

EI-Mass (m/z, %): 327 (M$^+$, 49), 286 (13), 245 (100), 230 (42)

IR (ν, cm$^{-1}$), KBr: 3420, 2932, 1588, 1546, 1302, 1168, 836

Example 8

4-Allylamino-2-(2-methoxyethylamino)-6-nitroquinazoline

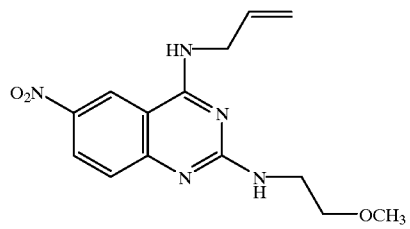

A mixture of 250 mg (0.95 mmol) of 4-allylamino-2-chloro-6-nitroquinazoline and 864 mg (11.50 mmol) of 2-methoxyethylamine was stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 214 mg (yield: 74.7%) of the title compound.

m.p.: 164 to 165° C.

NMR (δ, CDCl$_3$, 45° C.): 3.40 (3H, s), 3.59 (2H, t, J=5 Hz), 3.72 (2H, td, J=5 Hz, 5 Hz), 4.25 (2H, t, J=6 Hz), 5.24 (1H, d with fine couple, J=10 Hz), 5.32 (1H, d with fine couple, J=17 Hz), 5.85 (1H, br), 5.92–6.08 (2H, m), 7.40 (1H, d, J=9 Hz), 8.28 (1H, dd, J=9 Hz, 2 Hz), 8.53 (1H, d, J=2 Hz)

EI-Mass (m/z, %): 303 (M$^+$, 41), 288 (52), 258 (100), 212 (80)

IR (ν, cm$^{-1}$), KBr: 3424, 3256, 1586, 1558, 1480, 1308, 1126, 830

Example 9

4-Allylamino-2-diallylamino-6-nitroquinazoline

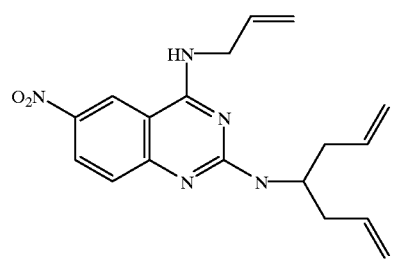

A mixture of 300 mg (1.13 mmol) of 4-allylamino-2-chloro-6-nitroquinazoline and 1.18 g (12.15 mmol) of diallylamine for 2 hours was stirred at room temperature, and then at 60° C. for one hour. Water was added to the reaction mixture, followed by extraction with ethyl acetate, washing with brine and drying over anhydrous sodium sulfate. After the solvent was distilled off, the residue was purified by a silica gel column to give 325 mg (yield: 88.5%) of the title compound.

m.p.: 167 to 168° C.

NMR (δ, CDCl$_3$, 50° C.): 4.24 (2H, t, J=6 Hz), 4.34 (4H, d, J=5 Hz), 5.14–5.35 (6H, m), 5.72 (1H, br), 5.84–6.08 (3H, m), 7.44 (1H, br), 8.26 (1H, dd, J=9 Hz, 2 Hz), 8.48 (1H, d, J=2 Hz)

EI-Mass (m/z, %): 325 (M$^+$, 26), 284 (100), 271 (37), 238 (69)

IR (ν, cm$^{-1}$), KBr: 3416, 1622, 1586, 1518, 1316, 920

Example 10

2-Allylamino-6-nitro-4-propylaminoquinazoline

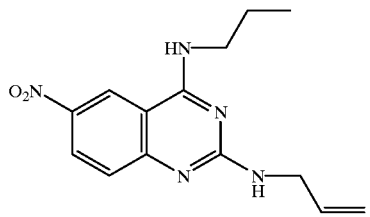

To 367 mg (1.77 mmol) of 6-nitroquinazoline-2,4 (1H, 3H)-dione was added 15.13 g (98.70 mmol) of phosphorus oxychloride, and the resulting mixture was subjected to heating under reflux for 4 days. After the phosphorus oxychloride was removed, the residue was subjected to crystallization from diethyl ether-hexane to obtain 550 mg of 2,4-dichloro-6-nitroquinazoline as crude crystals. The crude crystals were dissolved in 5 ml of DMF, and after 209 mg (3.54 mmol) of propylamine was added dropwise to the resulting solution under ice cooling, the mixture was stirred under ice cooling for 2 hours. Water was added to the reaction mixture, and crystals thus precipitated were filtered out to obtain 2-chloro-6-nitro-4-propylaminoquinazoline. To this was added 1.52 g (26.65 mmol) of allylamine, and the resulting mixture was stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 231 mg (yield: 45.4%) of the title compound.

m.p.: 211 to 212° C.

NMR (δ, CDCl$_3$, 45° C.): 1.04 (3H, t, J=7 Hz), 1.70–1.82 (2H, m), 3.59 (2H, td, J=7 Hz, 7 Hz), 4.18 (2H, t, J=6 Hz), 5.16 (1H, d with fine couple, J=10 Hz), 5.28 (1H, d with fine couple, J=17 Hz), 5.47 (1H, br), 5.79 (1H, br), 5.92–6.05 (1H, m), 7.42 (1H, d, J=9 Hz), 8.29 (1H, dd, J=9 Hz, 2 Hz), 8.49 (1H, d, J=2 Hz)

EI-Mass (m/z, %): 287 (M$^+$, 43), 272 (100), 226 (30)

IR (ν, cm$^{-1}$), KBr: 3412, 3256, 1588, 1556, 1484, 1316, 1168, 832

Example 11

2-Allylamino-4-neopentylamino-6-nitroquinazoline

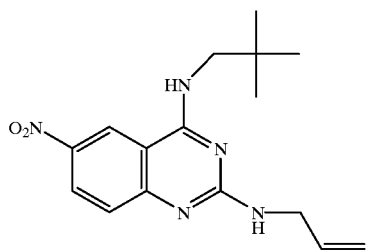

To 367 mg (1.77 mmol) of 6-nitroquinazoline-2,4 (1H, 3H)-dione was added 15.13 g (98.70 mmol) of phosphorus oxychloride to effect reaction in the same manner as in Example 10. Next, to the reaction mixture was added dropwise 309 mg (3.54 mmol) of neopentylamine under ice cooling, and the resulting mixture was stirred under ice cooling for 2 hours. Water was added to the reaction mixture, and crystals thus precipitated were filtered out to obtain 2-chloro-4-neopentylamino-6-nitroquinazoline. The compound was dissolved in 2 ml of DMF, and after 1.52 g (26.65 mmol) of allylamine was added to the resulting solution, the mixture was stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 210 mg (yield: 37.6%) of the title compound.

m.p. : 216 to 217° C.

NMR (δ, CDCl$_3$, 45° C.): 1.05 (9H, s), 3.50 (2H, d, J=6 Hz), 4.18 (2H, t, J=6 Hz), 5.17 (1H, d with fine couple, J=10 Hz), 5.29 (1H, d with fine couple, J=17 Hz), 5.39 (1H, br), 5.79 (1H, br), 5.93–6.05 (1H, m), 7.43 (1H, d, J=9 Hz), 8.31 (1H, dd, J=9 Hz, 2 Hz), 8.49 (1H, d, J=2 Hz)

EI-Mass (m/z, %): 315 (M$^+$, 40), 300 (100), 285 (26), 270 (48), 258 (16), 228 (8), 212 (17)

IR (ν, cm$^{-1}$), KBr: 3436, 3252, 2964, 1602, 1562, 1484, 1294, 1164, 834

Example 12

2-Allylamino-4-benzylamino-6-nitroquinazoline

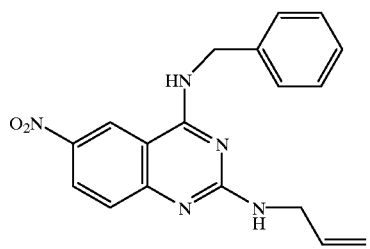

To 367 mg (1.77 mmol) of 6-nitroquinazoline-2,4 (1H, 3H)-dione was added 15.13 g (98.70 mmol) of phosphorus oxychloride to effect reaction in the same manner as in Example 10. Next, to the reaction mixture was added dropwise 379 mg (3.54 mmol) of benzylamine under ice cooling, and the resulting mixture was stirred under ice cooling for 2 hours. Water was added to the reaction mixture, and crystals thus precipitated were filtered out to obtain 2-chloro-4-benzylamino-6-nitroquinazoline. To this was added 761 mg (13.33 mmol) of allylamine, and the resulting mixture was stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 224 mg (yield: 56.8%) of the title compound.

m.p.: 235 to 236° C.

NMR (δ, DMSO-d$_6$, 55° C.): 3.95–4.01 (2H, m), 4.72 (2H, d, J=6 Hz), 5.02 (1H, d, J=10 Hz), 5.14 (1H, d, J=17 Hz), 5.83–5.96 (1H, m), 7.24–7.41 (7H, m), 8.20 (1H, dd, J=9 Hz, 3 Hz), 8.99 (1H, br), 9.12 (1H, d, J=3 Hz)

Mass (m/z, %): 335 (M$^+$, 70), 320 (100), 274 (16), 244 (11), 198 (15), 91 (65)

IR (ν, cm$^{-1}$), KBr: 3420, 3256, 1584, 1558, 1480, 1306, 1250, 832

Example 13

2-Allylamino-6-nitro-4-piperidinoquinazoline

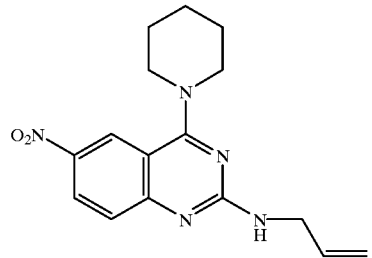

To 367 mg (1.77 mmol) of 6-nitroquinazoline-2,4 (1H, 3H)-dione was added 15.13 g (98.70 mmol) of phosphorus oxychloride to effect reaction in the same manner as in Example 10. Next, to the reaction mixture was added dropwise 301 mg (3.54 mmol) of piperidine under ice cooling, and the resulting mixture was stirred under ice cooling for 2 hours. Water was added to the reaction mixture, and crystals thus precipitated were filtered out to obtain 2-chloro-6-nitro-4-piperidinoquinazoline. The compound was dissolved in 1 ml of DMF, and after 1.52 g (26.65 mmol) of allylamine was added to the resulting solution, the resulting mixture was stirred at room temperature for 2.5 hours. Water was added to the reaction mixture, followed by extraction with ethyl acetate, washing with brine and drying over anhydrous sodium sulfate. After the solvent was distilled off, the residue was purified by a silica gel column to give 213 mg (yield: 38.4%) of the title compound.

m.p.: 123 to 124° C.

NMR (δ, CDCl$_3$, 45° C.): 1.79 (6H, br), 3.74 (4H, br), 4.13–4.18 (2H, m), 5.15 (1H, d with fine couple, J=10 Hz), 5.27 (1H, d with fine couple, J=17 Hz), 5.33 (1H, br), 5.91–6.04 (1H, m), 7.43 (1H, d, J=9 Hz), 8.25 (1H, dd, J=9 Hz, 3 Hz), 8.66 (1H, d, J=3 Hz)

Mass (m/z, %): 313 (M$^+$, 49), 298 (100), 283 (27), 268 (41), 252 (15)

IR (ν, cm$^{-1}$), KBr: 3260, 2944, 1580, 1484, 1322, 1120, 838

Example 14

2,4-Diallylamino-6-aminoquinazoline

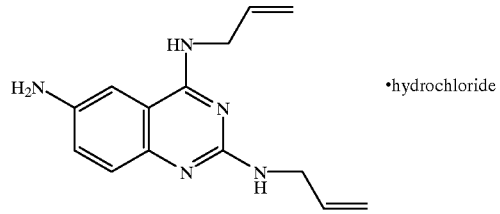

To 3.32 g (14.73 mmol) of tin (II) chloride dihydrate was added 14 ml of concentrated hydrochloric acid and 1.40 g (4.91 mmol) of 2,4-diallylamino-6-nitroquinazoline under ice cooling, and the resulting mixture was stirred at room temperature overnight. The reaction mixture was neutralized by adding an aqueous sodium hydroxide solution, followed by extraction with chloroform, washing with brine and drying over anhydrous sodium sulfate. After the solvent was distilled off, the residue was purified by a silica gel column to give 1.61 g (yield: 92.5%) of a free base compound of the title compound.

NMR (δ, CDCl$_3$): 3.65 (2H, br), 4.12 (2H, t, J=6 Hz), 4.22 (2H, t, J=6 Hz), 4.89 (1H, br), 5.09–5.32 (4H, m), 5.43 (1H, br), 5.93–6.08 (2H, m), 6.73 (1H, d, J=3 Hz), 7.02 (1H, dd, J=9 Hz, 3 Hz), 7.34 (1H, d, J=9 Hz)

EI-Mass (m/z, %): 255 (M$^+$, 73), 240 (100), 214 (14)

IR (ν, cm$^{-1}$), KBr: 3256, 1578, 1548, 1494, 1414, 1252, 840

To a solution of 650 mg (2.55 mmol) of the free base compound of the title compound in ethyl acetate was added dropwise a 4N hydrochloric acid-ethyl acetate solution under ice cooling. Crystals thus precipitated were filtered out to give 615 mg (82.8%) of the title compound.

m.p.: 212 to 215° C.

NMR (δ, DMSO-d$_6$, 55° C.): 4.05–4.07 (2H, m), 4.18 (2H, t, J=6 Hz), 5.12–5.27 (4H, m), 5.32 (2H, s), 5.88–6.01 (2H, m), 7.15 (1H, dd, J=9 Hz, 2 Hz), 7.24 (1H, d, J=2 Hz), 7.30 (1H, d, J=9 Hz), 7.93 (1H, br), 9.31 (1H, brs), 12.27 (1H, br)

EI-Mass (m/z, %): 255 (M$^+$, 64), 240 (100), 214 (15)

IR (ν, cm$^{-1}$), KBr: 3268, 1648, 1580, 1416, 1338, 922

Example 15

4-Allylamino-2-diallylamino-6-chloroquinazoline

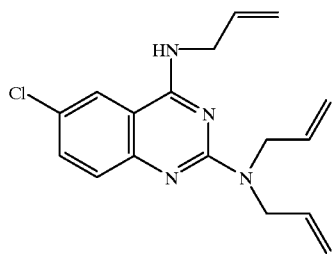

In a sealed tube were stirred 268 mg (1.06 mmol) of 4-allylamino-2,6-dichloronitroquinazoline and 787 mg (8.10 mmol) of diallylamine at 120° C. for 3 hours. Water was added to the reaction mixture, followed by extraction with ethyl acetate, washing with brine and drying over anhydrous sodium sulfate. After the solvent was distilled off, the residue was purified by silica gel column to give 284 mg (yield: 85.1%) of the title compound.

m.p.: 73 to 74° C.

NMR (δ, CDCl$_3$): 4.18–4.23 (2H, m), 4.30 (4H, d, J=6 Hz), 5.11–5.32 (6H, m), 5.40 (1H, br), 5.83–6.07 (3H, m), 7.37–7.44 (3H, m)

EI-Mass (m/z, %): 314 (M$^+$, 34), 273 (100), 260 (42)

IR (ν, cm$^{-1}$), KBr: 3288, 1572, 1502, 1414, 1248, 924

Example 16

4-Allylamino-2-methylamino-6-nitroquinazoline

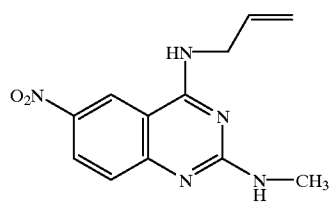

A mixture of 230 mg (0.87 mmol) of 4-allylamino-2-chloro-6-nitroquinazoline and 902 mg (12.88 mmol) of a 40% aqueous methylamine solution was stirred at room temperature for 30 minutes. Water was added to the reaction mixture, followed by extraction with ethyl acetate, washing with brine and drying over anhydrous sodium sulfate. After the solvent was distilled off, the residue was purified by a silica gel column to give 190 mg (yield: 84.2%) of the title compound.

m.p.: 238 to 239° C.

NMR (δ, DMSO-d$_6$, 55° C.): 2.88 (3H, d, J=4 Hz), 4.11–4.17 (2H, m), 5.13 (1H, d with fine couple, J=10 Hz), 5.24 (1H, d, J=17 Hz), 5.94–6.04 (1H, m), 7.07 (1H, br), 7.28 (1H, d, J=9 Hz), 8.20 (1H, dd, J=9 Hz, 2 Hz), 8.57 (1H, br), 9.10 (1H, d, J=2 Hz)

EI-Mass (m/z, %): 259 (M$^+$, 100), 244 (71), 198 (16)

IR (ν, cm$^{-1}$), KBr: 3412, 3264, 1614, 1552, 1484, 1310, 1178, 836

Example 17

4-Allylamino-2-ethylamino-6-nitroquinazoline

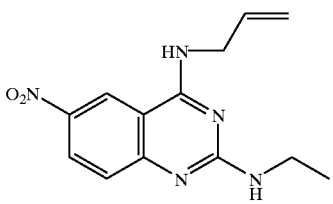

A mixture of 250 mg (0.95 mmol) of 4-allylamino-2-chloro-6-nitroquinazoline and 796 mg (15.52 mmol) of a 70% aqueous ethylamine solution was stirred at room temperature for 3 hours. Water. was added to the reaction mixture, followed by extraction with ethyl acetate, washing with brine and drying over anhydrous sodium sulfate. After the solvent was distilled off, the residue was purified by a silica gel column to give 234 mg (yield: 90.6%) of the title compound.

m.p.: 227 to 228° C.

NMR (δ, CDCl$_3$, 55° C.): 1.27 (3H, t, J=7 Hz), 3.53–3.59 (2H, m), 4.25 (2H, t, J=6 Hz), 5.20 (1H, br), 5.25 (1H, d with fine couple, J=10 Hz), 5.33 (1H, d with fine couple, J=17 Hz), 5.74 (1H, br), 5.97–6.07 (1H, m), 7.39 (1H, d, J=9 Hz), 8.28 (1H, dd, J=9 Hz, 2 Hz), 8.49 (1H, d, J=2 Hz)

EI-Mass (m/z, %): 273 (M$^+$, 100), 258 (65), 230 (64), 212 (24)

IR (ν, cm$^{-1}$), KBr: 3420, 3260, 1594, 1560, 1486, 1300, 1172, 834

Example 18

4-Allylamino-2-isopropylamino-6-nitroquinazoline

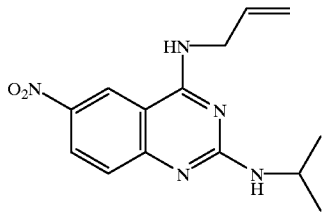

A mixture of 250 mg (0.95 mmol) of 4-allylamino-2-chloro-6-nitroquinazoline and 694 mg (11.74 mmol) of isopropylamine was stirred at room temperature for 3 hours. Water was added to the reaction mixture, and crystals thus precipitated were filtered to give 270 mg (yield: 99.4%) of the title compound.

m.p.: 150 to 151° C.

NMR (δ, CDCl$_3$, 55° C.): 1.27 (6H, d, J=6 Hz), 4.25–4.33 (3H, m), 5.09 (1H, br), 5.25 (1H, d with fine couple, J=10 Hz), 5.33 (1H, d with fine couple, J=17 Hz), 5.77 (1H, br), 5.97–6.07 (1H, m), 7.37 (1H, d, J=8 Hz), 8.27 (1H, dd, J=8 Hz, 2 Hz), 8.50 (1H, d, J=2 Hz)

EI-Mass (m/z, %): 287 (M$^+$, 89), 272 (100), 245 (37), 230 (55), 226 (39)

IR (ν, cm$^{-1}$), KBr: 3436, 2976, 1588, 1546, 1480, 1306, 1176, 838

Example 19

4-Allylamino-2-t-butylamino-6-nitroquinazoline

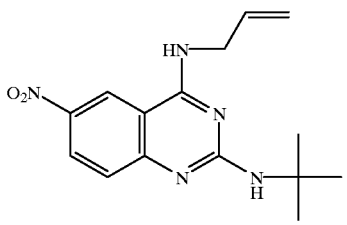

At 80° C. were stirred 225 mg (0.85 mmol) of 4-allylamino-2-chloro-6-nitroquinazoline and 696 mg (9.52 mmol) of t-butylamine overnight. Water was added to the reaction mixture, followed by extraction with ethyl acetate, washing with brine and drying over anhydrous sodium sulfate. After the solvent was distilled off, the residue was purified by a silica gel column to give 240 mg (yield: 93.7%) of the title compound.

m.p.: 139 to 140° C.

NMR (δ, CDCl$_3$, 55° C.): 1.51 (9H, s), 4.26 (2H, t, J=6 Hz), 5.26 (1H, d with fine couple, J=10 Hz), 5.33 (1H, d with fine couple, J=17 Hz), 5.35 (1H, br), 5.73 (1H, br), 5.97–6.07 (1H, m), 7.35 (1H, d, J=9 Hz), 8.27 (1H, dd, J=9 Hz, 2 Hz), 8.50 (1H, d, J=2 Hz)

EI-Mass (m/z, %): 301 (M$^+$, 44), 286 (100), 245 (90), 230 (49)

IR (ν, cm$^{-1}$), KBr: 3424, 2976, 1582, 1548, 1504, 1320, 842

Example 20

4-Allylamino-2-(2-aminoethylamino)-6-nitroquinazoline

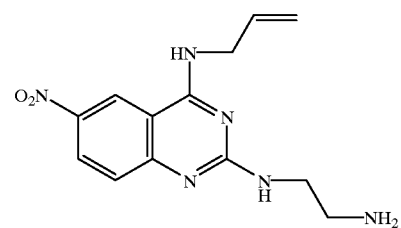

A mixture of 230 mg (0.87 mmol) of 4-allylamino-2-chloro-6-nitroquinazoline and 899 mg (14.96 mmol) of ethylenediamine was stirred at room temperature for 2 hours. Water was added to the reaction mixture, followed by extraction with ethyl acetate, washing with brine and drying over anhydrous sodium sulfate. After the solvent was distilled off, the residue was purified by a silica gel column to give 200 mg (yield: 79.9%) of the title compound.

m.p.: 126 to 128° C.

NMR (δ, DMSO-d$_6$, 55° C.): 1.36 (2H, br), 2.70–2.74 (2H, m), 3.34–3.38 (2H, m), 4.14 (2H, t, J=5 Hz), 5.11–5.27 (2H, m), 5.94–6.04 (1H, m), 7.06 (1H, br), 7.25 (1H, br), 8.19 (1H, dd, J=9 Hz, 3 Hz), 8.60 (1H, br), 9.09 (1H, d, J=3 Hz)

EI-Mass (m/z, %): 288 (M$^+$, 10), 258 (57), 246 (100), 212 (44)

IR (ν, cm$^{-1}$), KBr: 3420, 3260, 1590, 1554, 1488, 1306, 1166, 924

Example 21

2-Allylamino-4-methylamino-6-nitroquinazoline

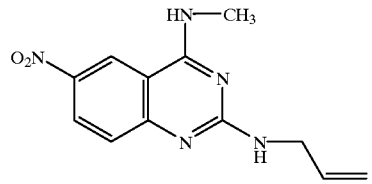

To 311 mg (1.50 mmol) of 6-nitroquinazoline-2,4 (1H, 3H)-dione was added 12.83 g (83.47 mmol) of phosphorus oxychloride to effect reaction in the same manner as in Example 10. Next, to the reaction mixture was added dropwise 208 mg (3.00 mmol) of a 40% aqueous methylamine solution under ice cooling, and the resulting mixture was stirred under ice cooling for 2 hours. Water was added to the reaction mixture, followed by extraction with ethyl acetate, washing with brine and drying over anhydrous sodium sulfate. The solvent was distilled off to obtain 2-chloro-4-methylamino-6-nitroquinazoline. To the compound thus obtained was added 761 mg (13.33 mmol) of allylamine, and the resulting mixture was stirred at room temperature for 3 hours. Water was added to the reaction mixture, followed by extraction with ethyl acetate, washing with brine and drying over anhydrous sodium sulfate. After the solvent was distilled off, the residue was purified by a silica gel column to give 158 mg (yield: 40.7%) of the title compound.

m.p.: 211 to 212° C.

NMR (δ, CDCl$_3$, 55° C.): 3.16 (3H, d, J=5 Hz), 4.18–4.21 (2H, m), 5.14–5.31 (3H, m), 5.77 (1H, br), 5.94–6.04 (1H, m), 7.41 (1H, d, J=9 Hz), 8.28 (1H, dd, J=9 Hz, 2 Hz), 8.49 (1H, d, J=2 Hz)

EI-Mass (m/z, %): 259 (M$^+$, 67), 244 (100), 198 (41)

IR (ν, cm$^{-1}$), KBr: 3444, 3252, 1588, 1562, 1480, 1312, 1100, 834

Example 22

2-Allylamino-4-ethylamino-6-nitroquinazoline

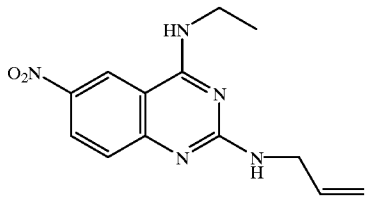

To 311 mg (1.50 mmol) of 6-nitroquinazoline-2,4 (1H, 3H)-dione was added 12.80 g (83.47 mmol) of phosphorus oxychloride to effect reaction in the same manner as in Example 10. Next, to the reaction mixture was added dropwise 151 mg (3.00 mmol) of a 70% aqueous ethylamine solution under ice cooling, and the resulting mixture was stirred under ice cooling for 2 hours. Water was added to the reaction mixture, followed by extraction with ethyl acetate, washing with brine and drying over anhydrous sodium sulfate. The solvent was distilled off to obtain 2-chloro-4-ethylamino-6-niroquinazoline. To the compound thus obtained was added 761 mg (13.33 mmol) of allylamine, and the resulting mixture was stirred at room temperature for 3 hours. Water was added to the reaction mixture, followed by extraction with ethyl acetate, washing with brine and drying over anhydrous sodium sulfate. After the solvent was distilled off, the residue was purified by a silica gel column to give 180 mg (yield: 44.1%) of the title compound.

m.p.: 215 to 216° C.

NMR (δ, CDCl$_3$, 55° C.): 1.35 (3H, t, J=7 Hz), 3.62–3.69 (2H, m), 4.16–4.20 (2H, m), 5.14–5.30 (3H, m), 5.68 (1H, br), 5.94–6.03 (1H, m), 7.40 (1H, d, J=9 Hz), 8.28 (1H, dd, J=9 Hz, 2 Hz), 8.48 (1H, d, J=2 Hz)

EI-Mass (m/z, %): 273 (M$^+$, 61), 258 (100), 212 (30)

IR (ν, cm$^{-1}$), KBr: 3416, 3264, 1590, 1554, 1486, 1306, 1102, 834

Reference Example 4

2-Chloro-4-trans-cinnamylamino-6-nitroquinazoline

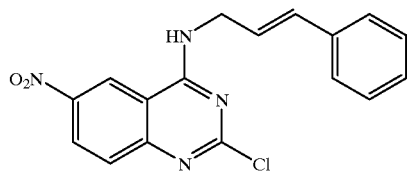

To 400 mg (1.93 mmol) of 6-nitroquinazoline-2,4 (1H, 3H)-dione were added 1 ml of 1,3-dimethyl-2-imidazolidinone and 2.96 g (19.3 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 5.94 ml (42.46 mmol) of triethylamine and 514 mg (3.86 mmol) of trans-cinnamylamine hydrochloride and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 85 mg (yield: 13.0%) of the title compound.

NMR (δ, CDCl$_3$); 4.43–4.46 (2H, m), 6.35–6.42 (1H, m), 6.67 (1H, d, J=16 Hz), 7.24–7.42 (5H, m), 7.77 (1H, d, J=9 Hz), 8.45 (1H, dd, J=9 Hz, 2 Hz), 9.11 (1H, br), 9.44 (1H, d, J=2 Hz)

Example 23

2-Allylamino-4-trans-cinnamylamino-6-nitroquinazoline hydrochloride

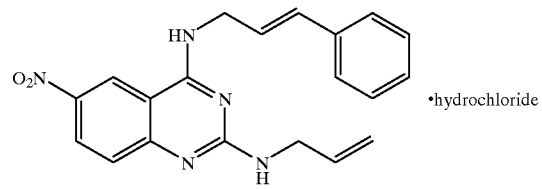

To 75 mg (0.22 mmol) of 2-chloro-4-trans-cinnamylamino-6-nitroquinazoline was added 761 mg (13.33 mmol) of allylamine, followed by stirring at room temperature overnight. To the reaction solution was water added, followed by extraction with ethyl acetate, washing with brine and drying over anhydrous sodium sulfate. After the solvent was distilled off and the residue was purified by a silica gel column, a 4N hydrochloric acid-ethyl acetate solution was added thereto, and then crystals thus precipitated were filtered to give 57 mg (yield: 65.1%) of the title compound.

NMR (δ, DMSO-d$_6$ 55° C.): 4.16 (2H, t, J=6 Hz), 4.40 (2H, t, J=5 Hz), 5.15 (1H, d, J=10 Hz), 5.30 (1H, d, J=17 Hz), 5.91–6.00 (1H, m), 6.37–6.44 (1H, m), 6.69 (1H, d, J=16 Hz), 7.23–7.65 (6H, m), 8.50 (1H, br), 8.52 (1H, d, J=9 Hz), 9.34 (1H, s), 10.22 (1H, br), 13.11 (1H, br)

EI-Mass (m/z, %): 361 (M$^+$, 100), 346 (53), 117 (59)

IR (ν, cm$^{-1}$), KBr: 3386, 2595, 1655, 1594, 1491, 1335, 845 m.p.: 206 to 208° C.

Reference Example 5

4-Butylamino-2-chloro-6-nitroquinazoline

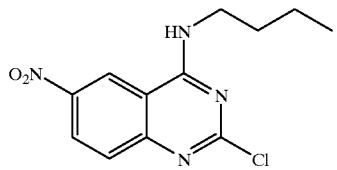

To 500 mg (2.41 mmol) of 6-nitroquinazoline-2,4 (1H, 3H)-dione were added 2 ml of 1,3-dimethyl-2-imidazolidinone and 8.23 g (53.64 mmol) of phosphorus oxychloride, and the resulting mixture was subjected to heating under reflux for 3 hours. After phosphorus oxychloride was removed in vacuo, the mixture was dissolved in 5 ml of acetonitrile, followed by addition of 5.9 ml (60 mmol) of butylamine and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 430 mg (yield: 63.6%) of the title compound.

NMR (δ, CDCl$_3$,): 1.02 (3H, t), 1.45–1.55 (2H, m), 1.73–1.81 (2H, m), 3.72–3.77 (2H, m), 6.30 (1H, br), 7.86 (1H, d, J=9 Hz), 8.51 (1H, dd, J=9 Hz, 2 Hz), 8.72 (1H, d, J=2 Hz)

Example 24

2-Allylamino-4-butylamino-6-nitroquinazoline

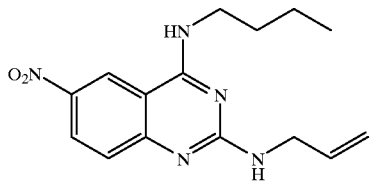

To 170 mg (0.67 mmol) of 4-butylamino-2-chloro-6-nitroquinazoline was added 1.52 g (26.66 mmol) of allylamine, followed by stirring at room temperature overnight. To the reaction solution was water added, followed by extraction with ethyl acetate, washing with brine and drying over anhydrous sodium sulfate. After the solvent was distilled off, the residue was purified by a silica gel column to give 166 mg (yield: 82.1%) of the title compound.

NMR (δ, CDCl$_3$, 55° C.): 1.00 (3H, t, J=7 Hz), 1.44–1.51 (2H, m), 1.68–1.73 (2H, m), 3.59–3.64 (2H, m), 4.16–4.19 (2H, m), 5.14–5.30 (3H, m), 5.70 (1H, br), 5.94–6.03 (1H, m), 7.39 (1H, d, J=9 Hz), 8.28 (1H, dd, J=9 Hz, 2 Hz), 8.47 (1H, d, J=2 Hz)

EI-Mass (m/z, %): 301 (M$^+$, 49), 286 (100)

IR (ν, cm$^{-1}$), KBr: 3392, 2935, 1606, 1558, 1481, 1302, 831 m.p.: 214 to 215° C.

Reference Example 6

2-Chloro-6-nitro-4-pentylaminoquinazoline

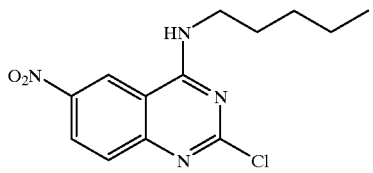

To 400 mg (1.93 mmol) of 6-nitroquinazoline-2,4 (1H, 3H)-dione were added 1 ml of 1,3-dimethyl-2-imidazolidinone and 6.58 g (42.91 mmol) of phosphorus oxychloride, and the resulting mixture was subjected to heating under reflux for 3 hours. After phosphorus oxychloride was removed in vacuo, the mixture was dissolved in 4 ml of acetonitrile, followed by addition of 5.60 ml (48.25 mmol) of propylamine and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 342 mg (yield: 70.1%) of the title compound.

NMR (δ, CDCl$_3$): 0.94–0.97 (3H, m), 1.41–1.47 (4H, m), 1.75–1.81 (2H, m), 3.71–3.76 (2H, m), 6.25 (1H, br), 7.86 (1H, d, J=9 Hz), 8.51 (1H, dd, J=9 Hz, 2 Hz), 8.70 (1H, d, J=2 Hz)

Example 25

2-Allylamino-6-nitro-4-pentylaminoquinazoline hydrochloride

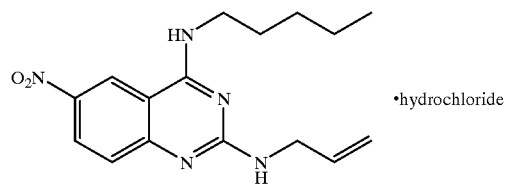

To 170 mg (0.61 mmol) of 2-chloro-6-nitro-4-pentylaminoquinazoline was added 1.52 g (26.66 mmol) of allylamine, followed by stirring at room temperature overnight. To the reaction solution was water added, followed by extraction with ethyl acetate, washing with brine and drying over anhydrous sodium sulfate. After the solvent was distilled off, the residue was purified by a silica gel column to give 160 mg (yield: 83.6%) of a free base compound of the title compound.

NMR (δ, CDCl$_3$, 55° C.): 0.93–0.96 (3H, m), 1.39–1.46 (4H, m), 1.69–1.76 (2H, m), 3.58–3.63 (2H, m), 4.16–4.19 (2H, m), 5.14–5.30 (3H, m), 5.72 (1H, br), 5.94–6.03 (1H, m), 7.39 (1H, d, J=9 Hz), 8.27 (1H, dd, J=9 Hz, 2 Hz), 8.48 (1H, d, J=2 Hz)

EI-Mass (m/z, %): 315 (M$^+$, 42), 300 (100)

Under ice cooling, a 4N hydrochloric acid-ethyl acetate solution was added dropwise to a solution of 120 mg (0.38 mmol) of the free base compound of the title compound in ethyl acetate. Crystals thus precipitated were filtered to give 112 mg (yield: 83.8%) of the title compound.

NMR (δ, CDCl$_3$): 0.91–0.95 (3H, m), 1.35–1.46 (4H, m), 1.80–1.87 (2H, m), 3.74–3.79 (2H, m), 4.20 (2H, t, J=6 Hz), 5.19–5.36 (2H, m), 5.86–5.96 (1H, m), 7.58 (1H, d, J=9 Hz), 8.36 (1H, t, J=6 Hz), 8.38 (1H, dd, J=9 Hz, 2 Hz), 9.06 (1H, t, J=5 Hz), 9.45 (1H, d, J=2 Hz), 13.87 (1H, br)

IR (ν, cm$^{-1}$), KBr: 3435, 2931, 1655, 1610, 1425, 1338, 746 m.p.: 190 to 192° C.

Reference Example 7

2-Chloro-4-heptylamino-6-nitroquinazoline

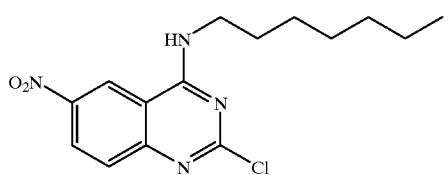

To 300 mg (1.45 mmol) of 6-nitroquinazoline-2,4 (1H, 3H)-dione were added 1 ml of 1,3-dimethyl-2- imidazolidinone and 2.22 g (14.48 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 5.38 ml (36.25 mmol) of heptylamine and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 247 mg (yield: 52.8%) of the title compound (yield: 52.8%).

NMR (δ, CDCl$_3$,): 0.89–0.92 (3H, m), 1.30–1.48 (8H, m), 1.74–1.81 (2H, m), 3.71–3.76 (2H, m), 6.20 (1H, br), 7.86 (1H, d, J=9 Hz), 8.51 (1H, dd, J=9 Hz, 2 Hz), 8.69 (1H, d, J=2 Hz)

Example 26

2-Allylamino-4-heptylamino-6-nitroquinazoline hydrochloride

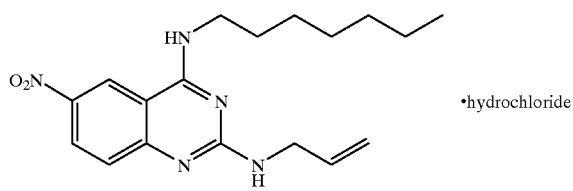
·hydrochloride

To 150 mg (0.46 mmol) of 2-chloro-4-heptylamino-6-nitroquinazoline was added 1.14 g (20.00 mmol) of allylamine, followed by stirring at room temperature overnight. To the reaction solution was water added, followed by extraction with ethyl acetate, washing with brine and drying over anhydrous sodium sulfate. After the solvent was distilled off, the residue was purified by a silica gel column to give 140 mg (yield: 88.6%) of a free compound base of the title compound.

NMR (δ, CDCl$_3$, 55° C.): 0.88–0.92 (3H, m), 1.26–1.47 (8H, m), 1.69–1.76 (2H, m), 3.58–3.63 (2H, m), 4.16–4.19 (2H, m), 5.14–5.30 (3H, m), 5.68 (1H, br), 5.94–6.03 (1H, m), 7.39 (1H, d, J=9 Hz), 8,28 (1H, dd, J=9 Hz, 3 Hz), 8.47 (1H, d, J=3 Hz)

EI-Mass (m/z, %): 343 (M$^+$, 40), 328 (100)

Under ice cooling, a 4N hydrochloric acid-ethyl acetate solution was added dropwise to a solution of 120 mg (0.35 mmol) of the free base compound of the title compound in ethyl acetate. Crystals thus precipitated were filtered to give 100 mg (yield: 75.2%) of the title compound.

NMR (δ, CDCl$_3$, 55° C.): 0.89 (3H, t, J=7 Hz), 1.26–1.51 (8H, m), 1.79–1.86 (2H, m), 3.73–3.78 (2H, m), 4.19 (2H, br), 5.20–5.37 (2H, m), 5.86–5.96 (1H, m), 7.63 (1H, d, J=9 Hz), 8.37–8.40 (2H, m), 8.51 (1H, br), 9.19 (1H, s), 14.19 (1H, br)

IR (ν, cm$^{-1}$), KBr: 3367, 2927, 1651, 1612, 1425, 1336, 748 m.p.: 186 to 188° C.

Reference Example 8

2-Chloro-4-cyclopentylamino-6-nitroquinazoline

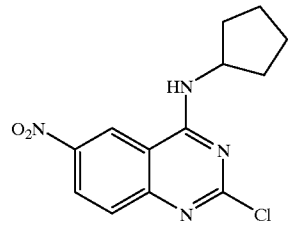

To 300 mg (1.45 mmol) of 6-nitroquinazoline-2,4 (1H, 3H)-dione were added 1 ml of 1,3-dimethyl-2-imidazolidinone and 1.23 g (8.05 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 4.05 ml (29.00 mmol) of triethylamine and 0.89 ml (8.70 mmol) of cyclopentylamine and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 152 mg (yield: 35.9%) of the title compound.

NMR (δ, CDCl$_3$): 1.58–1.90 (6H, m), 2.23–2.31 (2H, m), 4.66–4.74 (1H, m), 6.18 (1H, d, J=7 Hz), 7.85 (1H, d, J=9 Hz), 8.50 (1H, dd, J=9 Hz, 2 Hz), 8.68 (1H, d, J=2 Hz)

Example 27

2-Allylamino-4-cyclopentylamino-6-nitroquinazoline hydrochloride

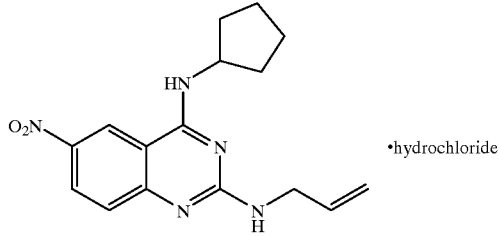
·hydrochloride

To 128 mg (0.44 mmol) of 2-chloro-4-cyclopentylamino-6-nitroquinazoline was added 913 mg (16.00 mmol) of allylamine, followed by stirring at room temperature for 3 hours. To the reaction solution was water added, followed by extraction with ethyl acetate, washing with brine and drying over anhydrous sodium sulfate. After the solvent was distilled off, the residue was purified by a silica gel column to give 129 mg (yield: 93.6%) of a free base compound of the title compound.

NMR (δ, CDCl$_3$, 55° C.): 1.54–1.86 (6H, m), 2.14–2.22 (2H, m), 4.16–4.19 (2H, m), 4.50–4.56 (1H, m), 5.14–5.30 (3H, m), 5.62 (1H, br), 5.94–6.04 (1H, m), 7.38 (1H, d, J=9 Hz), 8.27 (1H, dd, J=9 Hz, 3 Hz), 8.45 (1H, d, J=3 Hz)

EI-Mass (m/z, %): 313 (M$^+$, 49), 298 (100)

Under ice cooling, a 4N hydrochloric acid-ethyl acetate solution was added dropwise to a solution of 92 mg (0.29 mmol) of the free base compound of the title compound in ethyl acetate. Crystals thus precipitated were filtered to give 87 mg (yield: 85.8%) of the title compound.

NMR (δ, CDCl₃): 1.72–1.94 (6H, m), 2.17–2.24 (2H, m), 4.20 (2H, t, J=6 Hz), 4.64–4.71 (1H, m), 5.20–5.36 (2H, m), 5.86–5.96 (1H, m), 7.61 (1H, d, J=9 Hz), 8.21 (1H, d, J=7 Hz), 8.41 (1H, dd, J=9 Hz, 2 Hz), 8.49 (1H, t, J=6 Hz), 9.32 (1H, d, J=2 Hz), 14.13 (1H, br)

IR (ν, cm⁻¹), KBr: 3224, 2956, 1641, 1610, 1579, 1446, 1338, 748 m.p.: 208 to 210° C.

Reference Example 9

2-Chloro-4-isopropylamino-6-nitroquinazoline

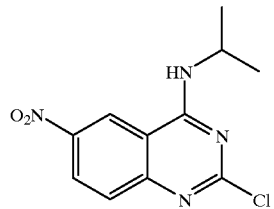

To 1.00 g (4.83 mmol) of 6-nitroquinazoline-2,4 (1H,3H)-dione were added 32.90 g (0.22 mol) of phosphorus oxychloride and 0.70 ml (4.83 mmol) of diisopropylformamide, and the resulting mixture was subjected to heating under reflux for 24 hours. After phosphorus oxychloride was removed in vacuo, the mixture was dissolved in 15 ml of acetonitrile, followed by addition of 2.49 ml (29.11 mmol) of isopropylamine under ice cooling and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 870 mg (yield: 67.5%) of the title compound.

NMR (δ, CDCl₃): 1.42 (6H, d, J=6 Hz), 4.62–4.70 (1H, m), 6.11 (1H, d, J=7 Hz), 7.85 (1H, d, J=9 Hz), 8.50 (1H, dd, J=9 Hz, 2 Hz), 8.71 (1H, d, J=2 Hz)

Example 28

2-Allylamino-4-isopropylamino-6-nitroquinazoline hydrochloride

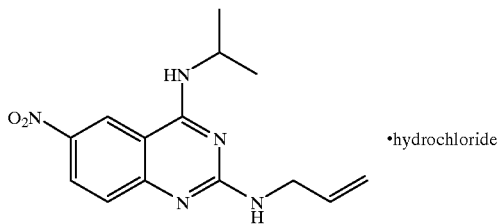

To 870 mg (3.26 mmol) of 2-chloro-4-isopropylamino-6-nitroquinazoline was added 3.81 g (66.64 mmol) of allylamine, followed by stirring at room temperature for 4 hours. To the reaction solution was added water, followed by extraction with ethyl acetate, washing with brine and drying over anhydrous sodium sulfate. After the solvent was distilled off, the residue was purified by a silica gel column to give 895 mg (yield: 95.7%) of a free base compound of the title compound.

NMR (δ, CDCl₃, 55° C.): 1.35 (6H, d, J=7 Hz), 4.15–4.19 (2H, m), 4.44–4.52 (1H, m), 5.14–5.30 (3H, m), 5.48 (1H, br), 5.94–6.03 (1H, m), 7.39 (1H, d, J=9 Hz), 8.27 (1H, dd, J=9 Hz, 2 Hz), 8.46 (1H, d, J=2 Hz)

EI-Mass (m/z, %): 287 (M⁺, 43), 272 (100), 230 (15), 226 (18)

IR (ν, cm⁻¹), KBr: 3256, 3096, 1590, 1588, 1488, 1306, 1166, 924

Under ice cooling, a 4N hydrochloric acid-ethyl acetate solution was added dropwise to a solution of 510 mg (1.78 mmol) of the free base compound of the title compound in ethyl acetate. Crystals thus precipitated were filtered to give 536 mg (yield: 93.0%) of the title compound.

NMR (δ, CDCl₃): 1.50 (6H, d, J=7 Hz), 4.18–4.21 (2H, m), 4.62–4.71 (1H, m), 5.19–5.36 (2H, m), 5.86–5.95 (1H, m), 7.60 (1H, d, J=9 Hz), 8.40 (1H, dd, J=9 Hz, 2 Hz), 8.43 (1H, t, J=6 Hz), 8.59 (1H, d, J=8 Hz), 9.50 (1H, d, J=2 Hz), 13.97 (1H, br s)

IR (ν, cm⁻¹), KBr: 3244, 1649, 1583, 1527, 1342, 839 m.p.: 211 to 213° C.

Example 29

4-Allylamino-6-nitro-2-(2-propynylamino) quinazoline

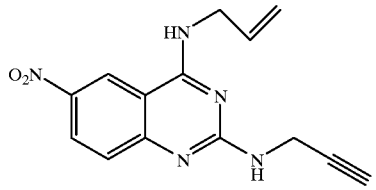

To 150 mg (0.57 mmol) of 4-allylamino-2-chloro-6-nitroquinazoline was added 1.61 g (29.16 mmol) of 2-propynylamine, followed by stirring at room temperature for 6 hours. After water was added to the reaction solution was water added, crystals thus precipitated were filtered and recrystallized from ethyl acetate-hexane to give 143 mg (yield: 88.6%) of the title compound.

NMR (δ, DMSO-d₆, 55° C.): 2.94 (1H, t, J=2 Hz), 4.14–4.16 (4H, m), 5.12–5.28 (2H, m), 5.96–6.05 (1H, m), 7.32 (1H, d, J=9 Hz), 7.46 (1H, br), 8.23 (1H, dd, J=9 Hz, 3 Hz), 8.74 (1H, br), 9.13 (1H, d, J=3 Hz)

EI-Mass (m/z, %): 283 (M⁺, 98), 282 (100), 236 (34), 196 (53)

IR (ν, cm⁻¹), KBr: 3394, 3296, 1610, 1560, 1477, 1317, 837 m.p.: 192 to 193° C.

Example 30

4-Allylamino-2-(trans-2-butenylamino)-6-nitroquinazoline

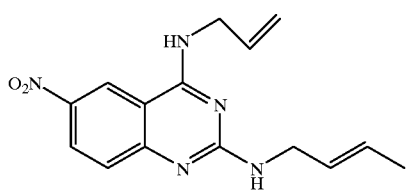

150 mg (0.57 mmol) of 4-allylamino-2-chloro-6-nitroquinazoline was dissolved in 2 ml of acetonitrile, and 305 mg (2.83 mmol) of trans-2-butenylamine hydrochloride and 0.39 ml (2.83 mmol) of triethylamine were added thereto, followed by stirring at 50° C. for 6 hours. To the reaction solution was water added, followed by extraction with ethyl acetate, washing with brine and drying over anhydrous sodium sulfate. After the solvent was distilled off, the residue was purified by a silica gel column to give 138 mg (yield: 80.9%) of the title compound.

NMR (δ, CDCl₃): 1.71 (2H, d, J=6 Hz), 1.75 (1H, d, J=7 Hz), 4.09 (1.3H, t, J=6 Hz), 4.18 (0.7H, t, J=6 Hz), 4.26 (2H, br), 5.15–5.36 (3H, m), 5.47–6.06 (4H, m), 7.43 (1H, br), 8.30 (1H, dd, J=9 Hz, 2 Hz), 8.51 (1H, d, J=2 Hz)

EI-Mass (m/z, %): 299 (M⁺, 54), 284 (34), 270 (100)

IR (ν, cm⁻¹), KBr: 3386, 3263, 1606, 1551, 1481, 1308, 833 m.p.: 188 to 189° C.

Example 31

4-Allylamino-2-butylamino-6-nitroquinazoline hydrochloride

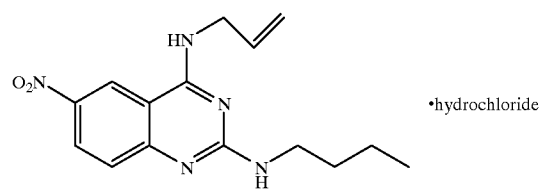

A mixture of 250 mg (0.95 mmol) of 4-allylamino-2-chloro-6-nitroquinazoline and 740 mg (10.02 mmol) of butylamine was stirred at room temperature for 3 hours. After water was added to the reaction solution, crystals thus precipitated were filtered, followed by recrystallization from ethyl acetate-hexane to give 249 mg (87.4%) of a free base compound of the title compound.

NMR (δ, CDCl₃, 55° C.): 0.97 (3H, t, J=7 Hz), 1.40–1.49 (2H, m), 1.59–1.66 (2H, m), 3.50–3.55 (2H, m), 4.25 (2H, t, J=6 Hz), 5.20 (1H, br), 5.23–5.36 (2H, m), 5.73 (1H, br), 5.97–6.07 (1H, m), 7.39 (1H, d, J=9 Hz), 8.27 (1H, dd, J=9 Hz, 2 Hz), 8.49 (1H, d, J=2 Hz)

EI-Mass (m/z, %): 301 (M⁺, 84), 272 (65), 259 (100), 258 (88), 245 (66), 230 (58), 212 (53)

IR (ν, cm⁻¹), KBr: 3428, 3256, 1586, 1556, 1482, 1306, 1172

Under ice cooling, a 4N hydrochloric acid-ethyl acetate solution was added dropwise to a solution of 124 mg (0.41 mmol) of the free base compound of the title compound in ethyl acetate. Crystals thus precipitated were filtered to give 120 mg (86.6%) of the title compound.

NMR (δ, CDCl₃): 0.94 (3H, t, J=7 Hz), 1.39–1.48 (2H, m), 1.62–1.71 (2H, m), 3.55–3.60 (2H, m), 4.39 (2H, t, J=6 Hz), 5.25–5.39 (2H, m), 5.99–6.09 (1H, m), 7.54 (1H, d, J=9 Hz), 8.25 (1H, t, J=6 Hz), 8.37 (1H, dd, J=9 Hz, 2 Hz), 9.54 (1H, t, J=6 Hz), 9.57 (1H, d, J=2 Hz), 13.59 (1H, br s)

IR (ν, cm⁻¹), KBr: 3437, 3078, 1612, 1585, 1425, 1338, 744 m.p.: 210 to 212° C.

Example 32

4-Allylamino-6-nitro-2-(2-thenylamino)quinazoline hydrochloride

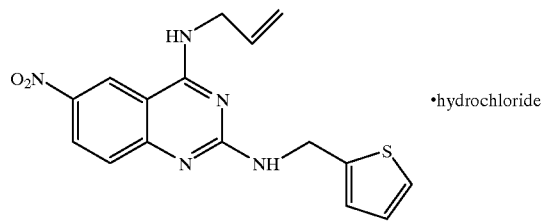

A mixture of 200 mg (0.76 mmol) of 4-allylamino-2-chloro-6-nitroquinazoline and 2.20 g (19.44 mmol) of 2-thenylamine was stirred at room temperature for 4 hours. Water was added to the reaction solution, followed by extraction with chloroform, washing brine and drying over anhydrous sodium sulfate. The solvent was distilled off, followed by recrystallization from ethyl acetate-hexane to give 241 mg (93.4%) of a free base compound of the title compound.

NMR (δ, DMSO-d₆, 55° C.): 4.16 (2H, br), 4.72 (2H, d, J=6 Hz), 5.10–5.26 (2H, m), 5.93–6.03 (1H, m), 6.93 (1H, dd, J=5 Hz, 3 Hz), 7.01 (1H, d, J=3 Hz), 7.25–7.35 (2H, m), 7.75 (1H, br), 8.22 (1H, dd, J=9 Hz, 2 Hz), 8.69 (1H, br), 9.12 (1H, d, J=2 Hz)

EI-Mass (m/z, %): 341 (M⁺, 100), 311 (58), 300 (33), 254 (20), 97 (52)

Under ice cooling, a 4N hydrochloric acid/ethyl acetate solution was added dropwise to a solution of 100 mg (0.29 mmol) of the free base compound of the title compound in ethyl acetate. Crystals thus precipitated were filtered to give 87 mg (yield: 79.4%) of the title compound.

NMR (δ, DMSO-d₆, 55° C.): 4.30 (2H, br), 4.89 (2H, br), 5.19–5.33 (2H, m), 5.94–6.04 (1H, m), 6.99 (1H, dd, J=5 Hz, 4 Hz), 7.12 (1H, br), 7.42 (1H, d, J=5 Hz), 7.68 (1H, d, J=9 Hz), 8.52 (1H, d, J=9 Hz), 8.88 (1H, br), 9.36 (1H, s), 10.24 (1H, br), 13.59 (1H, br)

IR (ν, cm⁻¹), KBr: 3246, 2723, 1651, 1589, 1525, 1335, 845 m.p.: 228 to 233° C. (decomp)

Example 33

4-Allylamino-2-furfurylamino-6-nitroquinazoline hydrochloride

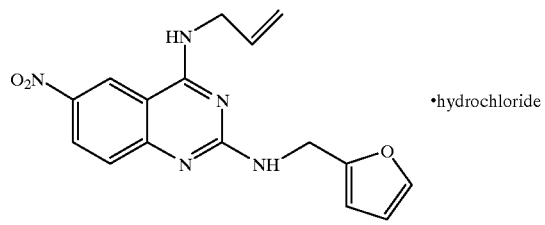

A mixture of 250 mg (0.95 mmol) of 4-allylamino-2-chloro-6-nitroquinazoline and 1.10 g (11.33 mmol) of furfurylamine was stirred at room temperature for 3 hours. After water was added to the reaction solution, crystals thus precipitated were filtered to give 234 mg (95.1%) of the free base compound of the title compound.

NMR (δ, CDCl₃, 55° C.): 4.26 (2H, t, J=6 Hz), 4.73 (2H, d, J=6 Hz), 5.25–5.33 (2H, m), 5.48 (1H, br), 5.77 (1H, br), 5.96–6.04 (1H, m), 6.26 (1H, d, J=3 Hz), 6.32 (1H, dd, J=3 Hz, 2 Hz), 7.36 (1H, d, J=2 Hz), 7.44 (1H, d, J=9 Hz), 8.30 (1H, dd, J=9 Hz, 3 Hz), 8.51 (1H, d, J=3 Hz)

EI-Mass (m/z, %): 325 (M⁺, 100), 295 (16), 284 (12), 238 (13), 81 (20)

IR (ν, cm⁻¹), KBr: 3428, 3252, 1586, 1560, 1480, 1306, 1102, 748 m.p.: 217 to 218° C.

Under ice cooling, a 4N hydrochloric acid-ethyl acetate solution was added dropwise to a solution of 100 mg (0.31 mmol) of the free base compound of the title compound in ethyl acetate. Crystals thus precipitated were filtered to give 90 mg (yield: 80.3%) of the title compound.

NMR (δ, DMSO-d₆, 55° C.): 4.27 (2H, br), 4.73 (2H, br), 5.19–5.34 (2H, m), 5.94–6.04 (1H, m), 6.40 (1H, br), 6.42 (1H, dd, J=3 Hz, 2 Hz), 7.60 (1H, d, J=2 Hz), 7.68 (1H, d, J=9 Hz), 8.54 (1H, d, J=9 Hz), 8.81 (1H, br), 9.38 (1H, s), 10.30 (1H, br), 13.72 (1H, br)

IR (ν, cm⁻¹), KBr: 3350, 2725, 1651, 1587, 1527, 1450, 1335, 845 m.p.: 222 to 226° C. (decomp)

Example 34

4-Allylamino-2-cyclopentylamino-6-nitroquinazoline hydrochloride

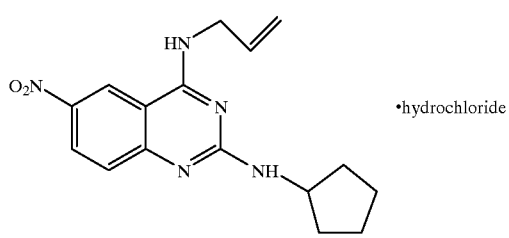

A mixture of 250 mg (0.95 mmol) of 4-allylamino-2-chloro-6-nitroquinazoline and 1.73 g (20.32 mmol) of cyclopentylamine was stirred at room temperature for 3 hours. After water was added to the reaction solution crystals thus precipitated were filtered out to give 232 mg (97.9%) of the free base compound of the title compound.

NMR (δ, CDCl₃, 55° C.): 1.49–1.80 (6H, m), 2.05–2.12 (2H, m), 4.25 (2H, t, J=5 Hz), 4.41–4.46 (1H, m), 5.22 (1H, br), 5.24–5.36 (2H, m), 5.72 (1H, br), 5.97–6.07 1H, m), 7.38 (1H, d, J=8 Hz), 8.27 (1H, dd, J=8 Hz, 2 Hz), 8.48 (1H, d, J=2 Hz)

Mass (m/z, %): 313 (M⁺, 48), 272 (37), 245 (100), 230 (55)

Under ice cooling, a 4N hydrochloric acid-ethyl acetate solution was added dropwise to a solution of 100 g (0.32 mmol) of the free base compound of the title compound in ethyl acetate. Crystals thus precipitated were filtered to give 102 mg (yield: 91.2%) of the title compound.

NMR (δ, CDCl₃): 1.63–1.86 (6H, m), 2.02–2.10 (2H, m), 4.36–4.44 (3H, m), 5.28–5.41 (2H, m), 6.00–6.09 (1H, m), 7.53 (1H, d, J=9 Hz), 8.37 (1H, dd, J=9 Hz, 2 Hz), 8.48 (1H, d, J=7 Hz), 8.99 (1H, t, J=5 Hz), 9.36 (1H, d, J=2 Hz), 13.65 (1H, br s)

IR (ν, cm⁻¹), KBr: 3238, 2958, 1651, 1610, 1583, 1338, 746 m.p.: 230 to 232° C.

Example 35

4-Allylamino-6-nitro-2-pentylaminoquinazoline hydrochloride

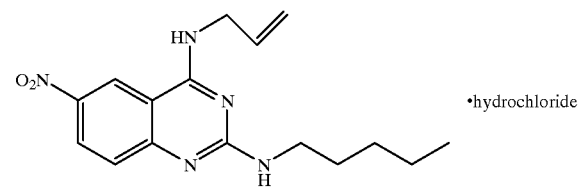

A mixture of 200 mg (0.76 mmol) of 4-allylamino-2-chloro-6-nitroquinazoline and 1.50 g (17.25 mmol) of pentylamine was stirred at room temperature for 2 hours. Water was added to the reaction solution, followed by extraction with ethyl acetate, washing brine and drying over anhydrous sodium sulfate. After the solvent was distilled off, the residue was purified by a silica gel column to give 219 mg (91.9%) of the free base compound of the title compound.

NMR (δ, CDCl₃, 55° C.): 0.90–0.94 (3H, m), 1.38–1.43 (4H, m), 1.61–1.68 (2H, m), 3.52 (2H, m), 4.25 (2H, t, J=5 Hz), 5.21 (1H, br), 5.25–5.33 (2H, m), 5.70 (1H, br), 5.97–6.07 (1H, m), 7.39 (1H, d, J=9 Hz), 8.28 (1H, dd, J=9 Hz, 2 Hz), 8.48 (1H, d, J=2 Hz)

EI-Mass (m/z, %): 315 (M⁺, 76), 286 (55), 272 (67), 259 (100), 258 (97), 245 (65), 212 (72)

Under ice cooling, a 4N hydrochloric acid-ethyl acetate solution was added dropwise to a solution of 92 mg (0.29 mmol) of the free base compound of the title compound in ethyl acetate. Crystals thus precipitated were filtered to give 98 mg (yield: 96.1%) of the title compound.

NMR (δ, CDCl₃): 0.89 (3H, t, J=7 Hz), 1.29–1.42 (4H, m), 1.64–1.71 (2H, m), 3.53–3.58 (2H, m), 4.39 (2H, t, J=6 Hz), 5.24–5.38 (2H, m), 5.99–6.09 (1H, m), 7.55 (1H, d, J=9 Hz), 8.22 (1H, t, J=6 Hz), 8.37 (1H, dd, J=9 Hz, 2 Hz), 9.62 (1H, d, J=2 Hz), 9.68 (1H, t, J=6 Hz), 13.53 (1H, br s)

IR (ν, cm⁻¹), KBr: 3080, 2926, 1651, 1612, 1583, 1448, 1335, 844 m.p.: 207 to 209° C.

Example 36

4-Allylamino-2-heptylamino-6-nitroquinazoline

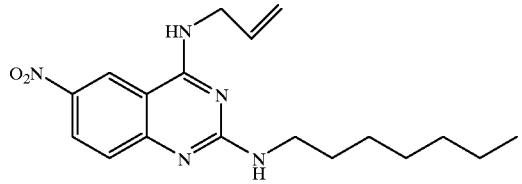

A mixture of 200 mg (0.76 mmol) of 4-allylamino-2-chloro-6-nitroquinazoline and 1.55 g (13.49 mmol) of heptylamine was stirred at room temperature for 2 hours. Water was added to the reaction solution, followed by extraction with ethyl acetate, washing brine and drying over anhydrous sodium sulfate. After the solvent was distilled off, the residue was purified by a silica gel column to give 228 mg (87.8%) of the title compound.

NMR (δ, CDCl₃, 55° C.): 0.89 (3H, t, J=7 Hz), 1.26–1.44 (8H, m), 1.60–1.67 (2H, m), 3.51 (2H, m), 4.25 (2H, t, J=5 Hz), 5.20 (1H, br), 5.25–5.33 (2H, m), 5.70 (1H, br), 5.97–6.07 (1H, m), 7.39 (1H, d, J=8 Hz), 8.28 (1H, dd, J=8 Hz, 3 Hz), 8.48 (1H, d, J=3 Hz)

EI-Mass (m/z, %): 343 (M⁺, 79), 300 (56), 272 (64), 259 (100), 258 (95), 245 (57), 212 (57)

IR (ν, cm⁻¹), KBr: 3394, 2927, 1612, 1556, 1481, 1306, 829 m.p.: 173 to 174° C.

Example 37

4-Allylamino-6-nitro-2-piperidinoaminoquinazoline

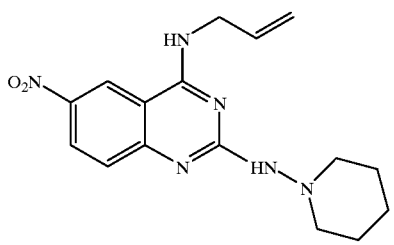

A mixture of 200 mg (0.76 mmol) of 4-allylamino-2-chloro-6-nitroquinazoline and 1.86 g (18.53 mmol) of 1-aminopiperidine was stirred at room temperature for 2 hours. Water was added to the reaction solution followed by extraction with ethyl acetate, washing brine, and drying over anhydrous sodium sulfate. After the solvent was distilled off, the residue was purified by a silica gel column to give 100 mg (40.3%) of the title compound.

NMR (δ, CDCl₃): 1.42–1.49 (2H, m), 1.73–1.78 (4H, m), 2.86 (4H, br), 4.26 (2H, t, J=6 Hz), 5.24–5.36 (2H, m), 5.93–6.06 (3H, m), 7.58 (1H, d, J=9 Hz), 8.30 (1H, dd, J=9 Hz, 3 Hz), 8.59 (1H, d, J=3 Hz)

EI-Mass (m/z, %): 328 (M⁺, 8), 245 (64), 230 (100), 84 (29)

IR (ν, cm⁻¹) KBr: 3400, 2927, 1595, 1477, 1306, 847 m.p.: 221 to 222° C.

Example 38

4-Allylamino-6-nitro-2-(2-propoxyethylamino)quinazoline

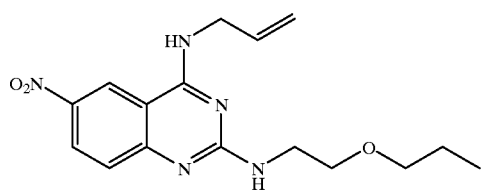

100 mg (0.38 mmol) of 4-allylamino-2-chloro-6-nitroquinazoline was dissolved in 1.5 ml of acetonitrile, and 124 mg (0.76 mmol) of 2-propoxyethylamine hydrochloride and 196 mg (1.94 mmol) of triethylamine were added thereto, followed by stirring at 80° C. for 15 hours. Water was added to the reaction solution, followed by extraction with ethyl acetate, washing brine and drying over anhydrous sodium sulfate. After the solvent was distilled off, the residue was purified by a silica gel column to give 91 mg (72.3%) of the title compound.

NMR (δ, CDCl₃, 55° C.): 0.92–0.96 (3H, m), 1.57–1.64 (2H, m), 3.42–3.46 (2H, m), 3.62 (2H, t, J=5 Hz), 3.70–3.74 (2H, m), 4.24–4.27 (2H, m), 5.23–5.35 (2H, m), 5.61 (1H, br), 5.73 (1H, br), 5.97–6.06 (1H, m), 7.40 (1H, d, J=9 Hz), 8.28 (1H, dd, J=9 Hz, 3 Hz), 8.48 (1H, d, J=3 Hz)

EI-Mass (m/z, %): 331 (M⁺, 29), 301 (9), 288 (100), 258 (92) 212 (43)

IR (ν, cm⁻¹), KBr: 3397, 3255, 1608, 1554, 1477, 1303, 1102, 837 m.p.: 169 to 170° C.

Example 39

2-Allylamino-6-nitro-4-(2-propoxyethylamino)quinazoline

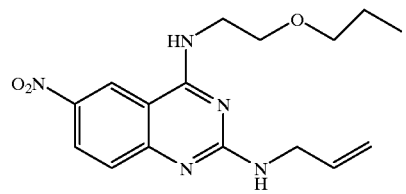

To 450 mg (2.17 mmol) of 6-nitroquinazoline-2,4(1H, 3H)-dione were added 4.50 ml (48.28 mmol) of phosphorus oxychloride and 658 mg (5.43 mmol) of collidine, and the resulting mixture was subjected to heating under reflux for 24 hours. After phosphorus oxychloride was removed in vacuo, the mixture was dissolved in 10 ml of acetonitrile, followed by adding thereto 320 mg (2.29 mmol) of 2-propoxyethylamine hydrochloride and 3.51 ml (25.18 mmol) of triethylamine under ice cooling and stirring under ice cooling for 30 minutes. After water was added to the reaction solution, crystals thus precipitated were filtered to give 2-chloro-6-nitro-4-(2-propoxyethylamino)quinazoline. 5.00 ml (66.64 mmol) of allylamine was added to the compound, followed by stirring at room temperature for 5 hours. Water was added to the reaction solution, followed by extraction with ethyl acetate, washing with brine and drying over anhydrous sodium sulfate. After the solvent was distilled off, the residue was purified by a silica gel column to give 346 mg (48.1%) of the title compound.

NMR (δ, CDCl₃, 55° C.): 0.97 (3H, t, J=7 Hz), 1.61–1.70 (2H, m), 3.49 (2H, t, J=7 Hz), 3.69 (2H, t, J=5 Hz), 3.78–3.82 (2H, m), 4.17 (2H, t, J=6 Hz), 5.14–5.30 (3H, m), 5.93–6.03 (1H, m), 6.12 (1H, br), 7.39 (1H, d, J=9 Hz), 8.27 (1H, dd, J=9 Hz, 3 Hz), 8.48 (1H, d, J=3 Hz)

EI-Mass (m/z, %): 331 (M⁺, 63), 316 (100), 258 (13), 212 (12)

IR (ν, cm⁻¹), KBr: 3388, 2924, 1587, 1535, 1493, 1311, 1117, 746 m.p.: 156 to 157° C.

Reference Example 10

2-Allylamino-4-amino-6-nitroquinazoline

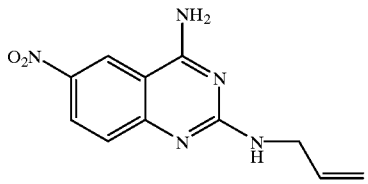

To 622 mg (3.00 mmol) of 6-nitroquinazoline-2,4 (1H, 3H)-dione was added 25.60 g (0.17 mol) of phosphorus oxychloride and then the resulting mixture was subjected to heating under reflux for 4 days. Phosphorus oxychloride was removed in vacuo, followed by crystallization from ether-hexane to give the dichloride as crude crystal. After the dichloride thus obtained was dissolved in 5 ml of DMF and 0.73 ml (12.00 mmol) of a 28% aqueous ammonia solution was added thereto, the mixture was stirred under ice cooling for 2 hours. Water was added to the reaction solution, followed by extraction with ethyl acetate, washing with brine, drying over anhydrous sodium sulfate and distilling off the solvent to give 4-amino-2-chloro-6-nitroquinazoline. After 5 ml of allylamine was added thereto, the mixture was stirred at room temperature overnight. Water was added to the reaction mixture, followed by extraction with chloroform, washing with brine and drying over anhydrous sodium sulfate. After the solvent was distilled off, the residue was purified by a silica gel column to give 342mg (46.5%) of the title compound.

NMR (δ, DMSO-$d_6$, 55° C.): 3.99–4.02 (2H, m), 5.03–5.20 (2H, m), 5.88–5.93 (1H, m), 7.17 (1H, br), 7.25 (1H, d, J=9 Hz), 7.71 (2H, br), 8.20 (1H, dd, J=9 Hz, 3 Hz), 9.05 (1H, d, J=3 Hz)

Example 40

2-Allylamino-4-(t-butylcarbamoyl)amino-6-nitroquinazoline

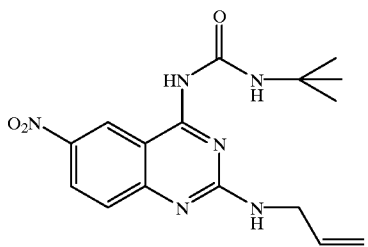

To 5 ml of a solution of 165 mg (0.67 mmol) of 2-allylamino-4-amino-6-nitroquinazoline in THF was added 17 mg (10.7 mmol) of sodium hydride. After the mixture was stirred under ice cooling for 0.5 hour, 76 mg (0.77 mmol) of t-butylisocyanate was added, followed by stirring for 1.5 hours at room temperature. After completion of the reaction, ice water was added to the reaction mixture, followed by extraction with chloroform (10 ml×3). After the organic layer was washed with brine and then dried over anhydrous sodium sulfate, the solvent was distilled off under reduced pressure. The residue was purified by a silica gel chromatography to give 79 mg (yield: 34.2%) of the title compound.

m.p.: 200 to 201° C.

NMR (δ, CDCl3): 1.41 (9H, s), 4.04 (2H, br), 5.12 (1H, dd, J=9 Hz, 2 Hz), 5.21 (1H, d, J=17 Hz), 5.92–6.02 (1H, m), 7.39 (2H, d, J=8 Hz), 7.67 (1H, br), 8.29 (1H, dd, J=8 Hz, 2 Hz), 9.14 (1H, br), 9.46 (1H, d, J=2 Hz), 10.14 (1H, br).

IR (ν, cm$^{-1}$), KBr: 1685, 1597, 1323.

EI-Mass (m/z, %): 344 (M$^+$, 13), 271 (35), 256 (80), 230 (100).

Example 41

2-[N-allyl-N-(t-butylcarbamoyl)amino]-4-(t-butylcarbamoyl)amino-6-nitroquinazoline

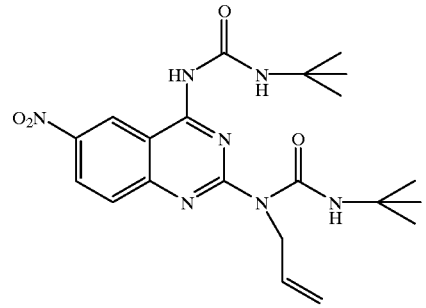

To 5 ml of a solution of 123 mg (0.50 mmol) of 2-allylamino-4-amino-6-nitroquinazoline in DMF were added 56 mg (0.55 mmol) of potassium t-butoxide and 50 mg (0.50 mmol) of t-butylisocyanate, and then the reaction mixture was subjected to heating at 150° C. for 0.5 hour. After completion of the reaction, the solvent was distilled off under reduced pressure. The residue was purified by a silica gel chromatography to give 80 mg (yield: 36.0%) of the title compound.

m.p.: 105 to 106° C.

NMR (δ, CDCl$_3$): 1.44 (9H, s), 1.49 (9H, s), 4.82 (2H, d, J=5 Hz), 5.16–5.20 (2H, m), 5.92–6.00 (1H, m), 7.60 (1H, d, J=9 Hz), 8.51–8.54 (2H, m), 9.09 (2H, br), 10.87 (1H, br s).

IR (ν, cm$^{-1}$), KBr: 1693, 1550, 1365,763.

EI-Mass (m/z, %): 443 (M$^+$, 2), 344 (15), 271 (43), 256 (97), 230 (100).

Example 42

4-Acetylamino-2-allylamino-6-nitroquinazoline

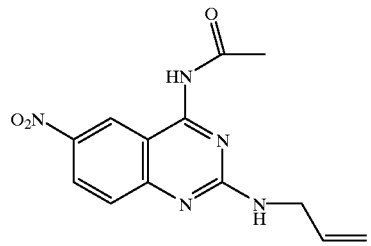

300 mg (1.22 mmol) of 2-allylamino-4-amino-6-nitroquinazoline was dissolved in 5 ml of THF, and then 5.0 g (29.38 mmol) of acetic anhydride and 30 mg (0.37 mmol) of sodium acetate were added thereto, followed by stirring at room temperature for 12 hours. The reaction solution was neutralized with a 1 N aqueous sodium hydroxide solution. Crystals thus precipitated were filtered, followed by washing with water and drying to give 150 mg (42.7%) of the title compound.

NMR (δ, DMSO-d$_6$, 55° C.): 2.39 (3H, s), 4.04–4.07 (2H, m), 5.07–5.23 (2H, m), 5.91–6.01 (1H, m), 7.47 (1H, d, J=9 Hz), 7.92 (1H, br), 8.32 (1H, d, J=9 Hz), 9.10 (1H, br), 10.79 (1H, br).

EI-Mass (m/z, %): 287 (M$^+$, 51), 272 (76), 244 (20), 230 (100).

IR (ν, cm$^{-1}$), KBr: 3257, 3085, 1685, 1618, 1504, 1333, 1302.

m.p.: 253 to 254° C.

Example 43

2-Allylamino-4-(2-methylpropoxycarbonyl)amino-6-nitroquinazoline

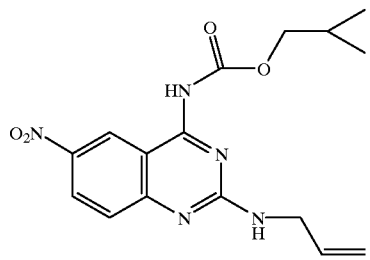

500 mg (2.04 mmol) of 2-allylamino-4-amino-6-nitroquinazoline was dissolved in 5 ml of DMF, and then 80 mg (2.33 mmol) of 70% sodium hydride and 280 mg (2.05 mmol) of 2-methylpropoxycarbonyl chloride were added thereto under ice cooling, followed by stirring for 3 hours. Water was added to the reaction solution, followed by extraction with ethyl acetate, successive washing with brine and drying over anhydrous sodium sulfate. After the solvent was distilled off, the residue was purified by a silica gel column to give 131 mg (19.1%) of the title compound.

NMR (δ, CDCl$_3$): 1.01 (6H, d, J=7 Hz), 2.01–2.11 (1H, m), 4.08 (2H, d, J=7 Hz), 4.21–4.23 (2H, m), 5.18–5.33 (2H, m), 5.70 (1H, br), 5.93–6.03 (1H, m), 7.58 (1H, br), 7.75 (1H, br), 8.39 (1H, d, J=9 Hz), 8.72 (1H, br).

EI-Mass (m/z, %): 345 (M$^+$, 25), 330 (34), 271 (40), 256 (100), 230 (42), 210 (36).

IR (ν, cm$^{-1}$), KBr: 3325, 3257, 2960, 1732, 1622, 1514, 1329.

m.p.: 148 to 149° C.

Reference Example 11

4-Allylamino-2-amino-6-nitroquinazoline

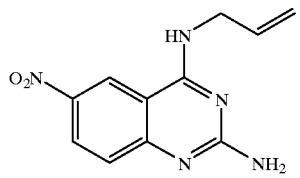

After 10 ml of ammonia gas was dissolved in 50 ml of ethanol at −78° C., 15 ml of a solution of 2.40 g (9.07 mmol) of 4-allylamino-2-chloro-6-nitroquinazoline in THF was added thereto, followed by stirring overnight in a sealed tube at 70° C. 150 ml of water was added to the reaction solution, and then crystals thus precipitated were filtered out, followed by recrystallization from ethyl acetate-hexane to give 1.88 g (84.6%) of the title compound.

NMR (δ, DMSO-d$_6$): 4.13–4.17 (2H, m), 5.11–5.27 (2H, m), 5.94–6.02 (1H, m), 6.84 (2H, br), 7.23 (1H, d, J=9 Hz), 8.22 (1H, dd, J=9 Hz, 3 Hz), 8.72 (1H, t, J=6 Hz), 9.14 (1H, d, J=3 Hz)

Example 44

2-Acetylamino-4-allylamino-6-nitroquinazoline

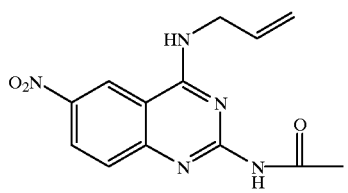

After 100 mg (0.41 mmol) of 4-allylamino-2-amino-6-nitroquinazoline was dissolved in 10 ml of acetonitrile, 84 mg (0.82 mmol) of acetic anhydride and 0.06 ml (0.45 mmol) of triethylamine were added thereto, and then the reaction mixture was subjected to heating under reflux overnight. Water was added to the reaction solution, followed by extraction with ethyl acetate, washing successively with a saturated aqueous sodium hydrogen carbonate solution and brine and drying over anhydrous sodium sulfate. The solvent was distilled off, followed by recrystallization from ethyl acetate-hexane to give 95 mg (80.7%) of the title compound.

NMR (δ, DMSO-d$_6$): 2.33 (3H, s), 4.20–4.22 (2H, m), 5.14–5.30 (2H, m), 5.97–6.07 (1H, m), 7.59 (1H, d, J=9 Hz), 8.40 (1H, dd, J=9 Hz, 3 Hz), 9.21 (1H, t, J=5 Hz), 9.31 (1H, d, J=3 Hz), 10.19 (1H, s)

EI-Mass (m/z, %): 287 (M$^+$, 100), 272 (67), 244 (29), 230 (98), 198 (45), 184 (37)

IR (ν, cm$^{-1}$), KBr: 3367, 1671, 1596, 1471, 1313, 1020, 748 m.p.: 239 to 240° C.

Example 45

4-Allylamino-6-nitro-2-(propylcarbamoyl)aminoquinazoline

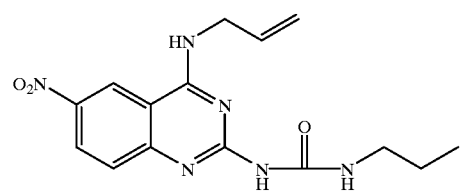

After 200 mg (0.82 mmol) of 4-allylamino-2-amino-1-nitroquinazoline was dissolved in 10 ml of THF, 153 mg (1.80 mmol) of propylisocyanate and 0.13 ml (0.90 mmol) of triethylamine were added thereto, and then the reaction mixture was subjected to heating under reflux overnight. Water was added to the reaction solution, followed by extraction with ethyl acetate, washing with brine and drying over anhydrous sodium sulfate. After the solvent was distilled off, the residue was purified by a silica gel column to give 218 mg (80.5%) of the title compound.

NMR (δ, DMSO-d$_6$): 0.94 (3H, t, J=7 Hz), 1.51–1.60 (2H, m), 3.19–3.24 (2H, m), 4.17 (2H, t, J=5 Hz), 5.15–5.32 (2H, m), 5.95–6.04 (1H, m), 7.59 (1H, d, J=9 Hz), 8.40 (1H, dd, J=9 Hz, 3 Hz), 9.24 (1H, t, J=5 Hz), 9.28 (1H, d, J=3 Hz), 9.38 (1H, s), 9.52 (1H, t, J=6 Hz)

EI-Mass (m/z, %): 330 (M$^+$, 14), 301 (100), 272 (54), 226 (10)

IR (ν, cm$^{-1}$), KBr: 3237, 1675, 1598, 1531, 1469, 1326, 1238, 638 m.p.: 254 to 255° C.

Example 46

2-Allylamino-4-(2,2-dimethylhydrazino)-6-nitroquinazoline

To 300 mg (1.45 mmol) of 6-nitroquinazoline-2,4(1H,3H)-dione were added 1 ml of 1,3-dimethyl-2-imidazolidinone and 1.23 g (8.05 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 520 mg (8.69 mmol) of N,N-dimethylhydrazine and stirring under ice cooling for 30 minutes. To the reaction solution was added water, followed by extraction with ethyl acetate, washing with brine and drying over anhydrous sodium sulfate. After the solvent was distilled off to give 2-chloro-4-(2,2-dimethylhydrazino)-6-nitroquinazoline. After 2.00 ml (26.65 mmol) of allylamine was added thereto and then the mixture was stirred at room temperature for 3 hours, water was added to the reaction solution, followed by extraction with ethyl acetate, washing with brine and drying over anhydrous sodium sulfate. After the solvent was distilled off, the residue was purified by a silica gel column to give 73 mg (17.5%) of the title compound.

NMR (δ, CDCl$_3$, 55° C.): 2.75 (6H, s), 4.15–4.18 (2H, m), 5.14–5.30 (2H, m), 5.36 (JH, br), 5.92–6.01 (JH, m), 6.22 (1H, br), 7.43 (1H, d, J=9 Hz), 8.29 (JH, dd, J=9 Hz, 3 Hz), 9.12 (1H, br).

EI-Mass (m/z, %): 288 (M$^+$, 51), 273 (8), 245 (88), 230 (100), 198 (23), 184 (54).

IR (ν, cm$^{-1}$), KBr: 3307, 3257, 3101, 1587, 1552, 1296.

m.p.: 145 to 146° C.

Reference Example 12

2-Chloro-4-dodecylamino-6-nitroquinazoline

To 250 mg (1.21 mmol) of 6-nitroquinazoline- 2,4(1H, 3H)-dione were added 5.00 ml (53.64 mmol) of phosphorus oxychloride and 0.18 ml (1.21 mmol) of diisopropylformamide, and the resulting mixture was subjected to heating under reflux for 24 hours. After phosphorus oxychloride was removed in vacuo, the mixture was dissolved in 5 ml of acetonitrile, followed by addition of 2.80 ml (12.10 mmol) of dodecylamine under ice cooling and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 310 mg (67.0%) of the title compound.

NMR (δ, CDCl$_3$): 0.88 (3H, t, J=7 Hz), 1.27–1.49 (18H, m), 1.74–1.81 (2H, m), 3.70–3.75 (2H, m), 6.21 (1H, br), 7.86 (1H, d, J=9 Hz), 8.51 (1H, dd, J=9 Hz, 2 Hz), 8.69 (1H, d, J=2 Hz)

Example 47

2-Allylamino-4-dodecylamino-6-nitroquinazoline

To 170 mg (0.44 mmol) of 2-chloro-4-dodecylamino-6-nitroquinazoline was added 1.70 ml (22.66 mmol) of allylamine, and then the resulting mixture was stirred at room temperature overnight. After water was added to the reaction solution, crystals thus precipitated were filtered to give 170 mg (93.4%) of the title compound.

NMR (δ, CDCl$_3$, 55° C.): 0.88 (3H, t, J=7 Hz), 1.27–1.48 (18H, m), 1.68–1.75 (2H, m), 3.58–3.63 (2H, m), 4.16–4.19 (2H, m), 5.14–5.30 (3H, m), 5.68 (1H, br), 5.94–6.03 (1H, m), 7.39 (1H, d, J=9 Hz), 8.28 (1H, dd, J=9 Hz, 2 Hz), 8.46 (1H, d, J=2 Hz)

EI-Mass (m/z, %): 413 (M$^+$, 21), 398 (100), 384 (18), 370 (20), 356 (14), 272 (14)

IR (ν, cm$^{-1}$), KBr: 3397, 2923, 1612, 1563, 1479, 1301, 1103, 746 m.p.: 154 to 155° C.

Example 48

4-Allylamino-2-dodecylamino-6-nitroquinazoline

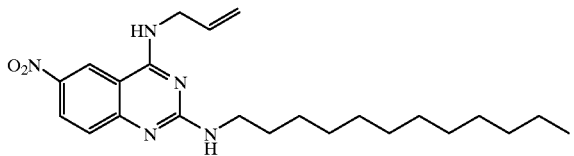

150 mg (0.57 mmol) of 4-allylamino-2-chloro-nitroquinazoline was dissolved in 10 ml of acetonitrile, and then 158 mg (0.86 mmol) of dodecylamine and 0.40 ml (2.85 mmol) of triethylamine were added thereto, followed by heating under reflux overnight. To the reaction solution was added water, followed by extraction with ethyl acetate, washing with brine and drying over anhydrous sodium sulfate. After the solvent was distilled off, the residue was purified by a silica gel column to give 223 mg (94.7%) of the title compound.

NMR (δ, CDCl$_3$, 55° C.): 0.88 (3H, t, J=7 Hz), 1.22–1.42 (18H, m), 1.60–1.67 (2H, m), 3.49–3.54 (2H, m), 4.24–4.26 (2H, m), 5.21 (1H, br), 5.23–5.35 (2H, m), 5.71 (1H, br), 5.97–6.07 (1H, m), 7.39 (1H, d, J=9 Hz), 8.27 (1H, dd, J=9 Hz, 2 Hz), 8.48 (1H, d, J=2 Hz)

EI-Mass (m/z, %): 413 (M$^+$, 84), 384 (24), 370 (25), 356 (22), 272 (55), 259 (100), 258 (69), 212 (32)

IR (ν, cm$^{-1}$), KBr: 3394, 2921, 1614, 1558, 1481, 1303, 1105, 829 m.p.: 148 to 155° C.

Reference Example 13

2-Chloro-4-(1-methylpropylamino)-6-nitroquinazoline

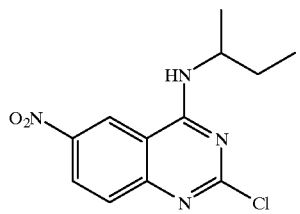

To 250 mg (1.21 mmol) of 6-nitroquinazoline-2,4(1H, 3H)-dione were added 5.00 ml (53.64 mmol) of phosphorus oxychloride and 0.18 ml (1.21 mmol) of diisopropylformamide, and the resulting mixture was subjected to heating under reflux for 24 hours. After phosphorus oxychloride was removed in vacuo, the mixture was dissolved in 5 ml of acetonitrile, followed by addition of 1.23 ml (12.10 mmol) of 1-methylpropylamine under ice cooling and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 234 mg (68.9%) of the title compound.

NMR (δ, CDCl$_3$): 1.03 (3H, t, J=8 Hz), 1.38 (3H, d, J=7 Hz), 1.69–1.81 (2H, m), 4.47–4.56 (1H, m), 6.15 (1H, d, J=8 Hz), 7.84 (1H, d, J=9 Hz), 8.50 (1H, dd, J=9 Hz, 2 Hz), 8.75 (1H, d, J=2 Hz)

Example 49

2-Allylamino-4-(1-methylpropylamino)-6-nitroquinazoline hydrochloride

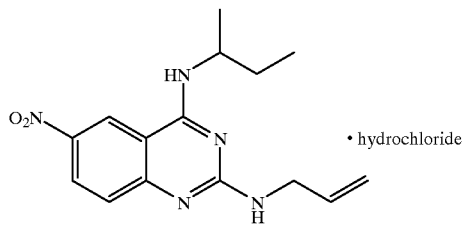

To 150 mg (0.53 mmol) of 2-chloro-4-(1-methylpropylamino)-6-nitroquinazoline was added 1.50 ml (20.00 mmol) of allylamine, and the resulting mixture was stirred at room temperature for 4 hours. To the reaction solution was added water, followed by extraction with ethyl acetate, washing with brine and drying over anhydrous sodium sulfate. After the solvent was distilled off, the residue was purified by a silica gel column to give 156 mg (98.0%) of the free base compound of the title compound.

NMR (δ, CDCl$_3$, 55° C.): 1.00 (3H, t, J=8 Hz), 1.31 (3H, d, J=7 Hz), 1.61–1.77 (2H, m), 4.15–4.18 (2H, m), 4.29–4.39 (1H, m), 5.13–5.29 (3H, m), 5.46 (1H, br), 5.93–6.03 (1H, m), 7.39 (1H, d, J=9 Hz), 8.27 (1H, dd, J=9 Hz, 3 Hz), 8.46(1H, d, J=3 Hz)

Under ice cooling, a 4N hydrochloric acid-ethyl acetate solution was added dropwise to a solution of 100 mg (0.33 mmol) of the free base compound of the title compound in ethyl acetate. Crystals thus precipitated were filtered to give 105 mg (yield: 94.2%) of the title compound.

NMR (δ, CDCl$_3$): 1.02 (3H, t, J=7 Hz), 1.46 (3H,d, J=7 Hz), 1.74–2.00 (2H, m), 4.17–4.20 (2H, m), 4.46–4.53 (1H, m), 5.18–5.35 (2H, m), 5.85–5.95 (1H, m), 7.61 (1H, d, J=9 Hz), 8.38–8.41 (2H, m), 8.75 (1H, d, J=8 Hz), 9.59 (1H, d, J=2 Hz), 13.84 (1H, s)

EI-Mass (m/z, %): 301 (M$^+$, 60), 286 (100), 272 (10), 226(7)

IR (ν, cm$^{-1}$), KBr: 3214, 1668, 1610, 1556, 1502, 1342, 926 m.p.: 176 to 177° C.

Example 50

4-Allylamino-2-(1-methylpropylamino)-6-nitroquinazoline hydrochloride

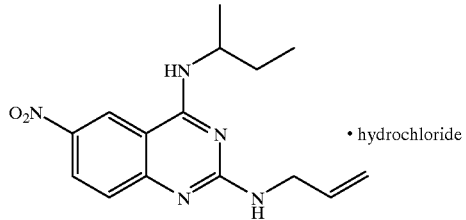

A mixture of 160 mg (0.61 mmol) of 4-allylamino-2-chloro-6-nitroquinazoline and 1.60 ml (15.84 mmol) of 1-methylpropylamine was stirred at room temperature overnight. To the reaction solution was added water, followed by extraction with ethyl acetate, washing with brine and drying over anhydrous sodium sulfate. After the solvent was distilled off, the residue was purified by a silica gel column to give 180 mg (98.4%) of a free base compound of the title compound.

NMR (δ, CDCl₃, 55° C.): 0. 98 (3H, t, J=8 Hz), 1.24 (3H, d, J=6 Hz), 1.54–1.66 (2H, m), 4.12–4.19 (1H, m), 4.25 (2H, t, J=6 Hz), 5.08 (eH, br), 5.24–5.35 (2H, m), 5.73 (1H, br), 5.97–6.07 (1H, m), 7.37 (1H, d, J=8 Hz), 8.27 (1H, dd, J=8 Hz, 2 Hz), 8.48 (1H, d, J=2 Hz)

Under ice cooling, a 4N hydrochloric acid-ethyl acetate solution was added dropwise to a solution of 100 mg (0.33 mmol) of the free base compound of the title compound in ethyl acetate. Crystals thus precipitated were filtered out to give 100 mg (yield: 90.9%) of the title compound.

NMR (δ, CDCl₃): 0.99 (3H, t, J=8 Hz), 1.31 (3H, d, J=7 Hz), 1.61–1.74 (2H, m), 4.10–4.20 (1H, m), 4.37–4.40 (2H, m), 5.24–5.38 (2H, m), 5.99–6.08 (1H, m), 7.50 (1H, d, J=9 Hz), 8.13 (1H, d, J=8 Hz), 8.34 (1H, dd, J=9 Hz, 2 Hz), 9.57–9.61 (2H, m), 13.52 (1H, s)

EI-Mass (m/Z, %): 301 (M⁺, 44), 286 (27), 272 (100), 226 (37)

IR (ν, cm⁻¹), KBr: 3215, 1651, 1610, 1587, 1340, 744 m.p.: 219 to 220° C.

Reference Example 14

4-t-Butylamino-2-chloro-6-nitroquinazoline

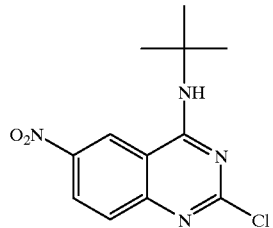

To 250 mg (1.21 mmol) of 6-nitroquinazoline-2,4(1H, 3H)-dione were added 5.00 ml (53.64 mmol) of phosphorus oxychloride and 0.18 ml (1.21 mmol) of diisopropylformamide, and the resulting mixture was subjected to heating under reflux for 24 hours. After phosphorus oxychloride was removed in vacuo, the mixture was dissolved in 5 ml of acetonitrile, followed by addition of 1.26 ml (12.10 mmol) of t-butylamine under ice cooling and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 218 mg (64.2%) of the title compound.

NMR (δ, CDCl₃): 1.65 (9H, s), 6.07 (1H, br), 7.83 (1H, d, J=9 Hz), 8.48 (1H, dd, J=9 Hz, 2 Hz), 8.64 (1H, d, J=2 Hz)

Example 51

2-Allylamino-4-t-butylamino-6-nitroquinazoline hydrochloride

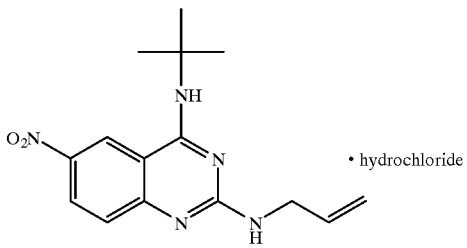

To 150 mg (0.55 mmol) of 4-t-butylamino-2-chloro-6-nitroquinazoline was added 1.60 ml (21.32 mmol) of allylamine, and the resulting mixture was stirred at room temperature overnight. To the reaction solution was added water, followed by extraction with ethyl acetate, washing with brine and drying over anhydrous sodium sulfate. After the solvent was distilled off, the residue was purified by a silica gel column to give 165 mg (98.2%) of a free base compound of the title compound.

NMR (δ, CDCl₃): 1.59. (9H, s), 4.16–4.19 (2H, m), 5.15–5.30 (2H, m), 5.42 (1H, br), 5.63 (1H, br), 5.94–6.03 (1H, m), 7.36 (1H, br), 8.28 (1H, dd, J=9 Hz, 2 Hz), 8.44 (1H, d, J=2 Hz)

Under ice cooling, a 4N hydrochloric acid-ethyl acetate solution was added dropwise to a solution of 102 mg (0.34 mmol) of the free base compound of the title compound in ethyl acetate. Crystals thus precipitated were filtered out to give 100 mg (yield: 88.2%) of the title compound.

NMR (δ, CDCl₃): 1.67 (9H, s), 4.18–4.21 (2H, m), 5.22–5.37 (2H, m), 5.86–5.95 (1H, m), 7.00 (1H, s), 7.68 (1H, d, J=9 Hz), 8.46 (1H, dd, J=9 Hz, 2 Hz), 8.70 (1H, t, J=6 Hz), 8.85 (1H, d, J=2 Hz), 14.54 (1H, s)

EI-Mass (m/z, %): 301 (M⁺, 61), 286 (56), 244 (18), 230 (100)

IR (ν, cm⁻¹), KBr: 3222, 3084, 1653, 1608, 1574, 1444, 1338, 1207, 744 m.p.: 208 to 209° C.

Reference Example 15

4-(1-Adamantylamino)-2-chloro-6-nitroquinazoline

To 250 mg (1.21 mmol) of 6-nitroquinazoline-2,4(1H, 3H)-dione were added 5.00 ml (53.64 mmol) of phosphorus oxychloride and 0.18 ml (1.21 mmol) of diisopropylformamide, and the resulting mixture was subjected to heating under reflux for 24 hours. After phosphorus oxychloride was removed in vacuo, the mixture was dissolved in 5 ml of acetonitrile, followed by addition of 183 mg (1.21 mmol) of 1-adamantylamine and 0.84 ml (6.05 mmol) of triethylamine under ice cooling and stirring under ice cooling for 30 minutes. To the reaction solution was added water, followed by extraction with ethyl acetate, washing with brine and drying over anhydrous sodium sulfate. After the solvent was distilled off, the residue was purified by a silica gel column to give 90 mg (20.7%) of the title compound.

NMR (δ, CDCl$_3$): 1.75–1.82 (6H, m), 2.22 (3H, br), 2.28–2.32 (6H, m), 5.83 (1H, br s), 7.82 (1H, d, J=9 Hz), 8.48 (1H, dd, J=9 Hz, 2 Hz), 8.60 (1H, d, J=2 Hz)

Example 52

4-(1-Adamantylamino)-2-allylamino-6-nitroquinazoline

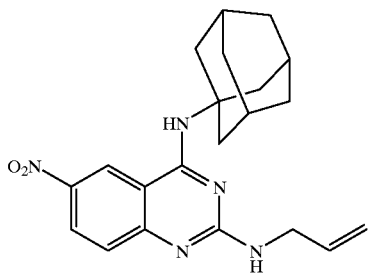

To 82 mg (0.25 mmol) of 4-(1-adamantylamino)-2-chloro-6-nitroquinazoline was added 1.00 ml (13.33 mmol) of allylamine, and the resulting mixture was stirred at room temperature overnight. To the reaction solution was added water, followed by extraction with ethyl acetate, washing with brine and drying over anhydrous sodium sulfate. After the solvent was distilled off, the residue was purified by a silica gel column to give 77 mg (88.7%) of the title compound.

NMR (δ, CDCl$_3$, 55° C.): 1.76–1 77 (6H, m), 2.18 (3H, br), 2.27–2.28 (6H, m), 4.14–4.18 (2H, m), 5.14–5.30 (3H, m), 5.42 (1H, br), 5.94–6.04 (1H, m), 7.35 (1H, d, J=9 Hz), 8.26 (1H, dd, J=9 Hz, 2 Hz), 8.41 (1H, d, J=2 Hz)

EI-Mass (m/z, %): 379 (M$^+$, 65), 364 (100), 135 (44)

IR (ν, cm$^{-1}$), KBr: 3401, 2908, 1587, 1485, 1309, 1107, 839 m.p.: 224 to 225° C.

Example 53

4-Allylamino-6-nitro-2-[2-(piperidinocarbonyl)ethylamino]quinazoline

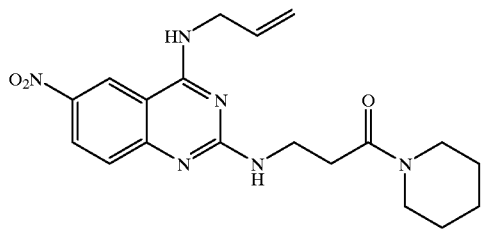

150 mg (0.57 mmol) of 4-allylamino-2-chloro-6-nitroquinazoline was dissolved in 10 ml of acetonitrile, and then 220 mg (1.14 mmol) of 2-piperidinocarbonylethylamine hydrochloride and 0.40 ml (2.85 mmol) of triethylamine were added thereto, followed by heating under reflux overnight. To the reaction solution was added water, followed by extraction with ethyl acetate, washing with brine and drying over anhydrous sodium sulfate. After the solvent was distilled off, the residue was purified by a silica gel column to give 191 mg (87.7%) of the title compound.

NMR (δ, CDCl$_3$, 55° C.): 1.51–1.67 (6H, m), 2.67 (2H, t, J=6 Hz), 3.40 (2H, br), 3.56 (2H, br), 3.87 (2H, td, J=6 Hz, 6 Hz), 4.24 (2H, br), 5.24 (1H, d, J=10 Hz), 5.32 (1H, d, J=17 Hz), 5.95–6.05 (2H, m), 6.90 (1H, br), 7.44 (1H, d, J=9 Hz), 8.29 (1H, dd, J=9 Hz, 2 Hz), 8.62 (1H, br)

EI-Mass (m/z, %): 384 (M$^+$, 17), 300 (2), 272 (100), 258 (10), 226 (15)

IR (ν, cm$^{-1}$), KBr: 3265, 2937, 1620, 1589, 1535, 1484, 1311, 839 m.p.: 178 to 179° C.

Example 54

4-Allylamino-6-nitro-2-(2-pyridylmethylamino)quinazoline

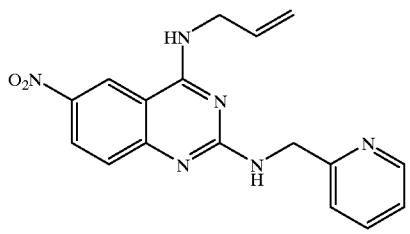

150 mg (0.57 mmol) of 4-allylamino-2-chloro-6-nitroquinazoline was dissolved in 10 ml of acetonitrile, and then 165 mg (1.14 mmol) of 2-pyridylmethylamine hydrochloride and 0.40 ml (2.85 mmol) of triethylamine were added thereto, followed by heating under reflux overnight. To the reaction solution was added water, followed by extraction with ethyl acetate, washing with brine and drying over anhydrous sodium sulfate. After the solvent was distilled off, the residue was purified by a silica gel column to give 180 mg (93.9%) of the title compound.

NMR (δ, DMSO-d$_6$, 55° C.): 3.96–4.20 (2H, m), 4.67 (2H, d, J=6 Hz), 4.96–5.29 (2H, m), 5.72–6.08 (1H, m), 7.20–7.34 (3H, m), 7.60 (1H, br), 7.68–7.72 (1H, m), 8.20 (1H, dd, J=9 Hz, 2 Hz), 8.49 (1H, d, J=5 Hz), 8.68 (1H, br), 9.10 (1H, d, J=2 Hz)

EI-Mass (m/z, %): 336 (M$^+$, 100), 244 (7), 212 (11)

IR (ν, cm$^{-1}$), KBr: 3401, 1587, 1552, 1477, 1304, 1167, 746 m.p.: 202 to 203° C.

Example 55

2-Allylamino-4-(2,2,2-trifluoroethylamino)-6-nitroquinazoline

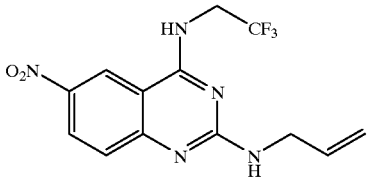

To 250 mg (1.21 mmol) of 6-nitroquinazoline-2,4(1H,3H)-dione were added 5.00 ml (53.64 mmol) of phosphorus oxychloride and 0.18 ml (1.21 mmol) of diisopropylformamide, and the resulting mixture was subjected to heating under reflux for 24 hours. After phosphorus oxychloride was removed in vacuo, the mixture was dissolved in 5 ml of acetonitrile, followed by addition of 328 mg (2.42 mmol) of 2,2,2-trifluoroethylamine hydrochloride and 1.69 ml (12.10 mmol) of triethylamine under ice cooling and stirring under ice cooling for 30 minutes. To the reaction solution was added water, followed by extraction with ethyl acetate, washing with brine and drying over anhydrous sodium sulfate. After the solvent was distilled off, 1.50 ml (20.00 mmol) of allylamine was added thereto, followed by stirring overnight, adding water to the reaction solution, extraction with ethyl acetate, washing with brine and drying over anhydrous sodium sulfate. After the solvent was distilled off, the residue was purified by a silica gel column to give 50 mg (12.6%) of the title compound.

NMR (δ, CDCl$_3$, 55° C.): 3.99–4.02 (2H, m), 4.34–4.43 (2H, m), 5.04–5.20 (2H, m), 5.88–5.98 (1H, m), 7.33 (1H, d, J=9 Hz), 7.51 (1H, br), 8.25 (1H, dd, J=9 Hz, 3 Hz), 8.93 (1H, br), 9.15 (1H, d, J=3 Hz)

EI-Mass (m/z, %): 327 (M$^+$, 65), 312 (100), 266. (60)

IR (ν, cm$^{-1}$), KBr: 3379, 1612, 1556, 1483, 1313, 1250, 1157, 835 m.p.: 215 to 216° C.

Example 56

4-Allylamino-2-(2,2,2-trifluoroethylamino)-6-nitroquinazoline

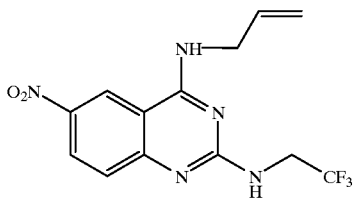

A mixture of 150 mg (0.57 mmol) of 4-allylamino-2-chloro-6-nitroquinazoline, 772 mg (5.70 mmol) of 2,2,2-trifluoroethylamine and 1.15 g (11.4 mmol) of triethylamine was stirred in a sealed tube at room temperature for 16 hours. After completion of the reaction, ice water was added to the reaction mixture, followed by extraction with chloroform (10 ml×3). After the organic layer was washed with brine and then dried over anhydrous sodium sulfate, the solvent was distilled off under reduced pressure. The residue was purified by a silica gel chromatography to give 57 mg (yield: 30.8%) of the title compound.

m.p.: 221 to 222° C.

NMR (δ, CDCl$_3$, 55° C.): 4.21–4.29 (4H, m), 5.26–5.37 (3H, m), 5.85 (1H, br), 5.97–6.06 (1H, m), 7.49 (1H, d, J=8 Hz), 8.34 (1H, dd, J=8 Hz, 2 Hz), 8.53 (1H, d, J=2 Hz).

IR (ν, cm$^{-1}$), KBr: 3396, 1562, 1313, 1160.

EI-Mass (m/z, %): 327 (M$^+$, 100), 312 (86), 258 (28).

Example 57

4-Allylamino-2-(2-chloroethylamino)-6-nitroquinazoline

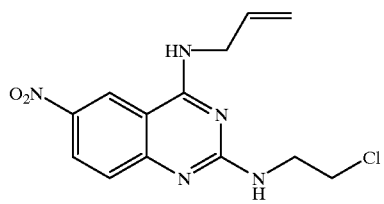

To a solution of 50 mg (0.173 mmol) of 4-allylamino-2-(2-hydroxyethylamino)-6-nitroquinazoline in dichloromethane was added 1.63 g (13.7 mmol) of thionyl chloride, and then the resulting mixture was stirred at room temperature for 4 hours. After the mixture was subjected to heating under reflux for further one hour, the solvent was distilled off under reduced pressure. The residue was purified by a silica gel chromatography to give 25 mg (yield: 46.8%) of the title compound.

NMR (δ, CDCl$_3$): 3.65–3.79 (2H, m), 3.88–3.93 (2H, m), 4.26–4.28 (2H, m), 5.26–5.38 (2H, m), 5.57 (1H, br), 5.83 (1H, br), 5.98–6.08 (1H, m)n, 7.44 (1H, d, J=7 Hz), 8.32 (1H, dd, J=7 Hz, 2 Hz), 8.53 (1H, d, J=2 Hz).

IR (ν, cm$^{-1}$), KBr: 3392, 1610, 1308.

EI-Mass (m/z, %): 309 (M$^+$+2, 7), 307 (M$^+$, 23) 272 (100), 258 (38).

Example 58

4-Allylamino-2-(3-methyl-2-butenylamino)-6-nitroquinazoline

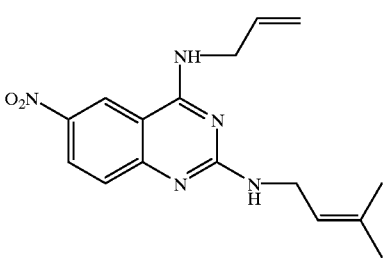

To 10 ml of a solution of 150 mg (0.57 mmol) of 4-allylamino-2-chloro-6-nitroquinazoline in acetonitrile were added 137 mg (1.13 mmol) of 3-methyl-2-butenylamine hydrochloride and 288 mg (2.85 mmol) of triethylamine, followed by heating at room temperature for 4.5 hours. After completion of the reaction, ice water was added to the reaction mixture, followed by extraction with chloroform (10 ml×3). After the organic layer was washed with brine and then dried over anhydrous sodium sulfate, the solvent was distilled off under reduced pressure. The residue was purified by a silica gel chromatography to give 133 mg (yield: 75.1%) of the title compound.

m.p.: 194 to 195° C.

NMR (δ, CDCl$_3$, 50° C.): 1.75 (6H, s), 4.10 (2H, t, J=6 Hz), 4.25 (2H, br), 5.15 (1H, br), 5.24–5.35 (3H, m), 5.73 (1H, br), 5.97–6.06 (1H, m), 7.41 (1H, d, J=8 Hz), 8.28 (1H, dd, J=8 Hz, 2 Hz), 8.49 (1H, d, J=2 Hz).

IR (ν, cm$^{-1}$), KBr: 1597, 1296.

EI-Mass (m/z, %): 313 (M$^+$, 83), 270 (100).

Example 59

2-Allylamino-4-(3-methyl-2-butenylamino)-6-nitroquinazoline

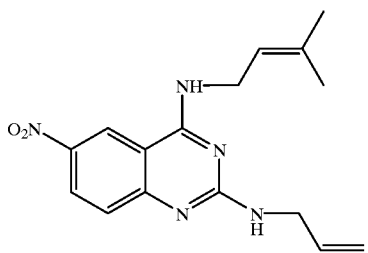

To 278 mg (1.45 mmol) of 6-nitroquinazoline-2,4(1H,3H)-dione were added 0.71 ml of 1,3-dimethyl-2-imidazolidinone and 5.48 g (35.76 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 2.81 ml (20.0 mmol) of triethylamine and 267 mg (2.19 mmol) of 3-methyl-2-butenylamine hydrochloride and stirring under ice cooling for 2 hours. To the reaction solution was added water, followed by extraction with ethyl acetate, washing with brine and drying over anhydrous sodium sulfate. After the solvent was distilled off to give 2-chloro-4-(3-methyl-2-butenylamino)-6-nitroquinazoline. After 1.00 ml (13.33 mmol) of allylamine was added thereto and then the mixture was stirred at room temperature for 3 hours, water was added to the reaction solution, followed by extraction with ethyl acetate, washing with brine and drying over anhydrous sodium sulfate. After the solvent was distilled off, the residue was purified by a silica gel column to give 70 mg (16.7%) of the title compound.

NMR (δ, CDCl$_3$): 1.78 (3H, s), 1.82 (3H, s), 4.18–4.21 (4H, m), 5.15–5.31 (3H, m), 5.38–5.42 (1H, m), 5.57 (1H, br), 5.94–6.04 (1H, m), 7.40 (1H, br), 8.29 (1H, dd, J=9 Hz, 2 Hz), 8.48 (1H, d, J=2 Hz).

EI-Mass (m/z, %): 313 (M$^+$, 100), 298 (97), 270 (21), 244 (29).

IR (ν, cm$^{-1}$), KBr: 3400, 3253, 3086, 1608, 1560, 1306.

m.p.: 209 to 210° C.

Example 60

2-Butylamino-4-(3-methyl-2-butenylamino)-6-nitroquinazoline

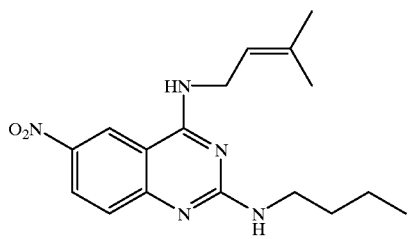

2-chloro-4-(3-methyl-2-butenylamino)-6-nitroquinazoline was obtained in accordance with the process described in Example 59, starting from 278 mg (1.45 mmol) of 6-nitroquinazoline-2,4(1H,3H)-dione. After 1.00 ml (10.12 mmol) of butylamine was added to the compound thus obtained and the reaction mixture was stirred at room temperature for 3 hours, water was added to the reaction solution, followed by extraction with ethyl acetate, washing with brine and drying over anhydrous sodium sulfate. After the solvent was distilled off, the residue was purified by a silica gel column to give 50 mg (11.9%) of the title compound.

NMR (δ, CDCl$_3$): 0.97 (3H, t, J=7 Hz), 1.40–1.49 (2H, m), 1.57–1.66 (2H, m), 1.78 (3H, s), 1.82 (3H, s), 3.51–3.56 (2H, m), 4.15 (2H, br), 5.21 (1H, br), 5.40 (1H, t, J=7 Hz), 5.56 (1H, br), 7.42 (1H, br), 8.28 (1H, dd, J=9 Hz, 2 Hz), 8.47 (1H, d, J=2 Hz).

EI-Mass (m/z, %): 329 (M$^+$, 100), 314 (15), 286 (33), 260 (27).

IR (ν, cm$^{-1}$), KBr: 3396, 3259, 2956, 1593, 1300.

m.p.: 171 to 172° C.

Example 61

2,4-Bis(3-methyl-2-butenylamino)-6-nitroquinazoline

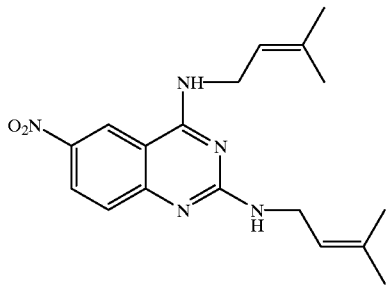

2-chloro-4-(3-methyl-2-butenylamino)-6-nitroquinazoline was obtained in accordance with the process described in Example 59, starting from 278 mg (1.45 mmol) of 6-nitroquinazoline-2,4(1H,3H)-dione. After 0.30 ml (2.14 mmol) of triethylamine and 87 mg (0.72 mmol) of 3-methyl-2-butenylamine hydrochloride were added to the compound and the reaction mixture was stirred at 80° C. for 12 hours, water was added to the reaction solution, followed by extraction with ethyl acetate, washing with brine and drying over anhydrous sodium sulfate. After the solvent was distilled off, the residue was purified by a silica gel column to give 65 mg (14.2%) of the title compound.

NMR (δ, CDCl₃): 1.75 (6H, br), 1.77 (3H, s), 1.81 (3H, s), 4.06–4.13 (4H, m), 5.13 (1H, br), 5.30–5.40 (2H, m), 5.53 (1H, m), 7.40 (1H, br), 8.23 (1H, dd, J=9 Hz, 2 Hz), 8.48 (1H, d, J=2 Hz).

EI-Mass (m/z, %): 341 (M⁺, 100), 326 (13), 298 (78), 272 (32).

IR (ν, cm⁻¹), KBr: 3390, 3248, 3093, 1610, 1583, 1304.

m.p.: 168 to 172° C.

Example 62

2-Butylamino-4-(1-methyl-2-propenylamino)-6-nitroquinazoline

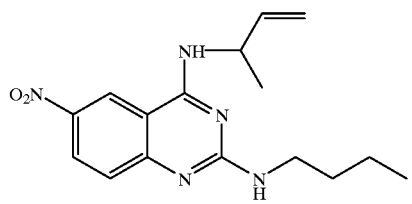

To 278 mg (1.45 mmol) of 6-nitroquinazoline-2,4(1H,3H)-dione were added 0.71 ml of 1,3-dimethyl-2-imidazolidinone and 5.48 g (35.76 mmol) of phosphorus oxychloride, and the resulting mixture was subjected to heating under reflux for 3 hours. After phosphorus oxychloride was removed in vacuo, the mixture was dissolved in 3 ml of acetonitrile, followed by addition of 2.81 ml (20.07 mmol) of triethylamine and 281 mg (2.61 mmol) of 1-methyl-2-propenylamine hydrochloride and stirring under ice cooling for 2 hours. To the reaction solution was added water, followed by extraction with ethyl acetate, washing with brine and drying over anhydrous sodium sulfate. After the solvent was distilled off to give 2-chloro-4-(1-methyl-2-propenylamino)-6-nitroquinazoline. After 1.00 ml (10.12 mmol) of n-butylamine was added thereto and then the mixture was stirred at room temperature for 3 hours, water was added to the reaction solution, followed by extraction with ethyl acetate, washing with brine and drying over anhydrous sodium sulfate. After the solvent was distilled off, the residue was purified by a silica gel column to give 73 mg (17.3%) of the title compound.

NMR (δ, CDCl₃): 0.97 (3H, t, J=8 Hz), 1.44 (5H, br), 1.60 (2H, br), 3.49–3.54 (2H, m), 5.01 (1H, br), 5.18–5.30 (2H, m), 5.51 (1H, br), 5.66 (1H, br), 5.95–6.03 (1H, m), 7.43 (1H, br), 8.29 (1H, dd, J=9 Hz, 2 Hz), 8.49 (1H, d, J=2 Hz).

EI-Mass (m/z, %): 315 (M⁺, 98), 300 (60), 272 (85), 258 (100), 246 (34).

IR (ν, cm⁻¹), KBr: 3408, 3255, 2958, 1606, 1540, 1304 m.p.: 156 to 158° C.

Example 63

2-Allylamino-4-(1-methyl-2-propenylamino)-6-nitroquinazoline

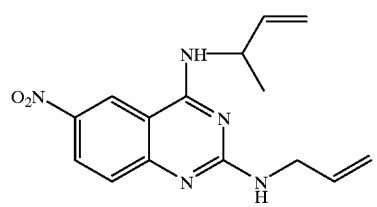

2-chloro-4-(1-methyl-2-propenylamino)-6-nitroquinazoline was obtained in accordance with the process described in Example 62, starting from 278 mg (1.45 mmol) of 6-nitroquinazoline-2,4(1H,3H)-dione. After 1.00 ml (13.33 mmol) of allylamine was added to the compound and the reaction mixture was stirred at room temperature for 3 hours, water was added to the reaction solution, followed by extraction with ethyl acetate, washing with brine and drying over anhydrous sodium sulfate. After the solvent was distilled off, the residue was purified by a silica gel column to give 75 mg (18.7%) of the title compound.

NMR (δ, CDCl₃): 1.34 (3H, d, J=7 Hz), 4.17 (2H, br), 5.01 (1H, q, J=7 Hz), 5.15–5.30 (5H, m), 5.65 (1H, br), 5.94–6.03 (2H, m), 7.40 (1H, br), 7.79 (1H, dd, J=9 Hz, 2 Hz), 8.51 (1H, d, J=2 Hz).

EI-Mass (m/z, %): 299 (M⁺, 53), 284 (100), 244 (15), 230 (23).

IR (ν, cm⁻¹), KBr: 3404, 3246, 3080, 1587, 1535, 1302.

m.p.: 172 to 173° C.

Example 64

2,4-Bis(1-methyl-2-propenylamino)-6-nitroquinazoline

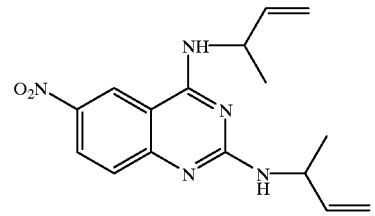

2-chloro-4-(1-methyl-2-propenylamino)-6-nitroquinazoline was obtained in accordance with the process described in Example 62, starting from 278 mg (1.45 mmol) of 6-nitroquinazoline-2,4(1H,3H)-dione. After 0.30 ml (2.14 mmol) of triethylamine and 87 mg (0.81 mmol) of 1-methyl-2-propenylamine hydrochloride were added to the compound and the reaction mixture was stirred at 80° C. for 12 hours, water was added to the reaction solution, followed by extraction with ethyl acetate, washing with brine and drying over anhydrous sodium sulfate. After the solvent was distilled off, the residue was purified by a silica gel column to give 50 mg (11.9%) of the title compound.

NMR (δ, CDCl₃): 1.34–1.36 (3H, m), 1.42–1.46 (3H, m), 4.82 (1H, br), 4.98–5.30 (5H, m), 5.40 (1H, br), 5.80 (1H, br), 5.91–6.04 (2H, m), 7.34 (1H, br), 8.28 (1H, dd, J=9 Hz, 2 Hz), 8.56 (1H, d, J=2 Hz).

EI-Mass (m/z, %): 313 (M+, 56), 298 (100), 258 (16), 244 (35).

IR (v, cm$^{-1}$), KBr: 3408, 3081, 2975, 1620, 1585, 1317.

m.p.: 122 to 125° C.

Example 65

4-Allylamino-2-(1-methyl-2-propenylamino)-6-nitroquinazoline

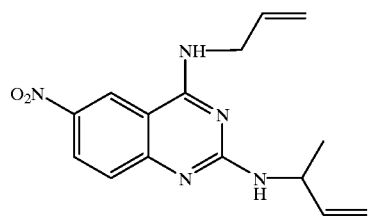

150 mg (0.57 mmol) of 4-allylamino-2-chloro-nitroquinazoline was dissolved in 2 ml of acetonitrile, and then 120 mg (1.12 mmol) of 1-methyl-2-propenylamine hydrochloride and 0.40 ml (2.86 mmol)of triethylamine were added thereto, followed by stirring at 80° C. for 12 hours. Water was added to the reaction solution, followed by extraction with ethyl acetate, washing with brine and drying over anhydrous sodium sulfate. After the solvent was distilled off, the residue was purified by a silica gel column to give 100 mg (58.9%) of the title compound.

NMR (δ, CDCl$_3$): 1.36 (3H, d, J=7 Hz), 4.26 (2H, br), 4.84 (1H, br), 5.08–5.36 (2H, m), 5.80 (1H, br), 5.91–6.07 (2H, m), 7.39 (1H, br), 8.30 (1H, dd, J=9 Hz, 2 Hz), 8.52 (1H, d, J=2 Hz).

EI-Mass (m/z, %): 299 (M+, 46), 284 (100), 252 (7), 238 (36).

IR (v, cm$^{-1}$), KBr: 3402, 3226, 3082, 1620, 1587, 1311.

m.p.: 123 to 124° C.

Test Example

Determination of Oxygen Partial Pressure Increasing Action

Actions of the quinazoline derivatives of the present invention to increase oxygen partial pressure in the arterial blood were determined according to the following method:

Sprague-Dawley male rats having body weights of about 250 g were anesthetized (i.p.) with urethane and cannulated to the respiratory tracts, femoral arteries and femoral veins. An olive oil-charcoal powder suspension (10 mg/ml) was introduced in an amount of 0.8 ml/kg through the respiratory tract cannulae into the lungs to cause the rats to hypoxic state (PaO$_2$ ≦75 mmHg). The quinazoline derivatives listed in Table 1 were intravenously administered to these hypoxemic model rats continuously at a rate of 0.1 mg/kg/min, and arterial blood oxygen partial pressure value (PaO$_2$) of each rat was measured at the time point of 10 minutes after completion of administration using a blood gas analyzer (Ciba Corning 800 series). Gains (ΔPaO$_2$) were determined based on results of PaO$_2$ measurement made before and after administration of the test compounds. The results are shown in Table 1.

TABLE 1

| Example | Compound | ΔPaO$_2$ (mmHg) |
|---|---|---|
| 1 | 2,4-Diallylamino-6-chloroquinazoline | 35 |
| 3 | 2,4-Diallylamino-6-nitroquinazoline | 28 |
| 4 | 4-Allylamino-6-nitro-2-propylaminoquinazoline | 34 |
| 5 | 4-Allylamino-2-neopentylamino-6-nitroquinazoline | 43 |
| 6 | 4-Allylamino-2-benzylamino-6-nitroquinazoline | 48 |
| 7 | 4-Allylamino-2-cyclohexylamino-6-nitroquinazoline | 35 |
| 10 | 2-Allylamino-6-nitro-4-propylaminoquinazoline | 34 |
| 18 | 4-Allylamino-2-isopropylamino-6-nitroquinazoline | 30 |
| 21 | 2-Allylamino-4-methylamino-6-nitroquinazoline | 26 |
| 22 | 2-Allylamino-4-ethylamino-6-nitroquinazoline | 27 |
| 25 | 2-Allylamino-6-nitro-4-pentylaminoquinazoline hydrochloride | 46 |
| 26 | 2-Allylamino-4-heptylamino-6-nitroquinazoline hydrochloride | 46 |
| 27 | 2-Allylamino-4-cyclopentylamino-6-nitroquinazoline hydrochloride | 35 |
| 28 | 2-Allylamino-4-isopropylamino-6-nitroquinazoline hydrochloride | 26 |
| 31 | 4-Allylamino-2-butylamino-6-nitroquinazoline hydrochloride | 36 |
| 33 | 4-Allylamino-2-furfurylamino-6-nitroquinazoline hydrochloride | 42 |
| 34 | 4-Allylamino-2-cyclopentylamino-6-nitroquinazoline hydrochloride | 32 |
| 35 | 4-Allylamino-6-nitro-2-pentylaminoquinazoline hydrochloride | 34 |
| 39 | 2-Allylamino-6-nitro-4-(2-propoxyethylamino)quinazoline | 30 |
| 49 | 2-Allylamino-4-(1-methylpropylamino)-6-nitroquinazoline hydrochloride | 32 |
| 60 | 2-Butylamino-4-(3-ethyl-2-butenylamino)-6-nitroquinazoline | 27 |

Reference Example 16

7-Methylthieno[3,2-d]pyrimidine-2,4(1H,3H)-dione

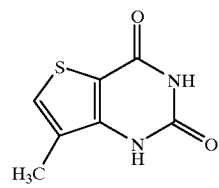

To 25.0 g (146 mmol) of methyl 3-amino-4-methylthiophene-2-carboxylate was added 43.5 g (730 mmol) of urea, and the resulting mixture was heated at 200° C. for 1.5 hours. The mixture was allowed to resume room temperature, and DMF (400 ml) was added thereto, followed by heating under reflux for one hour. After completion of the reaction, ice water was added to the reaction mixture, and crystals thus precipitated were filtered to give 23.0 g (yield: 93.7%) of the title compound.

NMR (δ, DMSO-d$_6$): 2.20 (3H, s), 7.69 (1H, s), 11.24 (2H, br)

Reference Example 17

2,4-Dichloro-7-methylthieno[3,2-d]pyrimidine

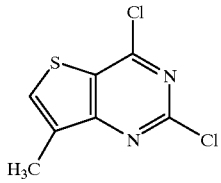

To 18.0 g (107 mmol) of 7-methylthieno[3,2-d]-pyrimidine-2,4(1H,3H)-dione were added 163.0 g (1063 mmol) of phosphorus oxychloride and 12.9 mg (107 mmol) of N,N-dimethylaniline, and the resulting mixture was subjected to heating under reflux for 3 hours. After completion of the reaction, ice water was added to the reaction mixture, and crystals thus precipitated were filtered to give 16.4 g (yield: 74.8%) of the title compound.

NMR (δ, CDCl$_3$): 2.51 (3H, s), 7.75 (1H, s)

Reference Example 18

4-Allylamino-2-chloro-7-methylthieno[3,2-d]pyrimidine

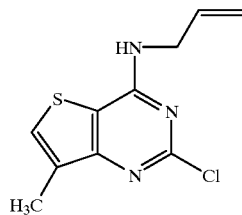

In DMF was dissolved 1.50 g (6.8 mmol) of 2,4-dichloro-7-methylthieno[3,2-d]pyrimidine, and then 917 mg (16.1 mmol) of allylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/8) to give 1.25 g (yield: 76.2%) of the title compound.

NMR (δ, CDCl$_3$): 2.43 (3H, s), 4.28–4.33 (2H, m), 5.09 (1H, br), 5.22–5.35 (2H, m), 5.94–6.07 (1H, m), 7.36 (1H, s)

Example 66

2,4-Diallylamino-7-methylthieno[3,2-d]pyrimidine

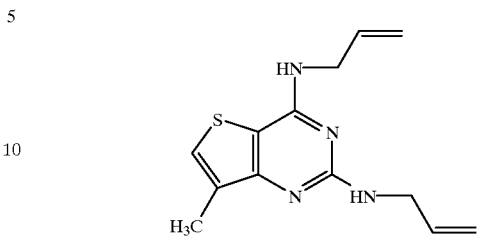

In 2.28 g (40.0 mmol) of allylamine was suspended 250 mg (1.1 mmol) of 4-allylamino-2-chloro-7-methylthieno[3,2-d]pyrimidine, and the resulting mixture was heated in a sealed tube at 140° C. for 24 hours. After the reaction mixture was cooled, 50 ml of water was added thereto, followed by extraction with ethyl acetate (50 ml×3). The organic layer was washed with water and dried over anhydrous sodium sulfate, and then the solvent was distilled off. The residue was purified by silica gel chromatography (eluent: ethyl acetate-hexane=4/1) to give 233 mg (yield: 85.7%) of the title compound.

m.p.: 77 to 80° C.

NMR (δ, CDCl$_3$): 2.32 (3H, s), 4.09–4.16 (2H, m), 4.20–4.25 (2H, m), 4.67 (1H, br), 4.89 (1H, br), 5.08–5.30 (4H, m), 5.93–6.06 (2H, m), 7.17 (1H, s)

IR (ν, cm$^{-1}$), KBr: 3460, 3072, 1564, 1518, 1494

EI-Mass (m/z, %).: 261 (M$^+$+1, 10), 260 (M$^+$, 57), 245 (85)

Reference Example 19

2-Chloro-7-methyl-4-neopentylaminothieno[3,2-d]pyrimidine

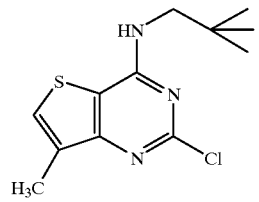

In 3 ml of DMF was dissolved 300 mg (1.4 mmol) of 2,4-dichloro-7-methylthieno[3,2-d]pyrimidine, and after 179 mg (2.1 mmol) of neopentylamine was added to the resulting solution, the mixture was stirred for 3 hours. Water was added to the reaction mixture, and crystals thus precipitated were filtered to give 355 mg (yield: 96.1%) of the title compound.

NMR (δ, CDCl$_3$): 1.02 (H, s), 2.43 (3H, s), 3.51 (2H, d, J=6 Hz), 7.36 (1H, s)

Reference Example 20

4-t-Butylamino-2-chloro-7-methylthieno[3,2-d]
pyrimidine

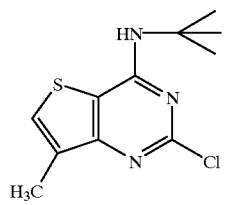

In 3 ml of DMF was dissolved 300 mg (1.4 mmol) of 2,4-dichloro-7-methylthieno[3,2-d]pyrimidine, and after 150 mg (2.1 mmol) of t-butylamine was added to the resulting solution, the mixture was stirred for 3 hours. Water was added to the reaction mixture, and crystals thus precipitated were filtered to give 327 mg (yield: 93.4%) of the title compound.

NMR (δ, CDCl$_3$): 1.57 (9H, s), 2.41 (3H, s), 4.72 (1H, br), 7.29 (1H, s)

Reference Example 21

4-Benzylamino-2-chloro-7-methylthieno[3,2-d]
pyrimidine

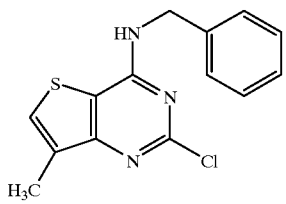

In 3 ml of DMF was dissolved 300 mg (1.4 mmol) of 2,4-dichloro-7-methylthieno[3,2-d]pyrimidine, and after 220 mg (2.1 mmol) of benzylamine was added to the resulting solution, the mixture was stirred for 3 hours. Water was added to the reaction mixture, and crystals thus precipitated were filtered to give 375 mg (yield: 94.5%) of the title compound.

NMR (δ, CDCl$_3$): 2.43 (3H, s), 4.86 (2H, d, J=6 Hz), 5.21 (1H, br), 7–33–7.41 (5H, m)

Reference Example 22

2-Chloro-4-cyclohexylamino-7-methylthieno[3,2-d]
pyrimidine

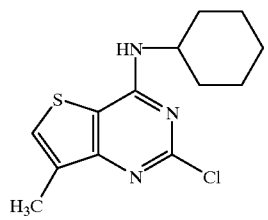

In 3 ml of DMF was dissolved 300 mg (1.4 mmol) of 2,4-dichloro-7-methylthieno [3,2-d]pyrimidine, and after 204 mg (2.1 mmol) of cyclohexylamine was added to the resulting solution, the mixture was stirred for 3 hours. Water was added to the reaction mixture, and crystals thus precipitated were filtered to give 379 mg (yield: 98.2%) of the title compound.

NMR (δ, CDCl$_3$): 1.20–2.14 (10H, m), 2.42 (3H, s), 4.13–4.22 (1H, m), 4.88 (1H, br), 7.34 (1H, s)

Example 67

2-Allylamino-7-methyl-4-neopentylaminothieno [3,2-d]pyrimidine

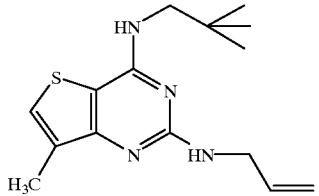

In 2.28 g (40.0 mmol) of allylamine was dissolved 250 mg (0.9 mmol) of 2-chloro-7-methyl-4-neopentylaminothieno [3,2-d]pyrimidine, and the resulting solution was heated in a sealed tube at 140° C. for 24 hours. After the reaction mixture was cooled, 100 ml of water was added thereto, followed by extraction with ethyl acetate (20 ml×3). The organic layer was washed with 20 ml of water and dried over anhydrous sodium sulfate, and then the solvent was distilled off. The residue was purified by silica gel column chromatography (eluent: ethyl acetate-hexane=1/4) to give 165 mg (yield: 61.3%) of the title compound.

m.p.: 90 to 92° C.

NMR (δ, CDCl$_3$): 0.98 (9H, s), 2.32 (3H, s), 3.44 (2H, d, J=6 Hz), 4.09–4.14 (2H, m), 4.63 (1H, br), 4.87 (1H, br), 5.09–5.13 (1H, m), 5.24–5.30 (1H, m), 5.96–6.05 (1H, m), 7.17 (1H, s)

IR (ν, cm$^{-1}$), KBr: 3440, 2960, 1564, 1530, 1466, 794

EI-Mass (m/z, %): 291 (M$^+$+1, 11), 290 (M$^+$, 58), 275 (100)

Example 68

2-Allylamino-4-t-butylamino-7-methylthieno[3,2-d]
pyrimidine

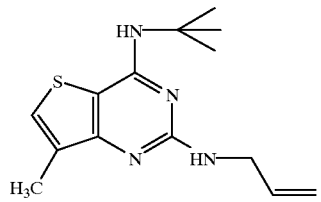

In 2.28 g (40.0 mmol) of allylamine was dissolved 250 mg (1.0 mmol) of 4-t-butylamino-2-chloro-7-methylthieno[3,2-d]pyrimidine, and the resulting solution was heated in a sealed tube at 140° C. for 24 hours. After the reaction mixture was cooled, 100 ml of water was added thereto, followed by extraction with ethyl acetate (20 ml×3). The organic layer was washed with 20 ml of water and dried over anhydrous sodium sulfate, and then the solvent was distilled off. The residue was purified by silica gel column chromatography (eluent: ethyl acetate-hexane=1/4) to give 247 mg (yield: 91.5%) of the title compound.

m.p.: 89 to 90° C.

NMR (δ, CDCl$_3$): 1.54 (9H, s), 2.30 (3H, s), 4.09–4.14 (2H, m), 4.40 (1H, br), 4.90 (1H, br), 5.08–5.12 (1H, m), 5.22–5.30 (1H, m), 5.94–6.07 (1H, m), 7.12 (1H, s)

IR (v, cm$^{-1}$), KBr: 3448, 3236, 2976, 1588, 1514, 1484, 1456, 796

EI-Mass (m/z, %): 277 (M$^+$+1, 16), 276 (M$^+$, 75), 261 (67), 219 (36), 205 (100)

Example 69

2-Allylamino-4-benzylamino-7-methylthieno[3,2-d]pyrimidine

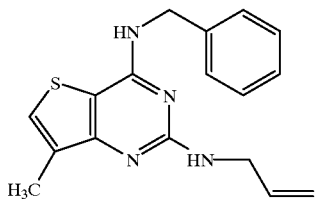

In 2.28 g (40.0 mmol) of allylamine was dissolved 250 mg (0.9 mmol) of 4-benzylamino-2-chloro-7-methylthieno[3,2-d]pyrimidine, and the resulting solution was heated in a sealed tube at 140° C. for 24 hours. After the reaction mixture was cooled, 100 ml of water was added thereto, followed by extraction with ethyl acetate (20 ml×3). The organic layer was washed with 20 ml of water and dried over anhydrous sodium sulfate, and then the solvent was distilled off. The residue was purified by silica gel column chromatography (eluent: ethyl acetate-hexane=1/4) to give 217 mg (yield: 81.3%) of the title compound.

m.p.: 97 to 98° C.

NMR (δ, CDCl$_3$): 2.33 (3H, s), 4.09–4.14 (2H, ml), 4.80 (2H, d, J=6 Hz), 4.89–4.91 (2H, m), 5.07–5.11 (1H, m), 5.22–5.29 (1H, m), 5.92–6.03 (1H, m), 7.17 (1H, s), 7.27–7.40 (5H, m)

IR (v, cm$^{-1}$), KBr: 3456, 1580, 1518, 1452, 704

EI-Mass (m/z, %): 311 (M$^+$+1, 17), 310 (M$^+$, 81), 296 (100)

Example 70

2-Allylamino-4-cyclohexylamino-7-methylthieno[3,2-d]pyrimidine hydrochloride

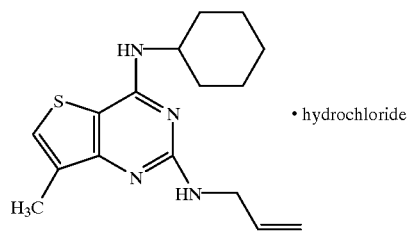

In 2.28 g (40.0 mmol) of allylamine was dissolved 250 mg (0.9 mmol) of 2-chloro-4-cyclohexylamino-7-methylthieno[3,2-d]pyrimidine, and the resulting solution was heated in a sealed tube at 140° C. for 24 hours. After the reaction mixture was cooled, 100 ml of water was added thereto, followed by extraction with ethyl acetate (20 ml×3). The organic layer was washed with 20 ml of water and dried over anhydrous sodium sulfate, and then the solvent was distilled off. The residue was purified by silica gel column chromatography and an eluate of hexane/ethyl acetate=4/1 was concentrated. To the concentrate was added a 4N hydrochloric acid-ethyl acetate solution (1 ml), and crystals thus precipitated were filtered to give 200 mg (yield: 66.7%) of the title compound.

m.p.: 140 to 142° C.

NMR (δ, CDCl$_3$): 1.21–2.11 (10H, mn), 2.51 (3H, s), 4.09–4.17 (3H, m), 5.17–5.20 (1H, m), 5.31–5.36 (1H, m), 5.62–5.64 (1H, m), 5.84–5.97 (1H, m), 7.31 (1H, s), 8.57 (1H, br), 14.08 (1H, br)

IR (v, cm$^{-1}$), KBr: 2940, 1634, 1602, 1568, 1362, 786

EI-Mass (m/z, %): 303 (M$^+$+1, 15), 302 (M$^+$, 69), 287 (100)

Reference Example 23

4-Diallylamino-2-chloro-7-methylthieno [3, 2-d]pyrimidine

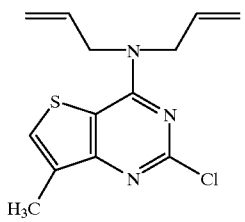

In DMF was dissolved 1.50 g (6.8 mmol) of 2,4-dichloro-7-methylthieno[3,2-d]pyrimidine, and then 1.56 9 (16.1 mmol) of diallylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane= 1:15) to give 1.17 g (yield: 61.1%) of the title compound.

NMR (δ, CDCl$_3$): 2.41 (3H, s), 4.38 (4H, d, J=5 Hz), 5.19–5.26 (4H, m), 5.87–6.00 (2H, m), 7.38 (1H, s)

Example 71

2-Allylamino-4-diallylamino-7-methylthieno[3,2-d]pyrimidine hydrochloride

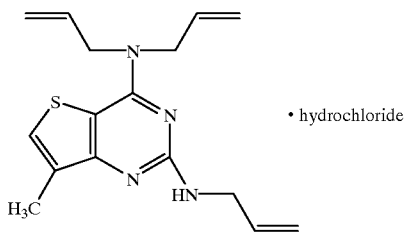

In a sealed tube were heated 335 mg (1.2 mmol) of 4-diallylamino-2-chloro-7-methylthieno[3,2-d]pyrimidine and 1.10 g (19.2 mmol) of allylamine at 140° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel column chromatography (eluent: ethyl acetate-hexane=1/4) to give 277 mg (yield: 77.0%) of a free base compound of the title compound.

NMR (δ, CDCl$_3$): 2.31 (3H, s), 4.07–4.11 (2H, m), 4.32 (4H, d, J=5 Hz), 4.88 (1H, br), 5.08–5.28 (6H, m), 5.88–6.04 (3H, m), 7.20 (1H, d, J=1 Hz)

To a solution of 277 mg of the free base compound of the title compound in ethyl acetate was added dropwise under ice cooling a 4N hydrochloric acid-ethyl acetate solution (1 ml). Crystals thus precipitated were filtered to give 270 mg of the title compound.

m.p.: 76 to 78° C. (decomp.)

NMR (δ, CDCl$_3$): 2.53 (3H, s), 4.06–4.11 (2H, m), 4.38 (4H, d, J=5 Hz), 5.15–5.36 (6H, m), 5.84–5.97 (3H, m), 7.40 (1H, s), 8.69 (1H, br), 14.22 (1H, br)

IR (ν, cm$^{-1}$), KBr: 2923, 2856, 1631, 1536, 926, 746

EI-Mass (m/z, %): 301 (M$^+$+1, 14), 300 (M$^+$, 66) 285 (36), 259 (100), 217 (41)

Example 72

4-Allylamino-2-diallylamino-7-methylthieno[3,2-d]pyrimidine hydrochloride

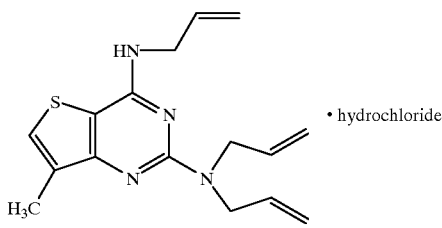

In a sealed tube were heated 287 mg (1.2 mmol) of 4-allylamino-2-chloro-7-methylthieno[3,2-d]pyrimidine and 1.87 g (19.2 mmol) of diallylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/4) to give 193 mg (yield: 53.7%) of a free base compound of the title compound.

NMR (δ, CDCl$_3$): 2.31 (3H, s), 4.18–4.23 (2H, m), 4.29 (4H, d, J=6 Hz), 4.59 (1H, br), 5.09–5.29 (6H, m), 5.86–6.06 (3H, m), 7.14 (1H, s)

To a solution of 193 mg of the free base compound of the title compound in ethyl acetate was added dropwise under ice cooling a 4N hydrochloric acid-ethyl acetate solution (1 ml). Crystals thus precipitated were filtered to give 193 mg of the title compound.

m.p.: 136 to 138° C. (decomp.)

NMR (δ, CDCl$_3$): 2.54 (3H, s), 4.12 (2H, br), 4.53 (4H, br), 5.16–5.42 (6H, m), 5.81–6.02 (3H, m), 7.40 (1H, br), 9.03 (1H, br), 11.48 (1H, br)

IR (ν, cm$^{-1}$), KBr: 3330, 3080, 1610, 1581, 1382, 995, 937

EI-Mass (m/z, %): 301 (M$^+$+1, 13), 300 (M$^+$, 63), 285 (33), 259 (100)

Reference Example 24

2-Chloro-4-(1,3-dihydroxypropan-2-yl)amino-7-methylthieno[3,2-d]pyrimidine

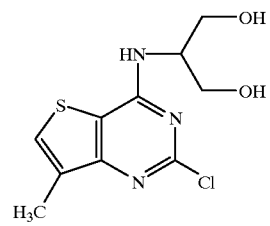

In 8 ml of DMF was dissolved 1.0 g (4.6 mmol) of 2,4-dichloro-7-methylthieno[3,2-d]pyrimidine, and then 977 mg (10.7 mmol) of 2-amino-1,3-propanediol was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/2) to give 903 mg (yield: 72.3%) of the title compound.

NMR (δ, DMSO-d$_6$): 2.28 (3H, s), 3.52–3.61 (4H, m), 4.26–4.34 (1H, m), 4.73 (2H, t, J=6 Hz), 7.80 (1H, s), 7.90 (1H, d, J=8 Hz)

Example 73

2-Allylamino-4-(1,3-dihydroxypropan-2-yl)amino-7-methylthieno[3,2-d]pyrimidine

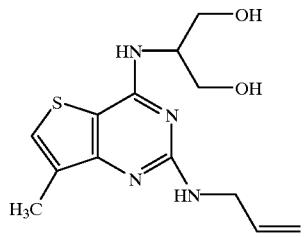

In a sealed tube were heated 328 mg (1.2 mmol) of 2-chloro-4-(1,3-dihydroxypropan-2-yl)amino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane =1/1) to give 293 mg (yield: 83.2%) of the title compound.

m.p.: 163 to 164° C.

NMR (δ, DMSO-$d_6$): 2.18 (3H, s), 3.57 (4H, dd, J=5 Hz, 5 Hz), 3.93 (2H, br), 4.20–4.27 (1H, m), 4.63 (2H, dd, J=5 Hz, 5 Hz), 5.01 (1H, d, J=10 Hz), 5.17 (1H, d, J=17 Hz), 5.86–5.99 (1H, m), 6.48 (1H, br), 6.69 (1H, d, J=8 Hz), 7.47 (1H, s)

IR (ν, cm$^{-1}$), KBr: 3401, 1604, 1565, 1527, 1049, 787

EI-Mass (m/z, %): 295 (M$^+$+1, 10), 294 (M$^+$, 52), 279 (61), 263 (40), 205 (41), 66 (100)

Example 74

2-Diallylamino-4-cyclohexylamino-7-methylthieno[3,2-d]pyrimidine

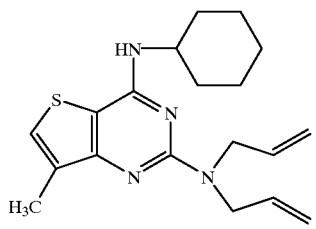

In a sealed tube were heated 338 mg (1.2 mmol) of 2-chloro-4-cyclohexylamino-7-methylthieno[3,2-d]pyrimidine and 1.87 g (19.2 mmol) of diallylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/2) to give 298 mg (yield: 72.7%) of the title compound.

NMR (δ, CDCl$_3$): 1.19–1.47 (4H, m), 1.63–1.81 (4H, m), 2.09–2.13 (2H, m), 2.30 (3H, s), 4.01–4.12 (1H, m), 4.28 (4H, d, J=6 Hz), 4.38–4.41 (1H, m), 5.09–5.21 (4H, m), 5.86–5.99 (2H, m), 7.12 (1H, s)

IR (ν, cm$^{-1}$), film: 3425, 2931, 2854, 1574, 1527, 1496, 1265, 756

EI-Mass (m/z, %): 343 (M$^+$+1, 13), 342 (M$^+$, 56), 327 (31), 301 (100), 219 (58)

Reference Example 25

2-Chloro-7-methyl-4-(4-methylpiperidino)thieno[3,2-d]pyrimidine

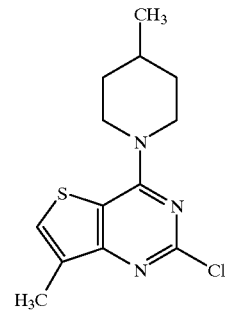

In 10 ml of DMF was dissolved 1.0 g (4.6 mmol) of 2,4-dichloro-7-methylthieno[3,2-d]pyrimidine, and then 1.06 g (10.7 mmol) of 4-methylpiperidine was added dropwise to the resulting solution under ice cooling over 5 minutes. The reaction mixture was stirred at 0° C. for one hour and then allowed to resume to room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 1.20 g (yield: 93.3%) of the title compound.

NMR (δ, CDCl$_3$): 0.99 (3H, d, J=6 Hz), 1.21–1.30 (2H, m), 1.70–1.84 (3H, m), 2.41 (3H, s), 3.07–3.16 (2H, m), 4.75–4.81 (2H, m), 7.36 (1H, s)

Example 75

2-Allylamino-7-methyl-4-(4-methylpiperidino)thieno[3,2-d]pyrimidine

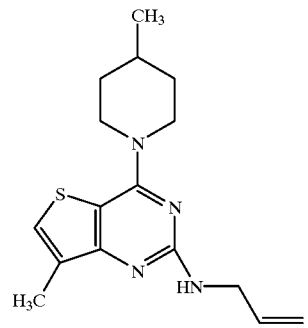

In a sealed tube were heated 422 mg (1.5 mmol) of 2-chloro-7-methyl-4-(4-methylpiperidino)thieno[3,2-d]

pyrimidine and 1.37 g (24.0 mmol) of diallylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/6) to give 198 mg (yield: 43.9%) of the title compound.

NMR (δ, CDCl$_3$): 0.96 (3H, d, J=6 Hz), 1.18–1.31 (2H, m), 1.62–1.77 (3H, m), 2.31 (3H, s), 2.97–3.06 (2H, m), 4.08–4.12 (2H, m), 4.70–4.75 (2H, m), 4.81 (1H, br), 5.07–5.12 (1H, m), 5.22–5.29 (1H, m), 5.94–6.07 (1H, m), 7.19 (1H, s)

IR (ν, cm$^{-1}$), film: 2947, 2923, 1550, 1520, 1450, 756

EI-Mass (m/z, %): 303 (M$^+$+1, 11), 302 (M$^+$, 55), 287 (100)

Reference Example 26

2-Chloro-4-ethylamino-7-methylthieno[3,2-d]pyrimidine

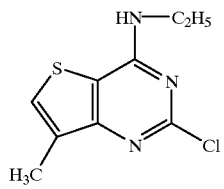

In DMF was dissolved 700 mg (3.2 mmol) of 2,4-dichloro-7-methylthieno[3,2-d]pyrimidine, and then an aqueous solution of 338 mg (7.5 mmol) of ethylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/6) to give 524 mg (yield: 72.0%) of the title compound.

NMR (δ, CDCl$_3$): 1.34 (3H, t, J=7 Hz), 2.42 (3H, s), 3.68–3.74 (2H, m), 4.97 (1H, br), 7.35 (1H, s)

Example 76

2-Allylamino-4-ethylamino-7-methylthieno[3,2-d]pyrimidine

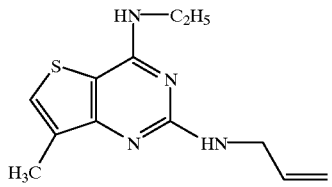

In a sealed tube were heated 273 mg (1.2 mmol) of 2-chloro-4-ethylamino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/2) to give 191 mg (yield: 64.3%) of the title compound.

m.p.: 96 to 97° C.

NMR (δ, CDCl$_3$): 1.29 (3H, t, J=7 Hz), 2.32 (3H, s), 3.58–3.65 (2H, m), 4.11–4.15 (2H, m), 4.57 (1H, br), 4.87 (1H, br), 5.09–5.12 (1H, m), 5.24–5.30 (1H, m), 5.96–6.06 (1H, m), 7.15 (1H, s)

IR (ν, cm$^{-1}$), KBr: 3433, 2970, 1597, 1566, 1519, 1349, 795

EI-Mass (m/z, %): 249 (M$^+$+1, 9), 248 (M$^+$, 52), 233 (100)

Reference Example 27

2-Chloro-4-isopropylamino-7-methylthieno[3,2-d]pyrimidine

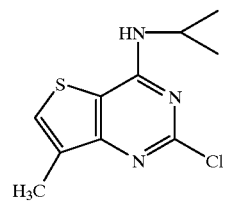

In DMF was dissolved 700 mg (3.2 mmol) of 2,4-dichloro-7-methylthieno[3,2-d]pyrimidine, and then an aqueous solution of 443 mg (7.5 mmol) of isopropylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/6) to give 636 mg (yield: 82.4%) of the title compound.

NMR (δ, CDCl$_3$): 1.33 (6H, d, J=6 Hz), 2.42 (3H, s), 4.49–4.57 (1H, m), 4.81 (1H, br), 7.34 (1H, s)

Example 77

2-Allylamino-4-isopropylamino-7-methylthieno[3,2-d]pyrimidine

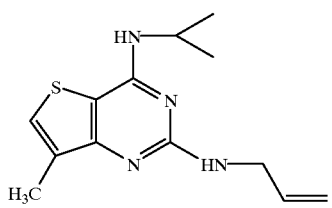

In a sealed tube were heated 290 mg (1.2 mmol) of 2-chloro-4-isopropylamino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/4) to give 244 mg (yield: 77.7%) of the title compound.

m.p.: 106 to 107° C.

NMR (δ, CDCl$_3$): 1.29 (6H, d, J=6 Hz), 2.32 (3H, s), 4.10–4.14 (2H, m), 4.40–4.48 (2H, m), 4.86–4.88 (1H, m), 5.08–5.12 (1H, m), 5.24–5.29 (1H, m), 5.96–6.05 (1H, m), 7.15 (1H, s)

IR (ν, cm$^{-1}$), KBr: 3425, 3232, 2970, 1589, 1565, 1519, 1465, 918, 795

EI-Mass (m/z, %): 263 (M$^+$+1, 14), 262 (M$^+$, 78), 247 (100), 205 (51)

Reference Example 28

2-Chloro-4-cyclopropylamino-7-methylthieno[3,2-d]pyrimidine

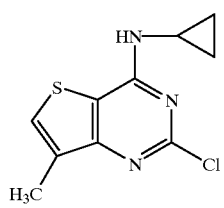

In DMF was dissolved 700 mg (3.2 mmol) of 2,4-dichloro-7-methylthieno[3,2-d]pyrimidine, and then an aqueous solution of 428 mg (7.5 mmol) of cyclopropylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/6) to give 780 mg (yield: 95.4%) of the title compound.

NMR (δ, CDCl$_3$): 0.76–0.80 (2H, m), 0.95–1.04 (2H, m), 2.42 (3H, s), 3.02–3.08 (1H, m), 5.68 (1H, br), 7.47 (1H, s)

Example 78

2-Allylamino-4-cyclopropylamino-7-methylthieno[3,2-d]pyrimidine

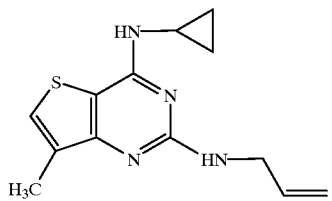

In a sealed tube were heated 287 g (1.2 mmol) of 2-chloro-4-cyclopropylamino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/4) to give 265 mg (yield: 84.9%) of the title compound.

NMR (δ, CDCl$_3$): 0.70–0.73 (2H, m), 0.88–0.92 (2H, m), 2.32 (3H, s), 2.95–2.96 (1H, m), 4.10–4.13 (2H, m), 4.82 (1H, br), 5.09–5.12 (2H, m), 5.24–5.29 (1H, m), 5.94–6.05 (1H, m), 7.24 (1H, s)

IR (ν, cm$^{-1}$), film: 3263, 1565, 1511, 1349, 756

EI-Mass (m/z, %): 261 (M$^+$+1, 14), 260 (M$^+$, 77), 245 (100)

Reference Example 29

4-(1-Adamantylamino)-2-chloro-7-methylthieno[3,2-d]pyrimidine

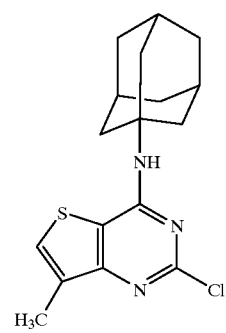

In DMF was dissolved 700 mg (3.2 mmol) of 2,4-dichloro-7-methylthieno[3,2-d]pyrimidine, and then an aqueous solution of 1.13 g (7.5 mmol) of 1-adamantaneamine was added dropwise to the resulting rid solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane= 1/10) to give 1.10 g (yield: 100%) of the title compound.

NMR (δ, CDCl$_3$): 1.67–1.78 (7H, m), 2.08–2.23 (8H, m), 2.40 (3H, s), 4.61 (1H, br), 7.38 (1H, s)

Example 79

4-(1-Adamantylamino)-2-allylamino-7-methylthieno[3,2-d]pyrimidine

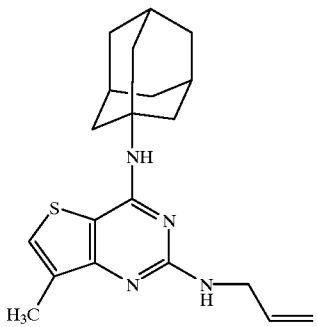

In a sealed tube were heated 400 mg (1.2 mmol) of 4-(1-adamantylamino)-2-chloro-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/4) to give 292 mg (yield: 68.7%) of the title compound.

m.p.: 107 to 109° C.

NMR (δ, CDCl$_3$): 1.63 (2H, brs), 1.71–1.73 (5H, m), 2.13 (3H, br), 2.22–2.23 (5H, m), 2.30 (3H, s), 4.09–4.13 (2H, m), 4.30 (1H, br), 4.88 (1H, br), 5.09–5.13 (1H, m), 5.23–5.29 (1H, m), 5.97–6.06 (1H, m), 7.11 (1H, s)

IR (ν, cm$^{-1}$), KBr: 3248, 2908, 2854, 1581, 1519, 1450, 1357, 795

EI-Mass (m/z, %): 355 (M$^+$+1, 15), 354 (M$^+$, 58), 339 (100), 205 (16)

Reference Example 30

2-Chloro-4-nonylamino-7-methylthieno[3,2-d]pyrimidine

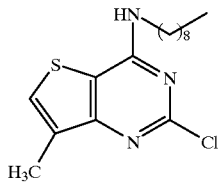

In DMF was dissolved 700 mg (3.2 mmol) of 2,4-dichloro-7-methylthieno[3,2-d]pyrimidine, and then an aqueous solution of 1.07 g (7.5 mmol) of n-nonylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 1.10 g (yield: 100%) of the title compound.

NMR (δ, CDCl$_3$): 0.88 (3H, t, J=7 Hz), 1.24–1.45 (12H, m), 1.65–1.72 (2H, m), 2.42 (3H, s), 3.63–3.68 (2H, m), 4.98 (1H, br), 7.35 (1H, s)

Example 80

2-Allylamino-4-nonylamino-7-methylthieno[3,2-d]pyrimidine

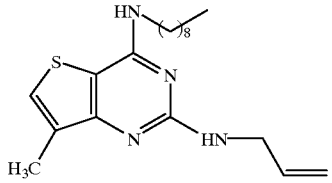

In a sealed tube were heated 391 mg (1.2 mmol) of 2-chloro-4-nonylamino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/10) to give 238 mg (yield: 57.2%) of the title compound.

m.p.: 65 to 66° C.

NMR (δ, CDCl$_3$): 0.88 (3H, t, J=7 Hz), 1.27–1.40 (12H, m), 1.61–1.68 (2H, m), 2.32 (3H, s), 3.54–3.59 (2H, m), 4.11–4.14 (2H, m), 4.59 (1H, br), 4.86 (1H, br), 5.08–5.12 (1H, m), 5.24–5.29 (1H, m), 5.96–6.05 (1H, m), 7.15 (1H, s)

IR (ν, cm$^{-1}$), KBr: 3421, 2924, 2856, 1597, 1571, 1522, 1462, 791

EI-Mass (m/z, %): 347 (M$^+$+1, 16), 346 (M$^+$, 66), 331 (100), 205 (22)

Reference Example 31

4-Butylamino-2-chloro-7-methylthieno[3,2-d]pyrimidine

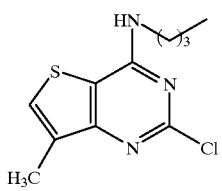

In DMF was dissolved 700 mg (3.2 mmol) of 2,4-dichloro-7-methylthieno[3,2-d]pyrimidine, and then an aqueous solution of 548 mg (7.5 mmol) of butylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 698 mg (yield: 85.4%) of the title compound.

NMR (δ, CDCl$_3$): 0.98 (3H, t, J=7.3 Hz), 1.41–1.50 (2H, m), 1.64–1.72 (2H, m), 2.42 (3H, s), 3.64–3.69 (2H, m), 4.99 (1H, br), 7.35 (1H, s)

Example 81

2-Allylamino-4-butylamino-7-methylthieno[3,2-d]pyrimidine

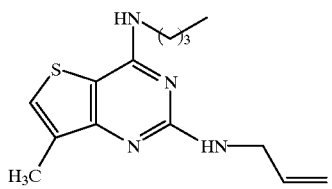

In a sealed tube were heated 307 mg (1.2 mmol) of 4-butylamino-2-chloro-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/8) to give 245 mg (yield: 73.8%) of the title compound.

m.p.: 68 to 70° C.

NMR (δ, CDCl$_3$): 0.96 (3H, t, J=7.3 Hz), 1.38–1.47 (2H, m), 1.60–1.72 (2H, m), 2.32 (3H, s), 3.55–3.60 (2H, m), 4.11–4.14 (2H, m), 4.59 (1H, br), 4.85–4.87 (1H, m), 5.09–5.12 (1H, m), 5.24–5.29 (1H, m), 5.96–6.05 (1H, m), 7.15 (1H, s)

IR (ν, cm$^{-1}$), KBr: 3448, 2928, 1594, 1564, 1528, 1466, 1348, 1284, 790

EI-Mass (m/z, %): 277 (M$^+$+1, 13), 276 (M$^+$, 68), 261 (100), 205 (19)

Reference Example 32

2-Chloro-7-methyl-4-pentylaminothieno[3,2-d]pyrimidine

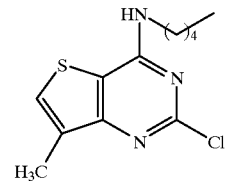

In DMF was dissolved 700 mg (3.2 mmol) of 2,4-dichloro-7-methylthieno[3,2-d]pyrimidine, and then an aqueous solution of 654 mg (7.5 mmol) of pentylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 788 mg (yield: 91.4%) of the title compound.

NMR (δ, CDCl$_3$): 0.91–0.95 (3H, m), 1.36–1.42 (4H, m), 1.66–1.73 (2H, m), 2.42 (3H, s), 3.63–3.68 (2H, m), 4.98 (1H, br), 7.35 (1H, s)

Example 82

2-Allylamino-7-methyl-4-pentylaminothieno[3,2-d]pyrimidine

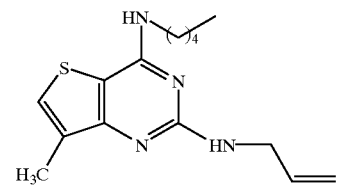

In a sealed tube were heated 391 mg (1.2 mmol) of 2-chloro-7-methyl-4-pentylaminothieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/8) to give 184 mg (yield: 52.9%) of the title compound.

m.p.: 64 to 65° C.

NMR (δ, CDCl$_3$): 0.92 (3H, t, J=7.1 Hz), 1.36–1.40 (4H, m), 1.62–1.69 (2H, m), 2.32 (3H, s), 3.54–3.59 (2H, m), 4.11–4.14 (2H, m), 4.60 (1H, br), 4.86 (1H, br), 5.09–5.12 (1H, m), 5.24–5.29 (1H, m), 5.96–6.05 (1H, m), 7.15 (1H, s).

IR (ν, cm⁻¹), KBr: 3452, 2928, 1590, 1564, 1520, 1464, 1382, 1284, 792

EI-Mass (m/z, %): 291 (M⁺+1, 12), 290 (M⁺, 64), 275 (100), 205 (17)

Reference Example 33

2-Chloro-4-heptylamino-7-methylthieno[3,2-d]pyrimidine

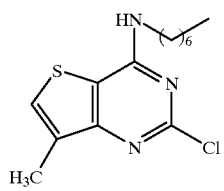

In DMF was dissolved 700 mg (3.2 mmol) of 2,4-dichloro-7-methylthieno[3,2-d]pyrimidine, and then an aqueous solution of 1.07 g (7.5 mmol) of heptylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/8) to give 1.00 g (yield: 100%) of the title compound.

NMR (δ, CDCl₃): 0.89 (3H, t, J=6.8 Hz), 1.28–1.45 (8H, m), 1.65–1.73 (2H, m), 2.42 (3H, s), 3.63–3.68 (2H, m), 5.01 (1H, br), 7.35 (1H, s)

Example 83

2-Allylamino-4-heptylamino-7-methylthieno[3,2-d]pyrimidine

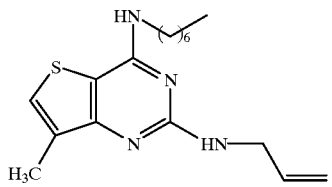

In a sealed tube were heated 82 mg (1.2 mmol) of 2-chloro-4-heptylamino-7-methylthieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/10) to give 261 mg (yield: 68.3%) of the title compound.

m.p.: 56 to 57° C.

NMR (δ, CDCl₃): 0.89 (3H, t, J=6.9 Hz), 1.28–1.42 (8H, m), 1.61–1.68 (2H, m), 2.32 (3H, s), 3.54–3.59 (2H, m), 4.11–4.14 (2H, m), 4.62 (1H, br), 4.87 (1H, br), 5.08–5.12 (1H, m), 5.24–5.29 (1H, m), 5.95–6.05 (1H, m), 7.15 (1H, s)

IR (ν, cm⁻¹), KBr: 3460, 2920, 1592, 1564, 1526, 1468, 1354, 834

EI-Mass (m/z, %): 319 (M⁺+1, 14), 318 (M⁺, 67), 303 (100), 205 (17)

Reference Example 34

2-Chloro-7-methyl-4-(1-methylpropylamino)thieno[3,2-d]pyrimidine

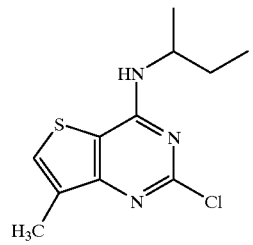

In DMF was dissolved 700 mg (3.2 mmol) of 2,4-dichloro-7-methylthieno[3,2-d]pyrimidine, and then an aqueous solution of 1.07 g (7.5 mmol) of 1-methylpropylamine was added dropwise to the resulting solution under ice cooling over 5 minutes. The reaction mixture was stirred at 0° C. for one hour and then allowed to resume room temperature, followed by stirring for one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/8) to give 676 mg (yield: 82.7%) of the title compound.

NMR (δ, CDCl₃): 0.99 (3H, t, J=7.4 Hz), 1.29 (3H, d, J=6.6 Hz), 1.61–1.68 (2H, m), 2.42 (3H, s), 4.33–4.40 (1H, m), 4.77 (1H, br), 7.35 (1H, s)

Example 84

2-Allylamino-7-methyl-4-(1-methylpropylamino)thieno[3,2-d]pyrimidine

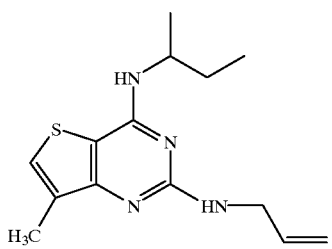

In a sealed tube were heated 307 mg (1.2 mmol) of 2-chloro-7-methyl-4-(1-methylpropylamino)thieno[3,2-d]pyrimidine and 1.10 g (19.2 mmol) of allylamine at 160° C. for 16 hours. After completion of the reaction, the reaction mixture was allowed to resume room temperature, and a saturated aqueous sodium hydrogen carbonate solution was added thereto, followed by extraction with ethyl acetate (50 ml×2). The organic layer was washed with brine and dried over anhydrous sodium sulfate, and then the solvent was distilled off under reduced pressure. The residue was purified by silica gel chromatography (eluent: ethyl acetate-hexane=1/10) to give 266 mg (yield: 80.1%) of the title compound.

m.p.: 91 to 92° C.

NMR (δ, CDCl$_3$): 0.96 (3H, t, J=7.4 Hz), 1.25 (3H, d, J=6.4 Hz), 1.54–1.68 (2H, m), 2.32 (3H, s), 4.09–4.13 (2H, m), 4.24–4.31 (1H, m), 4.36–4.38 (1H, m), 4.84–4.86 (1H, m), 5.08–5.12 (1H, m), 5.23–5.29 (1H, m), 5.95–6.05 (1H, m), 7.15 (1H, s)

IR (ν, cm$^{-1}$), KBr: 3448, 1588, 1564, 1514, 1466, 1372, 1278, 840

EI-Mass (m/z, %): 277 (M$^+$+1, 13), 276 (M$^+$, 68), 261 (100), 247 (25), 219 (13), 205 (38)

Example 85

4-Allylamino-2-(2-methoxyethylamino)-7-methylthieno[3,2-d]pyrimidine

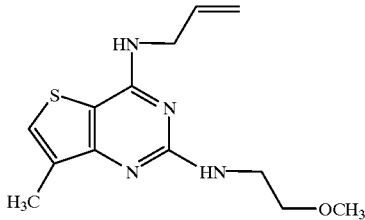

287 mg (1.2 mmol) of 4-allylamino-2-chloro-7-methylthieno[3,2-d]pyrimidine and 1.44 mg (19.2 mmol) of 2-methoxyethylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 274 mg (yield: 82.3%) of the title compound.

m.p.: 87 to 88° C.

NMR (δ, CDCl$_3$): 2.32(3H, s), 3.39(3H, s), 3.57–3.60(2H, m), 3.65–3.70(2H, m), 4.20–4.24(2H, m), 4.66(1H, br), 5.15–5.30(3H, m), 5.93–6.08(1H, m), 7.40(1H, br), 7.16 (1H, s).

IR (ν, cm$^{-1}$), KBr: 3417, 2924, 1589, 1558, 1519, 1457, 1342, 1103, 794.

EI-Mass (m/z, %): 279(M$^+$+1, 5), 278(M$^+$, 26), 263(17), 233(100), 220(47), 205(29)

Example 86

4-Allylamino-7-methyl-2-propylaminothieno[3,2-d]pyrimidine

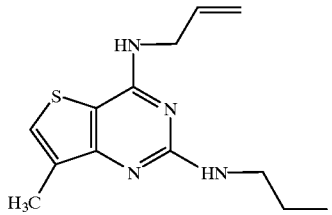

288 mg (1.2 mmol) of 4-allylamino-2-chloro-7-methylthieno[3,2-d]pyrimidine and 1.13 mg (19.2 mmol) of propylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by a silica gel chromatography (eluent: ethyl acetate-hexane=1/2) to give 126 mg (yield: 60.0%) of the title compound.

m.p.: 74 to 75° C.

NMR (δ, CDCl$_3$): 0.99 (3H, t, J=7.5 Hz), 1.59–1.68 (2H, m), 2.32 (3H, s), 3.40–3.45 (2H, m), 4.21–4.25 (2H, m), 4.65 (1H, br), 4.85 (1H, br), 5.15–5.19 (1H, m), 5.25–5.30 (1H, m), 5.95–6.05 (1H, m), 7.16 (1H, s).

IR (ν, cm$^{-1}$), KBr: 3448, 1596, 1566, 1528, 1464, 838

EI-Mass (m/z, %): 263 (M$^+$+1, 14), 262 (M$^+$, 85), 247 (43), 233 (100), 205 (71)

Reference Example 35

2-Chloro-7-methyl-4-piperidinoaminothieno[3,2-d]pyrimidine

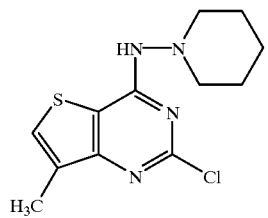

In DMF (N,N-dimethylformamide) was dissolved 700 mg (3.4 mmol) of 2,4-dichloro-7-methylthieno[3,2-d]pyrimidine, and then a solution of 751 mg (7.5 mmol) of 1-aminopiperidine was added dropwise to the resulting solution under ice cooling over 5 minutes. The reaction solution was stirred at 0° C. for one hour and then allowed to resume room temperature, followed by stirring for further one hour. After completion of the reaction, ice go water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/8) to give 573 mg (yield: 59.4%) of the title compound.

NMR (δ, CDCl₃): 1.20–1.28 (1H, m), 1.76–1.91 (5H, m), 2.41 (3H, s), 2.44–2.49 (2H, m), 3.17–3.20 (2H, m), 6.46 (1H, s), 7.46 (1H, s)

Example 87

2-Allylamino-7-methyl-4-piperidinoaminothieno[3,2-d]pyrimidine

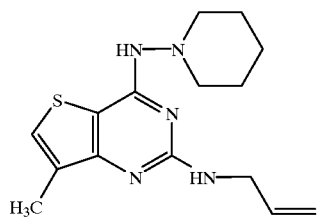

339 mg (1.2 mmol) of 2-chloro-7-methyl-4-piperidinoaminothieno[3,2-d]pyrimidine and 1.10 g (19.2 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by a silica gel chromatography (eluent: ethyl acetate-hexane=1/2) to give 233 mg (yield: 64.0%) of the title compound.

NMR (δ, CDCl₃): 1.20 (1H, br), 1.73–1.84 (5H, m), 2.31 (3H, s), 2.37 (2H, br), 3.19 (2H, br), 4.08–4.11 (2H, m), 4.74–4.76 (1H, m), 5.08–5.12 (1H, m), 5.23–5.29 (1H, m), 5.86 (1H, s), 5.94–6.04 (1H, m), 7.27 (1H, s).

IR (ν, cm⁻¹), KBr: 3292, 2944, 1568, 1504, 1446, 798

EI-Mass (m/z, %): 304 (M⁺+1, 10), 303 (M⁺, 56), 220 (62), 205 (100)

Reference Example 36

2-Chloro-7-methyl-4-(2,2-dimethylhydrazino)thieno[3,2-d]pyrimidine

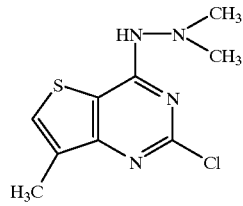

In DMF was dissolved 700 mg (3.4 mmol) of 2,4-dichloro-7-methylthieno[3,2-d]pyrimidine, and then a solution of 450 mg (7.5 mmol) of 1,1-dimethylhydrazine was added dropwise to the resulting solution under ice cooling over 5 minutes. The reaction solution was stirred at 0° C. for one hour and then allowed to resume room temperature, followed by stirring for further one hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatog-raphy (eluent: ethyl acetate-hexane=1/4) to give 173 mg (yield: 20.9%) of the title compound.

NMR (δ, CDCl₃): 2.41 (3H, s), 2.68 (6H, s), 6.34 (1H, br), 7.47 (1H, s).

Example 88

2-Allylamino-7-methyl-4-(2,2-dimethylhydrazino)thieno[3,2-d]pyrimidine

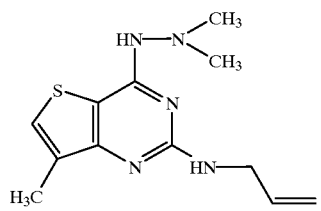

150 mg (0.62 mmol) of 2-chloro-7-methyl-4-(2,2-dimethylhydrazino)thieno[3,2-d]pyrimidine and 564 mg (9.89 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by a silica gel chromatography (eluent: ethyl acetate-hexane=1/2) to give 151 mg (yield: 92.6%) of the title compound.

NMR (δ, CDCl₃): 2.31 (3H, s), 2.64 (6H, s), 4.07–4.11 (2H, m), 4.78 (1H, br), 5.09–5.12 (1H, m), 5.23–5.29 (1H, m), 5.76 (1H, br), 5.94–6.03 (1H, m), 7.29 (1H, s).

IR (ν, cm⁻¹), KBr: 3276, 1574, 1506, 1450, 800.

EI-Mass (m/z, %): 264 (M⁺+1, 9), 263 (M⁺, 58), 220 (36), 205 (100)

Reference Example 37

4-(2-t-Butylhydrazino)-2-chloro-7-methylthieno[3,2-d]pyrimidine

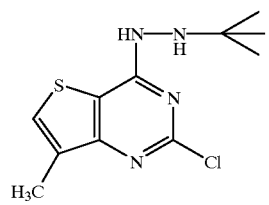

To 6 ml of a solution of 438 mg (2.0 mol) of 2,4-dichloro-7-metylthieno[3,2-d]pyrimidine and 445 mg (4.4 mmol) of triethylamine in DMF was added 249 mg (2.0 mmol) of t-butylhydrazine hydrochloride under ice cooling. The reaction mixture was stirred at the same temperature for one hour and then allowed to resume room temperature, followed by stirring for further 16 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1:2) to give 314 mg (yield: 58.0%) of the title compound.

NMR (δ, CDCl$_3$): 1.18 (9H, s), 2.41 (3H, s), 3.62 (1H, br), 7.00 (1H, br), 7.46 (1H, s)

Example 89

2-Allylamino-4-(2-t-butylhydrazino)-7-methylthieno[3,2-d]pyrimidine

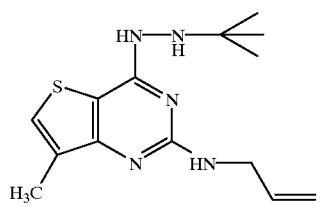

270 mg (1.0 mmol) of 4-(2-t-butylhydrazino)-2-chloro-7-methylthieno[3,2-d]pyrimidine and 914 mg (16.0 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by a silica gel chromatography (eluent: ethyl acetate-hexane=1/4] to give 92 mg (yield: 31.6%) of the title compound.

m.p.: 105 to 107° C.

NMR (δ, CDCl$_3$): 1.17 (9H, s), 2.30 (3H, s) 3.52 (1H, br), 4.09–4.13 (2H, m), 4.76 (1H, br), 5.09–5.13 (1H, m), 5.24–5.29 (1H, m), 5.95–6.05 (1H, m), 6.39 (1H, br), 7.27 (1H, s).

IR (ν, cm$^{-1}$), KBr: 3232, 1577, 1539, 1385.

EI-Mass (m/z, %): 292 (M$^+$+1, 11), 291 (M$^+$, 48), 276 (100), 205 (30)

Example 90

2-Allylamino-7-methyl-4-pivaloylaminothieno[3,2-d]pyrimidine

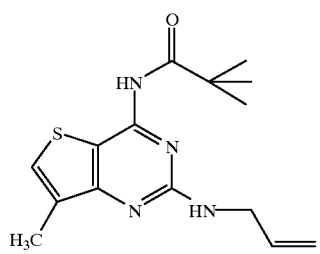

To a solution of 150 mg (0.68 mmol) of 2-allylamino-4-amino-7-methylthieno[3,2-d]pyrimidine and 83 mg (0.82 mmol) of triethylamine in dichloromethane was added 82 mg (0.68 mmol) of pivaloyl chloride, followed by heating under reflux for 1 hour. After completion of the reaction, the solvent was distilled off under reduced pressure. The residue was purified by a silica gel chromatography (eluent: ethyl acetate-hexane=1/4] to give 90 mg (yield: 43.5%) of the title compound.

m.p.: 88 to 89° C.

NMR (δ, CDCl$_3$): 1.36 (9H, s), 2.32 (3H, s), 4.12–4.15 (2H, m), 4.98 (1H, br), 5.12–5.16 (1H, m), 5.25–5.31 (1H, m), 5.94–6.04 (1H, m), 7.43 (1H, s).

IR (ν, cm$^{-1}$), KBr: 3336, 2972, 1694, 1582, 1564, 1480, 802.

EI-Mass (m/z, %): 305 (M$^+$+1, 17), 304 (M$^+$, 92), 289 (100), 219 (27), 205 (53)

Example 91

2-Allylamino-4-(t-butylcarbamoyl)amino-7-methylthieno[3,2-d]pyrimidine

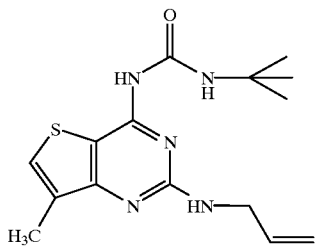

To a solution of 306 mg (1.4 mmol) of di-t-butyldicarbonate in acetonitrile was added 122 mg (1.0 mmol) of N,N-dimethylaminopiridine at room temperature, followed by stirring for 20 minutes. 220 mg (1.0 mmol) of 2-allylamino-4-amino-7-methylthieno[3,2-d]pyrimidine was added to the reaction solution, followed by stirring at room temperature for 2 hours. Further, after 102 mg (1.4 mmol) of t-butylamine was added to the mixture, the reaction mixture was subjected to heating under reflux for 16 hours. After completion of the reaction, the solvent was distilled off under reduced pressure. The residue was purified by a silica gel chromatography (eluent: ethyl acetate-hexane=1/23 to give 161 mg (yield: 50.5%) of the title compound.

NMR (δ, CDCl$_3$): 1.47 (9H, s), 2.32 (3H, s), 4.07–4.11 (2H, m), 5.00 (1H, br), 5.16–5.20 (1H, m), 5.27–5.33 (1H, m), 5.95–6.05 (1H, m), 6.99 (1H, br), 7.33 (1H, s), 9.24 (1H, br)

Example 92

2-Allylamino-4-(t-butylcarbamoyl)amino-7-methylthieno[3,2-d]pyrimidine hydrochloride

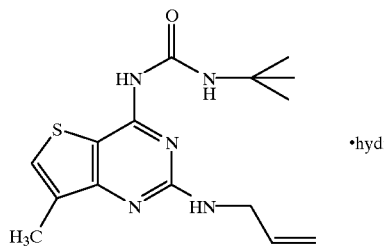

·hydrochloride

A 4 N hydrochloric acid-ethyl acetate solution was added dropwise to a solution of 398 mg (1.3 mmol) of 2-allylamino-4-(t-butylcarbamoyl)amino-7-methylthieno[3,2-d]pyrimidine in ethyl acetate under ice cooling. Crystals thus precipitated were filtered out to give 400 mg (yield: 90.3%) of the title compound.

m.p.: 192 to 194° C.

NMR (δ, CDCl$_3$): 1.50 (9H, s), 2.58 (3H, s), 4.10–4.14 (2H, m), 5.28–5.44 (2H, m), 5.88–5.97 (1H, m), 7.59 (1H, s), 8.78 (1H, br), 9.19–9.25 (2H, m), 15.12 (1H, br).

IR (ν, cm$^{-1}$), KBr: 2971, 1662, 1502, 1280, 788.

EI-Mass (m/z, %): 320 (M$^+$+1-HCl, 8), 319 (M$^+$-HCl, 40), 220 (36), 205 (100)

Example 93

2-Allylamino-4-(cyclohexylcarbamoyl)amino-7-methylthieno[3,2-d]pyrimidine

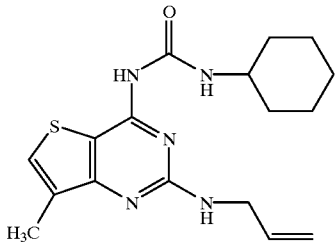

122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 139 mg (1.4 mmol) of cyclohexylamine was added thereto, followed by heating under reflux for 16 hours. After completion of the reaction, the solvent was distilled off under reduced pressure. The residue was purified by a silica gel chromatography (eluent: ethyl acetate-hexane=1/4) to give 172 mg (yield: 49.9%) of the title compound.

m.p.: 152 to 153° C.

NMR (δ, CDCl$_3$): 1.19–1.32 (3H, m), 1.37–1.48 (2H, m), 1.64–1.69 (1H, m), 1.74–1.79 (2H, m), 2.05–2.09 (2H, m), 2.33 (3H, s), 3.75–3.82 (1H, m), 4.07–4.10 (2H, m), 5.07 (1H, br), 5.17–5.21 (1H, m), 5.28–5.34 (1H, m), 5.97–6.06 (1H, m), 6.88 (1H, br), 7.34 (1H, s), 9.21–9.23 (1H, m).

IR (ν, cm$^{-1}$), KBr: 3208, 2932, 1678, 1600, 1494, 792.

EI-Mass (m/z, %): 346 (M$^+$+1, 11), 345 (M$^+$, 51), 246 (26), 231 (60), 205 (100)

Example 94

2-Allylamino-4-(t-butyloxycarbonyl)amino-7-methylthieno[3,2-d]pyrimidine

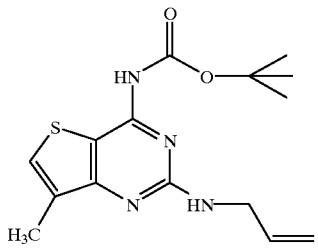

122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 104 mg (1.4 mmol) of t-butanol was added thereto, followed by heating under reflux for 16 hours. After completion of the reaction, the solvent was distilled off under reduced pressure. The residue was purified by a silica gel chromatography (eluent: ethyl acetate-hexane=1/4] to give 54 mg (yield: 16.9%) of the title compound.

NMR (δ, CDCl$_3$): 1.54 (9H, s), 2.32 (3H, s), 4.09–4.13 (2H, m), 5.10–5.15 (2H, m), 5.24–5.29 (1H, m), 5.93–6.03 (1H, m), 7.41 (1H, s), 7.56 (1H, br).

IR (ν, cm$^{-1}$), KBr: 3448, 2980, 1582, 1516, 1488, 802.

EI-Mass (m/z, %): 321 (M$^+$+1, 7), 320 (M$^+$, 38), 220 (75), 205 (100).

Example 95

2-Allylamino-7-methyl-4-(nonylcarbamoyl)aminothieno[3,2-d]pyrimidine hydrochloride

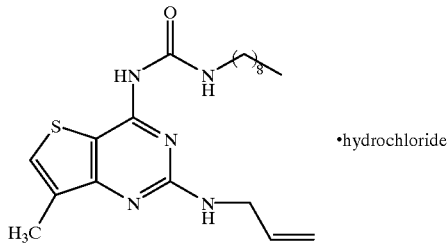

·hydrochloride 122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 201 mg (1.4 mmol) of nonylamine was added thereto, followed by heating under reflux for 16 hours. After completion of the reaction, the solvent was distilled off under reduced pressure. The residue was purified by a silica gel chromatography (eluent: ethyl acetate-hexane=1/4) to give 162 mg of the title compound in the free state. Under ice cooling, a 4N hydrochloric acid-ethyl acetate solution was added dropwise to a solution of the compound in the free state in ethyl acetate. Crystals thus precipitated were filtered to give 177 mg (yield: 41.6%) of the title compound.

m.p. : 181 to 184° C.

NMR (δ, CDCl$_3$): 0.88 (3H, t, J=6.9 Hz), 1.27–1.37 (11H, m), 1.60–1.67 (3H, m), 2.58 (3H, s), 3.41–3.46 (2H, m), 4.09–4.12 (2H, m), 5.27–5.40 (2H, m), 5.88–5.97 (1H, m), 7.60 (1H, s), 8.89 (1H, br), 9.22 (1H, br), 9.97 (1H, br), 15.15 (1H, br).

IR (ν, cm$^{-1}$), KBr: 2924, 1705, 1639, 1498, 793.

EI-Mass (m/z, %): 390 (M$^+$+1, 13), 389 (M$^+$, 51), 374 (5), 231 (82), 205 (100).

Example 96

2-Allylamino-4-(allylcarbamoyl)amino-7-methylthieno[3,2-d]pyrimidine

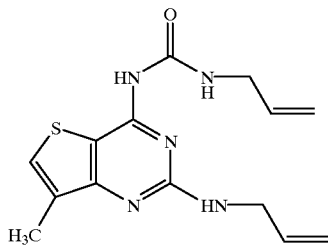

122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 80 mg (1.4 mmol) of allylamine was added thereto, followed by heating under reflux for 16 hours. After completion of the reaction, the solvent was distilled off under reduced pressure. The residue was purified by a silica gel chromatography (eluent: ethyl acetate-hexane=,1/2] to give 54 mg (yield: 18.8%) of the title compound.

m.p. : 164 to 165° C.

NMR (δ, CDCl$_3$): 2.34 (3H, s), 4.03–4.06 (4H, m), 5.11 (1H, br), 5.15–5.21 (2H, m), 5.26–5.33 (2H, m), 5.93–6.02 (2H, m), 6.94 (1H, br), 7.36 (1H, s), 9.44 (1H, br).

IR (ν, cm$^{-1}$), KBr: 3375, 1697, 1585, 1493, 1327, 1273.

EI-Mass (m/z, %): 304 (M$^+$+1, 9), 303 (M$^+$, 48), 246 (18), 231 (45), 205 (100)

Example 97

2-Allylamino-4-(butylcarbamoyl)amino-7-methylthieno[3,2-d]pyrimidine

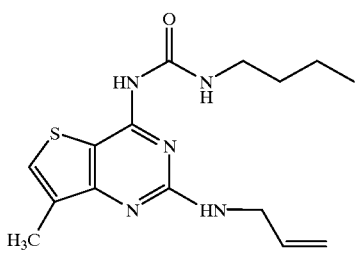

122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 102 mg (1.4 mmol) of n-butylamine was added thereto, followed by heating under reflux for 16 hours. After completion of the reaction, the solvent was distilled off under reduced pressure. The residue was purified by a silica gel chromatography (eluent: ethyl acetate-hexane=1/2] to give 140 mg (yield: 43.9%) of the title compound.

m.p.: 141° C.

NMR (δ, CDCl$_3$): 0.97 (3H, t, J=7 Hz), 1.39–1.48 (2H, m), 1.58–1.65 (2H, m), 2.33 (3H, s), 3.37–3.41 (2H, m), 4.07–4.10 (2H, m), 5.08 (1H, br), 5.17–5.20 (1H, m), 5.28–5.33 (1H, m), 5.95–6.05 (1H, m), 6.97 (1H, br s), 7.34 (1H, s), 9.27 (1H, br).

IR (ν, cm$^{-1}$), KBr: 3413, 2954, 1693, 1597, 1496, 1269.

EI-Mass (m/z, %): 320 (M$^+$+1, 7), 319 (M$^+$, 35), 231 (22), 205 (100)

Example 98

2-Allylamino-7-methyl-4-(1-pyrrolidinylcarbonyl)aminothieno[3,2-d]pyrimidine

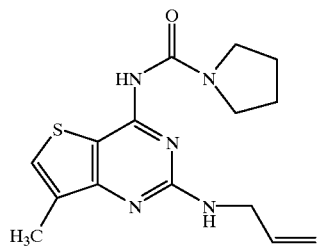

122 mg (1.0 mmol) of N,N-dimethylaminopyridine was added to a solution of 306 mg (1.4 mmol) of di-t-butyldicarbonate in acetonitrile at room temperature, followed by stirring 20 minutes. After 220 mg (1.0 mmol) of 2-allylamino-4-amino-7-methylthieno[3,2-d]pyrimidine was added to the reaction solution, the mixture was stirred at room temperature for 2 hours. Further, 142 mg (2.0 mmol) of pyrrolidine was added thereto, followed by heating under reflux for 16 hours. After completion of the reaction, the solvent was distilled off under reduced pressure. The residue was purified by a silica gel chromatography (eluent: ethyl acetate-hexane=1/2] to give 181 mg (yield: 57.1%) of the title compound.

m.p.: 98 to 101° C.

NMR (δ, CDCl$_3$) 55° C: 1.98 (4H, br), 2.31 (3H, s), 3.52 (4H, br), 4.11 (2H, br), 4.83 (1H, br), 5.10–5.28 (2H, m), 5.94–6.02 (1H, m), 6.92 (1H, br), 7.38 (1H, s).

IR (ν, cm$^{-1}$), KBr: 3263, 2866, 1628, 1554, 1416, 1365.

EI-Mass (m/z, %): 318 (M$^+$+1, 4), 317 (M$^+$, 19), 246 (38), 231 (100), 205 (17)

Reference Example 38

2-Chloro-7-methyl-4-(2-propynylamino)thieno[3,2-d]pyrimidine

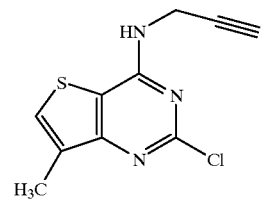

In DMF, 700 mg (3.4 mol) of 2,4-dichloro-7-methylthieno[3,2-d]pyrimidine was dissolved, and then an aqueous solution of 413 mg (7.5 mmol) of 2-propynylamine was added dropwise thereto under ice cooling over 5 minutes. The reaction solution was stirred at 0° C. for 1 hour and allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/4) to give 620 mg (yield: 76.5%) of the title compound.

NMR (δ, CDCl₃): 2.33–2.34 (1H, m), 2.42 (3H, s), 4.46–4.48 (2H, m), 5.15 (1H, br), 7.39 (1H, s)

Example 99

2-Allylamino-7-methyl-4-(2-propynylamino)thieno[3,2-d]pyrimidine

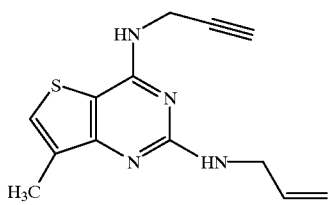

285 mg (1.2 mmol) of 2-chloro-7-methyl-4-(2-propynylamino)thieno[3,2-d]pyrimidine and 1.14 mg (19.2 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/2) to give 168 mg (yield: 54.2%) of the title compound.

m.p.: 95 to 96° C.

NMR (δ, CDCl₃): 2.27 (1H, t, J=2.6 Hz), 2.32 (3H, s), 4.11–4.15 (2H, m), 4.38–4.40 (2H, m), 4.75 (1H, br), 4.94 (1H, br), 5.10–5.13 (1H, m), 5.24–5.30 (1H, m), 5.96–6.05 (1H, m), 7.19 (1H, s).

IR (ν, cm⁻¹), KBr: 3431, 2920, 1456, 675.

EI-Mass (m/z, %): 259 (M⁺+1, 13), 258 (M⁺, 71), 243 (100), 231 (7), 217 (9)

Reference Example 39

2-Chloro-7-methyl-4-(2-methyl-2-propenylamino)thieno[3,2-d]pyrimidine

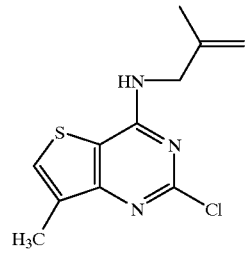

In DMF, 700 mg (3.4 mol) of 2,4-dichloro-7-methylthieno[3,2-d]pyrimidine was dissolved, and 759 mg (7.5 mmol) of triethylamine was added thereto, followed by adding 404 mg (3.8 mmol) of 2-methyl-2-propenylamine thereto, under ice cooling. The reaction solution was stirred at 0° C. for 1 hour and allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by a silica gel chromatography (eluent: ethyl acetate-hexane=1/4) to give 687 mg (yield: 79.3%) of the title compound.

NMR (δ, CDCl₃): 1.83 (3H, s), 2.43 (3H, s), 4.24 (2H, d, J=6.0 Hz), 4.92–4.95 (2H, m), 5.12 (1H, br), 7.37 (1H, s)

Example 100

2-Allylamino-7-methyl-4-(2-methyl-2-propenylamino)thieno[3,2-d]pyrimidine

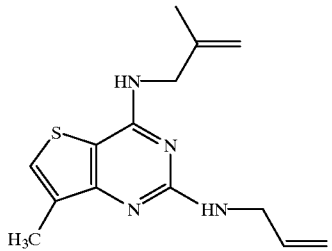

305 mg (1.2 mmol) of 2-chloro-7-methyl-4-(2-methyl-2-propenylamino)thieno[3,2-d]pyrimidine and 1.14 g (19.2 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 108 mg (yield: 32.7%) of the title compound.

m.p.: 83° C.

NMR (δ, CDCl₃): 1.80 (3H, s), 2.32 (3H, s), 4.09–4.13 (2H, m), 4.17 (2H, d, J=6.0 Hz), 4.69 (1H, br), 4.86–4.93

(3H, m), 5.08–5.12 (1H, m), 5.23–5.29 (1H, m), 5.95–6.05 (1H, m), 7.17 (1H, s).

IR (ν, cm⁻¹), KBr: 3421, 2918, 1524, 789.

EI-Mass (m/z, %): 275 (M⁺+1, 15), 274 (M⁺, 73), 259 (100), 233 (12), 219 (21).

Reference Example 40

2-Chloro-7-methyl-4-(3-methyl-2-butenylamino) thieno[3,2-d]pyrimidine

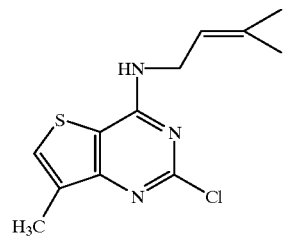

To 10 ml of a solution of 438 mg (2.0 mmol) of 2,4-dichloro-7-metylthieno[3,2-d]pyrimidine and 445 mg (4.4 mmol) of triethylamine in DMF was added 243 mg (2.0 mmol) of 3-methyl-2-butenylamine hydrochloride under ice cooling. The reaction mixture was stirred at the same temperature for one hour and then allowed to resume room temperature, followed by stirring for further 2 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/4) to give 396 mg (yield: 74.0%) of the title compound.

NMR (δ, CDCl₃): 1.76 (3H, s), 1.78 (3H, s), 2.42 (3H, s), 4.22 (2H, t, J=6 Hz), 4.87 (1H, br), 5.32–5.37 (1H, m), 7.35 (1H, s)

Example 101

2-Allylamino-7-methyl-4-(3-methyl-2-butenylamino)thieno[3,2-d]pyrimidine

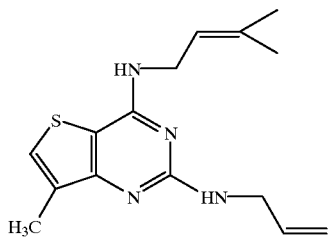

268 mg (1.0 mmol) of 2-chloro-7-methyl-4-(3-methyl-2-butenylamino)thieno[3,2-d]pyrimidine and 914 mg (16.0 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 201 mg (yield: 69.8%) of the title compound.

m.p.: 114 to 115° C.

NMR (δ, CDCl₃): 1.74 (3H, s), 1.76 (3H, s), 2.32 (3H, s), 4.12–4.17 (4H, m), 4.49 (1H, br), 4.87 (1H, br), 5.09–5.13 (1H, m), 5.24–5.30 (1H, m), 5.33–5.37 (1H, m), 5.96–6.06 (1H, m), 7.15 (1H, s).

IR (ν, cm⁻¹), KBr: 3429, 1516, 1454, 1381, 1269.

EI-Mass (m/z, %): 289 (M⁺+1, 19), 288 (M⁺, 90), 273 (100), 247 (18), 205 (95)

Reference Example 41

2-Chloro-4-(trans-cinnamylamino)-7-methylthieno [3,2-d]pyrimidine

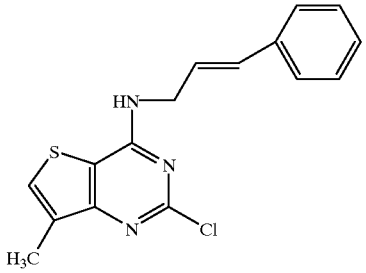

To 10 ml of a solution of 438 mg (2.0 mmol) of 2,4-dichloro-7-metylthieno[3,2-d]pyrimidine and 445 mg (4.4 mmol) of triethylamine in DMF was added 339 mg (2.0 mmol) of trans-cinnamylamine hydrochloride under ice cooling. The reaction mixture was stirred at the same temperature for one hour and then allowed to resume room temperature, followed by stirring for further 2 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/4) to give 341 mg (yield: 54.0%) of the title compound.

NMR (δ, CDCl₃): 2.44 (3H, s), 4.45–4.48 (2H, m), 5.13 (1H, br), 6.30–6.37 (1H, m), 6.65 (1H, d, J=16 Hz), 7.24–7.40 (6H, m)

Example 102

2-Allylamino-4-(trans-cinnamylamino)-7-methylthieno[3,2-d]pyrimidine

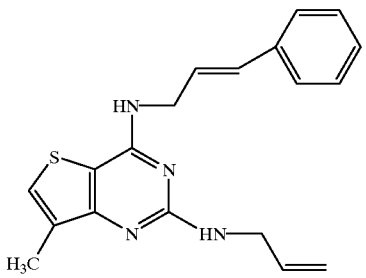

316 mg (1.0 mmol) of 2-chloro-4-(trans-cinnamylamino)-7-methylthieno[3,2-d]pyrimidine and 914 mg (16.0 mmol)

of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 274 mg (yield: 81.5%) of the title compound.

m.p.: 82 to 84° C.

NMR (δ, CDCl$_3$): 2.33 (3H, s), 4.12–4.16 (2H, m), 4.37–4.40 (2H, m), 4.73 (1H, br), 4.92 (1H, br), 5.09–5.13 (1H, m), 5.24–5.30 (1H, m), 5.96–6.06 (1H, m), 6.32–6.39 (1H, m), 6.61 (1H, d, J=16 Hz), 7.18–7.39 (6H, m).

IR (ν, cm$^{-1}$), KBr: 3448, 1558, 1524, 1454, 1338.

EI-Mass (m/z, %): 337 (M$^+$+1, 23), 236 (M$^+$, 100), 321 (53), 295 (7), 245 (38), 91 (18)

Reference Example 42

2,4-Dichloro-7-ethylthieno[3,2-d]pyrimidine

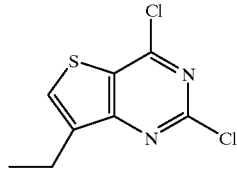

To 1.21 g (6.5 mmol) of methyl 3-amino-4-ethylthiophene-2-carboxylate was added 1.95 g (32.5 mmol) of urea, and the resulting mixture was heated at 200° C. for 1.5 hours. The mixture was allowed to resume room temperature, and then 20 ml of DMF was added thereto, followed by heating under reflux for one hour. After completion of the reaction, ice water was added to the reaction mixture, and crystals thus precipitated were filtered, followed by drying, adding 8.67 g (56.6 mmol) of phosphorus oxychloride and 685 mg (5.7 mmol) of N,N-dimethylaniline thereto and heating under reflux for 3 hours. After completion of the reaction, ice water was added to the reaction mixture, and crystals thus precipitated were filtered to give 831 mg (yield: 64.7%) of the title compound.

NMR (δ, CDCl$_3$): 1.37 (3H, t, J=8 Hz), 2.92–2.98 (2H, m), 7.74 (1H, s)

Reference Example 43

4-Allylamino-2-chloro-7-ethylthieno[3,2-d]pyrimidine

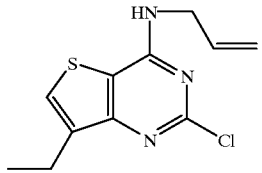

In 6 ml of DMF, 500 mg (2.1 mmol) of 2,4-dichloro-7-etylthieno[3,2-d]pyrimidine was dissolved, and then 269 mg (4.7 mmol) of allylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 483 mg (yield: 88.8%) of the title compound.

NMR (δ, CDCl$_3$): 1.33 (3H, t, J=8 Hz), 2.86–2.91 (2H, m), 4.29–4.32 (2H, m), 5.09 (1H, br), 5.22–5.26 (1H, m), 5.29–5.34 (1H, m), 5.95–6.05 (1H, m), 7.37 (1H, s)

Example 103

2,4-Diallylamino-7-ethylthieno[3,2-d]pyrimidine

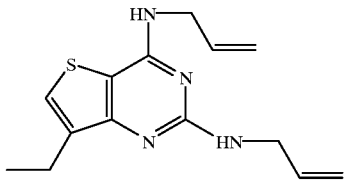

304 mg (1.2 mmol) of 4-allylamino-2-chloro-7-ethylthieno[3,2-d]pyrimidine and 1.10 g (19.2 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 284 mg (yield: 86.3%) of the title compound.

m.p.: 55° C.

IR (ν, cm$^{-1}$), KBr: 3414, 2964, 1631, 1520, 1329, 839.

NMR (δ, CDCl$_3$): 1.31 (3H, t, J=8 Hz), 2.74–2.80 (2H, m), 4.09–4.13 (2H, m), 4.20–4.24 (2H, m), 4.66 (1H, br), 4.89 (1H, br), 5.08–5.12 (1H, m), 5.15–5.19 (1H, m), 5.23–5.30 (2H, m) 5.95–6.05 (2H, m), 7.17 (1H, s).

EI-Mass (m/z, %): 275 (M$^+$+1, 14), 274 (M$^+$, 66), 259 (100), 246 (6), 233 (15), 218 (14)

Reference Example 44

4-t-Butylamino-2-chloro-7-ethylthieno[3,2-d]pyrimidine

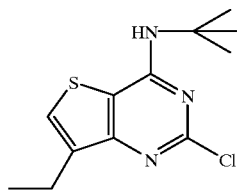

In 5 ml of DMF, 330 mg (1.4 mol) of 2,4-dichloro-7-etylthieno[3,2-d]pyrimidine was dissolved, and then 228 mg (3.1 mmol) of t-butylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 312 mg (yield: 81.7%) of the title compound.

NMR (δ, CDCl$_3$): 1.32 (3H, t, J=8 Hz), 1.57 (9H, s), 2.84–2.90 (2H, m), 4.72 (1H, br), 7.29 (1H, s)

Example 104

2-Allylamino-4-t-butylamino-7-ethylthieno[3,2-d]pyrimidine

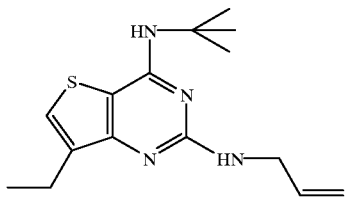

269 mg (1.0 mmol) of 4-butylamino-2-chloro-7-ethylthieno[3,2-d]pyrimidine and 914 mg (16.0 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 241 mg (yield: 83.1%) of the title compound.

IR (ν, cm$^{-1}$), film: 3427, 2964, 1583, 1213, 793.

NMR (δ, CDCl$_3$): 1.30 (3H, t, J=8 Hz), 1.54 (9H, s), 2.72–2.78 (2H, m), 4.09–4.12 (2H, m), 4.40 (1H, br), 4.89 (1H, br), 5.09–5.12 (1H, m), 5.23–5.29 (1H, m), 5.96–6.06 (1H, m), 7.12 (1H, s).

EI-Mass (m/z, %): 291 (M$^+$+1, 14), 290 (M$^+$, 74), 275 (11), 233 (39), 219 (100)

Reference Example 45

2,4-Dichloro-7-propylthieno[3,2-d]pyrimidine

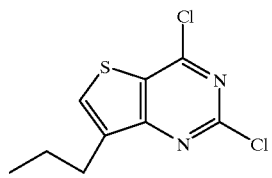

To 1.15 g (5.8 mmol) of methyl 3-amino-4-propylthiophene-2-carboxylate was added 1.73 g (28.9 mmol) of urea, and the resulting mixture was heated at 200° C. for 1.5 hours. The mixture was allowed to resume room temperature, and 50 ml of DMF was added thereto, followed by heating under reflux for one hour. After completion of the reaction, ice water was added to the reaction mixture, and crystals thus precipitated were filtered out, followed by drying, adding 18.16 g (118.0 mmol) of phosphorus oxychloride and 1.43 g (551.8 mmol) of N,N-dimethylaniline thereto and heating under reflux for 3 hours. After completion of the reaction, ice water was added to the reaction mixture, and crystals thus precipitated were filtered to give 886 mg (yield: 62.1%) of the title compound.

NMR (δ, CDCl$_3$): 1.01 (3H, t, J=7 Hz), 1.74–1.83 (2H, m), 2.88–2.92 (2H, m), 7.73 (1H, s)

Reference Example 46

4-Allylamino-2-chloro-7-propylthieno[3,2-d]pyrimidine

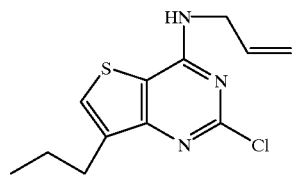

In 5 ml of DMF, 371 mg (1.5 mmol) of 2,4-dichloro-7-propylthieno[3,2-d]pyrimidine was dissolved, and then 188 mg (3.3 mmol) of allylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 244 mg (yield: 60.7%) of the title compound.

NMR (δ, CDCl$_3$): 1.00 (3H, t, J=7 Hz), 1.71–1.81 (2H, m), 2.81–2.85 (2H, m), 4.29–4.32 (2H, m), 5.08 (1H, br), 5.22–5.26 (1H, m), 5.29–5.34 (1H, m), 5.95–6.05 (1H, m), 7.36 (1H, s)

Example 105

2,4-Diallylamino-7-propylthieno[3,2-d]pyrimidine

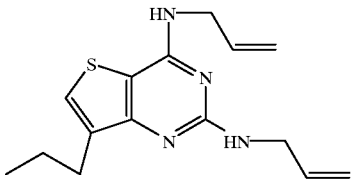

189 mg (0.71 mmol) of 4-allylamino-2-chloro-7-propylthieno[3,2-d]pyrimidine and 644 mg (11.3 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent:

ethyl acetate-hexane=1/4) to give 116 mg (yield: 56.9%) of the title compound.

IR (v, cm$^{-1}$), KBr: 3427, 2958, 1587, 1516, 920, 793.

NMR (δ, CDCl$_3$):. 0.99 (3H, t, J=7 Hz), 1.61–1.80 (2H, m), 2.70–2.74 (2H, m), 3.34–4.13 (2H, m), 4.20–4.24 (2H, m), 4.63 (1H, br), 4.86 (1H, br), 5.08–5.12 (1H, m), 5.15–5.19 (1H, m), 5.23–5.30 (2H, m), 5.95–6.05 (2H, m), 7.16 (1H, s).

EI-Mass (m/z, %): 289 (M$^+$+1, 8), 288 (M$^+$, 37), 273 (11), 260 (27), 247 (20), 217 (19)

Reference Example 47

4-t-Butylamino-2-chloro-7-propylthieno[3,2-d]pyrimidine

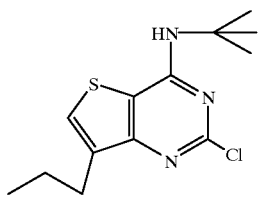

In 5 ml of DMF, 371 mg (1.5 mmol) of 2,4-dichloro-7-propylthieno[3,2-d]pyrimidine was dissolved, and then 241 mg (3.3 mmol) of t-butylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 173 mg (yield: 40.6%) of the title compound.

NMR (δ, CDCl$_3$): 0.99 (3H, t, J=7 Hz), 1.57 (9H, s), 1.70–1.80 (2H, m), 2.80–2.84 (2H, m), 4.72 (1H, br), 7.29 (1H, s)

Example 106

2-Allylamino-4-t-butylamino-7-propylthieno[3,2-d]pyrimidine

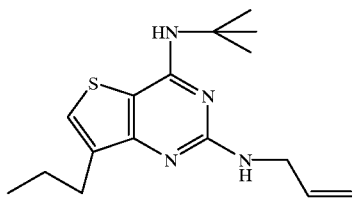

173 mg (0.61 mmol) of 4-t-butylamino-2-chloro-7-propylthieno[3,2-d]pyrimidine and 557 mg (9.8 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 142 mg (yield: 76.3%) of the title compound.

NMR (δ, CDCl$_3$): 0.98 (3H, t, J=7 Hz), 1.53 (9H, s), 1.69–1.79 (2H, m), 2.68–2.72 (2H, m), 4.08–4.12 (2H, m), 4.39 (1H, br), 4.87 (1H, br), 5.08–5.12 (1H, m), 5.23–5.29 (1H, m), 5.96–6.06 (1H, m), 7.11 (1H, s).

IR (v, cm$^{-1}$), film: 3427, 2960, 1581, 1516, 793.

EI-Mass (m/z, %): 305 (M$^+$+1, 15), 304 (M$^+$, 75), 289 (100), 276 (28), 247 (27), 233 (80)

Reference Example 48

2-Chloro-4-methylamino-7-propylthieno[3,2-d]pyrimidine

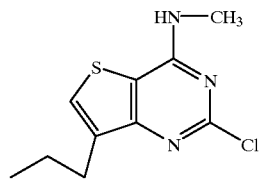

To 10 ml of a solution of 100 mg (0.41 mmol) of 2,4-dichloro-7-propylthieno[3,2-d]pyrimidine in DMF was added 40% methylamine solution in methanol under ice cooling. The reaction mixture was stirred at the same temperature for one hour and then allowed to resume room temperature, followed by stirring for further 2 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/2) to give 50 mg (yield: 51.5%) of the title compound.

NMR (δ, CDCl$_3$): 1.00 (3H, t, J=7 Hz), 1.71–1.81 (2H, m), 2.81–2.85 (2H, m), 3.22 (3H, d, J=5 Hz), 5.01 (1H, br), 7.34 (1H, s)

Example 107

2-Allylamino-4-methylamino-7-propylthieno[3,2-d]pyrimidine

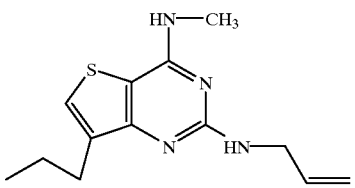

50 mg (0.21 mmol) of 2-chloro-4-methylamino-7-propylthieno[3,2-d]pyrimidine and 189 mg (3.31 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent:

ethyl acetate-hexane=1/4) to give 37 mg (yield: 68.5%) of the title compound.

NMR (δ, CDCl₃): 0.99 (3H, t, J=7 Hz), 1.70–1.80 (2H, m), 2.70–2.74 (2H, m), 3.12 (3H, d, J=5 Hz), 4.11–4.15 (2H, m), 4.58 (1H, br), 4.86 (1H, br), 5.09–5.13 (1H, m), 5.24–5.29 (1H, m), 5.97–6.06 (1H, m)), 7.14 (1H, s).

IR (ν, cm⁻¹), KBr: 2952, 1534, 1249, 906, 785.

EI-Mass (m/z, %): 263 (M⁺+1, 8), 262 (M⁺, 48), 247 (100)

Reference Example 49

2,4-Dichloro-7-isopropylthieno[3,2-d]pyrimidine

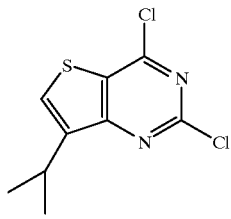

To 1.25 g (6.3 mmol) of methyl 3-amino-4-isopropylthiophene-2-carboxylate was added 1.88 g (31.4 mmol) of urea, and the resulting mixture was heated at 200° C. for 1.5 hours. The mixture was allowed to resume room temperature, and 50 ml of DMF was added thereto, followed by heating under reflux for one hour. After completion of the reaction, ice water was added to the reaction mixture, and crystals thus precipitated were filtered out, followed by drying, adding 4.16 g (27.2 mmol) of phosphorus oxychloride and 329 mg (2.7 mmol) of N,N-dimethylaniline thereto and heating under reflux for 3 hours. After completion of the reaction, ice water was added to the reaction mixture, and crystals thus precipitated were filtered to give 399 mg (yield: 28.8%) of the title compound.

NMR (δ, CDCl₃): 1.38 (6H, d, J=7 Hz), 3.45–3.52 (1H, m), 7.73 (1H, s)

Reference Example 50

4-Allylamino-2-chloro-7-isopropylthieno[3,2-d]pyrimidine

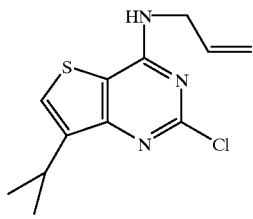

In 5 ml of DMF, 71 mg (0.29 mmol) of 2,4-dichloro-7-isopropylthieno[3,2-d]pyrimidine was dissolved, and then 36 mg (0.63 mmol) of allylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 73 mg (yield: 94.8%) of the title compound.

NMR (δ, CDCl₃): 1.34 (6H, d, J=7 Hz), 3.41–3.48 (1H, m), 4.29–4.32 (2H, m), 5.01 (1H, br), 5.22–5.26 (1H, m), 5.29–5.34 (1H, m), 5.95–6.05 (1H, m), 7.36 (1H, s)

Example 108

2,4-Diallylamino-7-isopropylthieno[3,2-d]pyrimidine

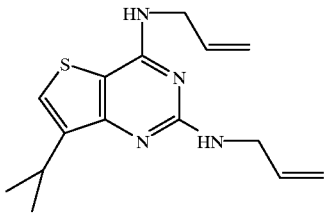

70 mg (0.26 mmol) of 4-allylamino-2-chloro-7-isopropylthieno[3,2-d]pyrimidine and 239 mg (4.2 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (30 ml×2). After the organic layer was washed with brine and dried over anhydrous sodium sulfate, the solvent was distilled off. The residue was purified by silica gel chromatography (eluent: ethyl acetate-hexane=1/4) to give 67 mg (yield: 89.3%) of the title compound.

IR (ν, cm⁻¹), KBr: 3429, 2958, 1587, 1514, 1454, 922, 793.

NMR (δ, CDCl₃): 1.33 (6H, d, J=7 Hz), 3.25–3.32 (1H, m), 4.09–4.12 (2H, m), 4.20–4.24 (2H, m), 4.62 (1H, br), 4.87 (1H, br), 5.08–5.19 (2H, m), 5.23–5.30 (2H, m), 5.94–6.06 (2H, m), 7.16 (1H, s).

EI-Mass (m/z, %): 289 (M⁺+1, 11), 288 (M⁺, 54), 273 (100), 260 (14), 247 (10)

Reference Example 51

2-Chloro-7-isopropyl-4-methylaminothieno[3,2-d]pyrimidine

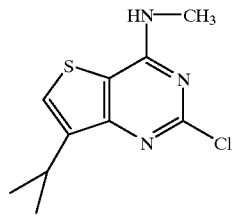

To 10 ml of a solution of 100 mg (0.41 mmol) of 2,4-dichloro-7-isopropylthieno[3,2-d]pyrimidine in DMF was added 40% methylamine solution in methanol under ice cooling. The reaction mixture was stirred at the same temperature for one hour and then allowed to resume room temperature, followed by stirring for further 2 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/2) to give 90 mg (yield: 92.0%) of the title compound.

NMR (δ, CDCl$_3$): 1.34 (6H, d, J=7 Hz), 3.22 (3H, d, J=5 Hz), 3.39–3.49 (1H, m), 5.03 (1H, br), 7.34 (1H, s)

Example 109

2-Allylamino-7-isopropyl-4-methylaminothieno[3,2-d]pyrimidine

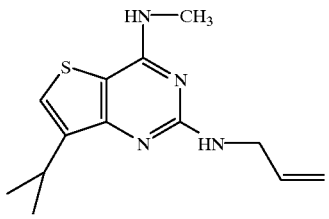

90 mg (0.37 mmol) of 2-chloro-7-isopropyl-4-methylaminothieno[3,2-d]pyrimidine and 340 mg (5.96 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 89 mg (yield: 91.1%) of the title compound.

NMR (δ, CDCl$_3$): 1.32 (6H, d, J=7 Hz), 3.11 (3H, d, J=5 Hz), 3.25–3.32 (1H, m), 4.11–4.14 (2H, m), 4.57 (1H, br), 4.85 (1H, br), 5.09–5.12 (1H, m), 5.24–5.30 (1H, m), 5.97–6.07 (1H, m), 7.14 (1H, s).

IR (ν, cm$^{-1}$), film: 2958, 1594, 1513, 792.

EI-Mass (m/z, %): 263 (M$^+$+1, 9), 262 (M$^+$, 52), 247 (100)

Reference Example 52

2,4-Dichloro-7-phenylthieno[3,2-d]pyrimidine

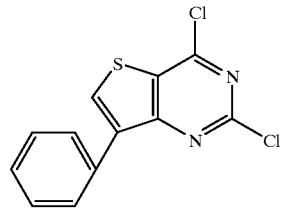

To 2.04 g (8.7 mmol) of methyl 3-amino-4-phenylthiophene-2-carboxylate was added 2.62 g (43.7 mmol) of urea, and the resulting mixture was heated at 200° C. for 1.5 hours. The mixture was allowed to resume room temperature, and 50 ml of DMF was added thereto, followed by heating under reflux for one hour. After completion of the reaction, ice water was added to the reaction mixture, and crystals thus precipitated were filtered out, followed by drying, adding 10.76 g (70.2 mmol) of phosphorus oxychloride and 851 mg (7.0 mmol) of N,N-dimethylaniline thereto and heating under reflux for 3 hours. After completion of the reaction, ice water was added to the reaction mixture, and crystals thus precipitated were filtered to give 341 mg (yield: 13.9%) of the title compound.

NMR (δ, CDCl$_3$): 7.42–7.46 (1H, m), 7.49–7.54 (2H, m), 7.90–7.93 (2H, m), 8.17 (1H, s)

Reference Example 53

4-Allylamino-2-chloro-7-phenylthieno[3,2-d]pyrimidine

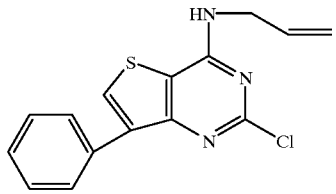

In 1 ml of DMF, 176 mg (0.63 mmol) of 2,4-dichloro-7-phenylthieno[3,2-d]pyrimidine was dissolved, and then 79 mg (1.4 mmol) of allylamine was added dropwise thereto under ice cooling over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (30 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 168 mg (yield: 88.9%) of the title compound.

NMR (δ, CDCl$_3$): 4.32–4.36 (2H, m), 5.12 (1H, br), 5.25–5.28 (1H, m), 5.32–5.37 (1H, m), 5.98–6.07 (1H, m), 7.36–7.40 (1H, m), 7.45–7.50 (2H, m), 7.80 (1H, s), 7.89–7.92 (2H, m)

Example 110

2,4-Diallylamino-7-phenylthieno[3,2-d]pyrimidine

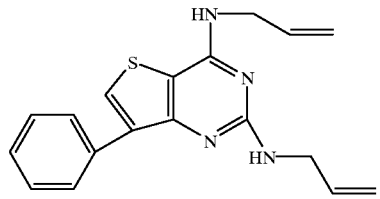

168 mg (0.56 mmol) of 4-allylamino-2-chloro-7-phenylthieno[3,2-d]pyrimidine and 508 mg (8.9 mmol) of allylamine were heated in a sealed tube at 140° C. for 16 hours. After completion of the reaction, the reaction mixture was allowed to resume room temperature, followed by adding a saturated aqueous sodium hydrogen carbonate solution thereto and extraction with ethyl acetate (30 ml×2). After the organic layer was washed with brine and dried over anhydrous sodium sulfate, the solvent was distilled off. The residue was purified by silica gel chromatography (eluent:

ethyl acetate-hexane=1/4) to give 154 mg (yield: 85.3%) of the title compound.

m.p.: 98 to 100° C.

IR (ν, cm$^{-1}$), KBr: 3429, 1593, 1545, 1495, 789, 696.

NMR (δ, CDCl$_3$): 4.12–4.16 (2H, m), 4.26–4.30 (2H, m), 4.70–4.73 (1H, m), 4.95–4.97 (1H, m), 5.13–5.16 (1H, m), 5.21–5.24 (1H, m), 5.27–5.35 (2H, m), 5.98–6.09 (2H, m), 7.29–7.38 (1H, m), 7.44–7.48 (2H, m), 7.67 (1H, s), 8.02–8.04 (2H, m).

EI-Mass (m/z, %): 323 (M$^+$+1, 14), 322 (M$^+$, 49), 321 (75), 307 (100), 281 (19)

Reference Example 54

7-Bromothieno[3,2-d]pyrimidine-2,4(1H,3H)-dione

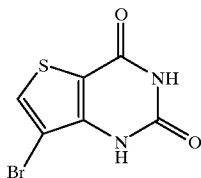

To 250 ml of a solution of 7.31 g (52.2 mmol) of thieno[3,2-d]pyrimidine-2,4(1H,3H)-dione in acetic acid was added 25.0 g (156 mmol) of bromine at room temperature, followed by heating at 80° C. for 2 hours. After completion of the reaction, the solvent was distilled off under reduced pressure. Ice water was added to the residue, followed by filtering out crystals thus precipitated to give 7.24 g (yield: 56.2%) of the title compound.

NMR (δ, DMSO-d$_6$): 8.24 (1H, s), 11.44 (1H, br), 11.56 (1H, br)

Reference Example 55

7-Bromo-2,4-dichlorothieno[3,2-d]pyrimidine

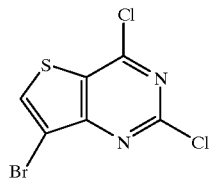

To 3.00 g (12.1 mmol) of 7-bromothieno[3,2-d]pyrimidine-2,4 (1H,3H)-dione were added 18.55 g (121.0 mmol) of phosphorus oxychloride and 3.83 g (48.4 mmol) of pyridine, followed by heating under reflux for 3 hours. After completion of the reaction, ice water was added thereto, followed by filtering out crystals thus precipitated to give 1.35 g (yield: 39.1%) of the title compound.

NMR (δ, CDCl3): 8.11 (1H, s).

EI-Mass (m/z, %): 288 (M$^+$+6, 8), 286 (M$^+$+4, 49), 284 (M$^+$+2, 100), 282 (M$^+$, 61)

Reference Example 56

4-Allylamino-7-bromo-2-chlorothieno[3,2-d]pyrimidine

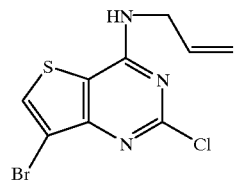

To 5 ml of a solution of 426 mg (1.5 mmol) of 7-bromo-2,4-dichlorothieno[3,2-d]pyrimidine in DMF was added 188 mg (3.3 mmol) of allylamine under ice cooling. The reaction mixture was stirred at the same temperature for one hour and then allowed to resume room temperature, followed by stirring for further 1 hours. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/4) to give 359 mg (yield: 78.6%) of the title compound.

NMR (δ, CDCl$_3$): 4.30–4.34 (2H, m), 5.24–5.35 (3H, m), 5.95–6.04 (1H, m), 7.74 (1H, s)

Example 111

2,4-Diallylamino-7-bromothieno[3,2-d]pyrimidine

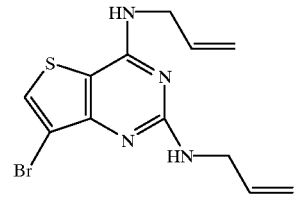

305 mg (1.0 mmol) of 4-allylamino-7-bromo-2-chlorothieno[3,2-d]pyrimidine and 914 mg (16.0 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 304 mg (yield: 93.3%) of the title compound.

m.p.: 87 to 88° C.

NMR (δ, CDCl$_3$): 4.11–4.15 (2H, m), 4.21–4.25 (2H, m), 4.75 (1H, br), 5.10–5.31 (5H, m), 5.93–6.04 (2H, m), 7.54 (1H, s).

IR (ν, cm$^{-1}$), KBr: 3433, 3070, 1554, 1520, 1354, 1292.

EI-Mass (m/z, %): 326 (M$^+$+2, 42), 324 (M$^+$, 41), 311 (100), 309 (100), 285 (9), 283 (13)

Reference Example 57

2-Chloro-4-(2-carbamoylethylamino)-7-methylthieno[3,2-d]pyrimidine

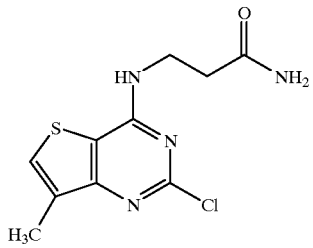

In 10 ml of DMF, 1.0 g (4.9 mmol) of 2,4-dichloro-7-methylthieno[3,2-d]pyrimidine was dissolved, and then 668 mg (5.37 mmol) of β-alanineamide hydrochloride and 1.09 g (10.7 mmol) of triethylamine were added thereto under ice cooling. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/8) to give 1.05 g (yield: 79.8%) of the title compound.

NMR (δ, DMSO-$d_6$): 2.28 (3H, s), 2.44 (2H, t, J=7 Hz), 3.64 (2H, dd, J=6 Hz, 7 Hz), 6.87 (1H, br), 7.38 (1H, br), 7.79 (1H, s), 8.34 (1H, t, J=6 Hz)

Example 112

2-Allylamino-4-[2-(allylcarbamoyl)ethylamino]-7-methylthieno[3,2-d]pyrimidine

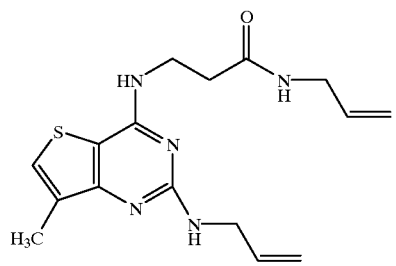

324 mg (1.2 mmol) of 2-chloro-4-(2-carbamoylethylamino)-7-methylthieno[3,2-d]pyrimidine and 1.096 g (19.2 mmol) of allylamine were heated in a sealed tube at 160° C. for 16 hours. After completion of the reaction, the reaction mixture was allowed to resume room temperature, followed by adding a saturated aqueous sodium hydrogen carbonate solution thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/1) to give 248 mg (yield: 62.5%) of the title compound.

m.p.: 95 to 96° C.

NMR (δ, CDCl$_3$): 2.31 (3H, s), 2.58 (2H, t, J=6 Hz), 3.85–3.92 (4H, m), 4.08–4.13 (2H, m), 4.98 (1H, br), 5.08–5.16 (3H, m), 5.22–5.29 (1H, m), 5.42 (1H, br), 5.72–6.06 (3H, m), 7.17 (1H, s).

IR (ν, cm$^{-1}$), KBr: 3440, 2293, 1666, 1589, 1566, 1527, 918, 795.

EI-Mass (m/z, %): 332 (M$^+$+1, 17), 331 (M$^+$, 81), 316 (100), 247 (60), 205 (51)

Reference Example 58

2-Chloro-4-dodecylamino-7-methylthieno[3,2-d]pyrimidine

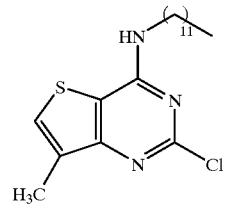

In 1 ml of DMF, 700 mg (3.2 mmol) of 2,4-dichloro-7-methylthieno[3,2-d]pyrimidine was dissolved, and then 1.30 g (7.0 mmol) of dodecylamine was added dropwise thereto over 5 minutes. The reaction solution was stirred at 0° C. for one hour and then allowed to resume room temperature, followed by stirring for further 1 hour. After completion of the reaction, ice water was added to the reaction mixture, followed by extraction with ethyl acetate (50 ml×3). After the organic layer was washed successively with 1N hydrochloric acid, water and brine and dried over anhydrous sodium sulfate, the solvent was distilled off under reduced pressure. The residue was purified by silica gel chromatography (eluent: ethyl acetate-hexane=1/10) to give 745 mg (yield: 63.4%) of the title compound.

NMR (δ, CDCl$_3$): 0.88 (3H, t, J=7 Hz), 1.26–1.44 (18H, m), 1.65–1.72 (2H, m), 2.42 (3H, s), 3.63–3.68 (2H, m), 4.98 (1H, br), 7.35 (1H, s)

Example 113

2-Allylamino-4-dodecylamino-7-methylthieno[3,2-d]pyrimidine

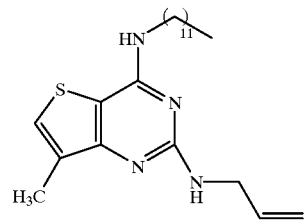

442 mg (1.2 mmol) of 2-chloro-4-dodecylamino-7-methylthieno[3,2-d]pyrimidine and 1.10 g (19.2 mmol) of allylamine were heated in a sealed tube at 140° C. for 16 hours. After completion of the reaction, the reaction mixture was allowed to resume room temperature, followed by adding a saturated aqueous sodium hydrogen carbonate thereto and extraction with ethyl acetate (50 ml×2). After the organic layer was washed with brine and dried over anhydrous sodium sulfate, the solvent was distilled off. The residue was purified by silica gel chromatography (eluent: ethyl acetate-hexane=1/4) to give 209 mg (yield: 44.8%) of the title compound.

NMR (δ, CDCl₃): 0.88 (3H, t, J=7 Hz), 1.26–1.44 (18H, m), 1.61–1.68 (2H, m), 2.32 (3H, s), 3.54–3.59 (2H, m), 4.11–4.14 (2H, m), 4.58 (1H, br), 4.86 (1H, br), 5.09–5.12 (1H, m), 5.24–5.29 (1H, m), 5.96–6.05 (1H, m), 7.16 (1H, s).

IR (v⁻¹m) KBr: 3429, 2922, 1560, 1522, 1462, 789.

EI-Mass (m/z, %): 389 (M⁺+1, 13), 388 (M⁺, 49), 373 (100)

Example 114

2,4,7-Triallylaminothieno[3,2-d]pyrimidine

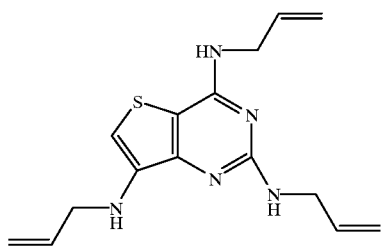

120 mg (0.37 mmol) of 2,4-diallylamino-7-bromothieno[3,2-d]pyrimidine, 337 mg (5.9 mmol) of allylamine, 56 mg (0.41 mmol) of potassium carbonate and 1 mg of copper were heated in a sealed tube at 180° C. for 5 hours. After completion of the reaction, the reaction mixture was allowed to resume room temperature, followed by distilling off excess allylamine under reduced pressure. The residue was purified by silica gel chromatography (eluent: ethyl acetate-hexane=1/8) to give 81 mg (yield: 72.9%) of the title compound.

NMR (δ, CDCl₃): 3.83–3.86 (2H, m), 4.08–4.12 (2H, m), 4.19–4.23 (2H, m), 4.63–4.65 (1H, m), 4.83–4.86 (1H, m), 5.09–5.35 (6H, m), 5.93–6.05 (4H, m).

IR (v, cm⁻¹), film: 1535, 1330, 782.

EI-Mass (m/z, %): 302 (M⁺+1, 21), 301 (M⁺, 100), 272 (44)

Test Example

Determination of Oxygen Partial Pressure Increasing Action

Actions of the thienopyrimidine derivatives of the present invention to increase oxygen partial pressure in the arterial blood were determined according to the following method:

Sprague-Dawley male rats having body weights of about 250 g were anesthetized (i.p.) with urethane and cannulated to the respiratory tracts, femoral arteries and femoral veins. An olive oil-charcoal powder suspension (10 mg/ml) was introduced in an amount of 0.8 ml/kg through the respiratory tract cannulae into the lungs to cause the rats to be under hypoxic state (PaO₂ Δ75 mmHg). The thienopyrimidine derivatives listed in Table 2 were intravenously administered to these hypoxemic model rats continuously at a rate of 0.1 mg/kg/min, and arterial blood oxygen partial pressure value (PaO₂) of each rat was measured at the time point of 10 minutes after completion of administration using a blood gas analyzer (Ciba Corning 800 series). Gains (ΔPaO₂) were determined based on results of PaO₂ measurement made before and after administration of the test compounds. The results are shown in Table 2.

TABLE 2

| Example | Compound | ΔPaO₂ (mmHg) |
|---|---|---|
| 66 | 2,4-Diallylamino-7-methylthieno[3,2-d]pyrimidine | 26 |
| 68 | 2-Allylamino-4-t-butylamino-7-methylthieno[3,2-d]pyrimidine | 31 |
| 70 | 2-Allylamino-4-cyclohexylamino-7-methylthieno[3,2-d]pyrimidine hydrochloride | 42 |
| 71 | 2-Allylamino-4-diallylamino-7-methylthieno[3,2-d]pyrimidine hydrochloride | 26 |
| 76 | 2-Allylamino-4-ethylamino-7-methylthieno[3,2-d]pyrimidine | 33 |
| 79 | 4-(1-Adamantylamino)-2-allylamino-7-methylthieno[3,2-d]pyrimidine | 36 |
| 80 | 2-Allylamino-7-methyl-4-nonylaminothieno[3,2-d]pyrimidine | 28 |
| 81 | 2-Allylamino-4-butylamino-7-methylthieno[3,2-d]pyrimidine | 29 |
| 84 | 2-Allylamino-7-methyl-4-(1-methylpropylamino)-7-methylthieno[3,2-d]pyrimidine | 27 |
| 103 | 2,4-Diallyamino-7-ethylthieno[3,2-d]pyrimidine | 30 |
| 104 | 2-Allylamino-4-t-butylamino-7-ethylthienol[3,2-d]pyrimidine | 41 |
| 105 | 2,4-Diallylamino-7-propylthieno[3,2-d]pyrimidine | 28 |
| 106 | 2-Allylamino-4-t-butylamino-7-propylthieno[3,2-d]pyrimidine | 28 |
| 107 | 2-Allylamino-4-methylamino-7-propylthieno[3,2-d]pyrimidine | 41 |

What is claimed is:

1. A pyrimidine nucleus-containing compound represented by formula (I):

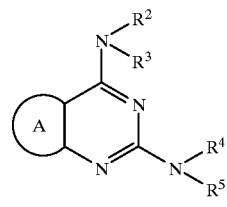

(I)

wherein ring A represents the ring of formula (a):

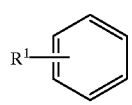

(a)

in which R¹ is a nitro group, an amino group, a mono- or di-C₁–C₃ alkylamino group or a mono- or di-allylamino group or a halogen atom;

R² and R⁴ independently represent a hydrogen atom, a C₁–C₂₀ alkyl group or a C₃–C₆ alkenyl group; and R³ and R⁵ independently represent a C₁–C₂₀ alkyl group, a C₃–C₆ alkenyl group, an alkynyl group selected from the group consisting of 2-propynyl, 2-butynyl, 2-pentynyl and 2-heptynyl, an aralkyl group selected from the group consisting of benzyl, phenethyl, 1-naphthylmethyl and 2-naphthylmethyl, a C₃–C₆ cycloalkyl group, an adamantyl group, a pyridylmethyl group, a furylmethyl group, a thienylmethyl group, a cinnamyl group, a $C_1$–$C_6$ aliphatic acyl group, a $C_1$–$C_6$ alkoxycarbonyl group, a substituted $C_1$–$C_{20}$ alkyl group selected from the group consisting of methoxymethyl, 2-methoxyethyl, 2-ethoxyethyl, 2-propoxyethyl, 3-methoxypropyl, an amino-, carbamoyl-, hydroxy- or halo-substituted alkyl, a substituted carbamoyl group selected from the group consisting of a $C_1$–$C_2$ linear alkyl- or alkenyl-carbamoyl group, a $C_3$–$C_8$ cycloalkyl- or cycloalkenyl-carbamoyl group, an arylcarbamoyl group, a 1-pyrrolidinocarbonyl group, a piperidinocarbonyl group, a morpholinocarbonyl group, a 1-thiomorpholinocarbonyl group, a mono- or di-$C_1$–$C_6$ alkyl-amino group, a 1-pyrrolidino group, a pyridylmethyl group, a piperidino group, a morpholino group or a 1-thiomorpholinyl group; or either $R^2$ and $R^3$ or $R^4$ and $R^5$, together with the nitrogen atom to which they are attached, may form a 1-aziridinyl ring, 1-azetidinyl ring, a 1-pyrrolidinyl ring, a piperidino ring, a 1-perhydroazepinyl ring, a piperazino ring, a morpholino ring or a 1-thiomorpholinyl ring each of which may be substituted by a methyl, ethyl or propyl group, a benzyl group, a naphthylmethyl group, a benzhydryl group or a 4,4'-difluorobenzhydryl group;

with the proviso that at least one of $R^2$ to $R^5$ is a $C_3$–$C_6$ alkenyl group, or acid addition salt thereof.

2. The pyrimidine nucleus-containing compound or acid addition salt thereof according to claim 1, wherein ring A represents the ring of the formula (a) and $R^1$ is a nitro group or an amino group.

3. The pyrimidine nucleus-containing compound or acid addition salt thereof according to claim 1, wherein ring A represents the ring of the formula (a), $R^2$ is a hydrogen atom and $R^3$ is an allyl group.

4. The pyrimidine nucleus-containing compound or acid addition salt thereof according to claim 1, wherein ring A represents the ring of the formula (a), $R^4$ is a hydrogen atom and $R^5$ is an allyl group.

5. A method for preparing the pyrimidine nucleus-containing compound of the formula (I) in claim 1, which comprises the steps of:

a) reacting a 2,4-dione compound represented by the formula:

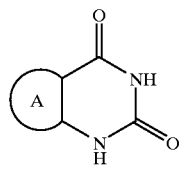

wherein ring A is defined in claim 1, with a halogenating reagent in the present of a base to prepare a 2,4-dihalo compound represented by formula:

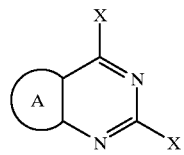

wherein X is a halogen atom, b) reacting said 2,4-dihalo compound with an amine derivative represented by formula:

wherein $R^2$ and $R^3$ are defined in claim 1, to prepare a 2-halo-4-amino compound represented by the formula:

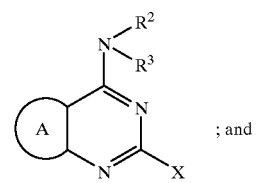

; and c) reacting said 2-halo-4-amino compound with an amine compound represented by the formula:

wherein $R^4$ and $R^5$ are defined in claim 1, to prepare said compound of the formula (I).

6. A pharmaceutical composition, comprising:

the pyrimidine nucleus-containing compound or acid addition salt thereof according to claim 1; and a pharmaceutically acceptable excipient.

7. A method for amelioration of blood oxygen partial pressure, comprising:

administering an effective amount of the composition according to claim 6 to a subject in need thereof.

* * * * *